(12) United States Patent
Mirkin et al.

(10) Patent No.: US 12,264,344 B2
(45) Date of Patent: Apr. 1, 2025

(54) PROTEIN/OLIGONUCLEOTIDE CORE-SHELL NANOPARTICLE THERAPEUTICS

(71) Applicant: Northwestern University, Evanston, IL (US)

(72) Inventors: Chad A. Mirkin, Wilmette, IL (US); Jeffrey D. Brodin, Evanston, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 15/502,955

(22) PCT Filed: Aug. 19, 2015

(86) PCT No.: PCT/US2015/045971
§ 371 (c)(1),
(2) Date: Feb. 9, 2017

(87) PCT Pub. No.: WO2016/028940
PCT Pub. Date: Feb. 25, 2016

(65) Prior Publication Data
US 2017/0232109 A1  Aug. 17, 2017

Related U.S. Application Data

(60) Provisional application No. 62/137,183, filed on Mar. 23, 2015, provisional application No. 62/039,608,
(Continued)

(51) Int. Cl.
*C12N 9/96* (2006.01)
*A61K 38/43* (2006.01)
(Continued)

(52) U.S. Cl.
CPC ............ *C12N 9/2471* (2013.01); *A61K 38/44* (2013.01); *A61K 38/47* (2013.01); *A61K 47/549* (2017.08);
(Continued)

(58) Field of Classification Search
CPC .. A61K 48/005; A61K 31/7115; A61K 38/00; A61K 48/00; A61K 31/7088;
(Continued)

(56) References Cited

U.S. PATENT DOCUMENTS 3,687,808 A   8/1972   Merigan, Jr. et al.
4,469,863 A   9/1984   Ts'o et al.
(Continued)

FOREIGN PATENT DOCUMENTS

CN   102165061 A   8/2011
EP   1072679 A2    1/2001
(Continued)

OTHER PUBLICATIONS

Shukla et al., Development of Streptavidin-Based Nanocomplex for siRNA Delivery. Mol. Pharmaceutics 2013, 10, 4534-4545 (Year: 2013).*

(Continued)

*Primary Examiner* — Arthur S Leonard
(74) *Attorney, Agent, or Firm* — Wolf, Greenfield & Sacks, P.C.

(57) ABSTRACT

The present disclosure is directed to core-shell nanoparticles, compositions comprising core-shell nanoparticles, and methods of their use.

21 Claims, 25 Drawing Sheets

Specification includes a Sequence Listing.

Related U.S. Application Data filed on Aug. 20, 2014, provisional application No. 62/039,340, filed on Aug. 19, 2014.

(51) Int. Cl.

| | | |
|---|---|---|
| *A61K 38/44* | (2006.01) | |
| *A61K 38/47* | (2006.01) | |
| *A61K 47/54* | (2017.01) | |
| *A61K 47/69* | (2017.01) | |
| *C07K 19/00* | (2006.01) | |
| *C12N 9/08* | (2006.01) | |
| *C12N 9/38* | (2006.01) | |
| *C12P 3/00* | (2006.01) | |
| *C12P 19/02* | (2006.01) | |
| *C12P 19/14* | (2006.01) | |
| *B82Y 5/00* | (2011.01) | |

(52) U.S. Cl.
CPC .......... *A61K 47/6921* (2017.08); *C07K 19/00* (2013.01); *C12N 9/0065* (2013.01); *C12N 9/96* (2013.01); *C12P 3/00* (2013.01); *C12P 19/02* (2013.01); *C12P 19/14* (2013.01); *C12Y 111/01006* (2013.01); *C12Y 302/01023* (2013.01); *B82Y 5/00* (2013.01); *Y02P 20/582* (2015.11)

(58) Field of Classification Search
CPC .............. A61K 31/713; A61K 49/0093; A61K 49/0423; A61K 31/7125; A61K 39/0008; A61K 2121/00; A61K 2800/652; A61K 2800/654; C12N 15/87; C12N 15/11; C12N 15/00
See application file for complete search history.

(56) References Cited

U.S. PATENT DOCUMENTS

| | | |
|---|---|---|
| 4,476,301 A | 10/1984 | Imbach et al. |
| 4,489,055 A | 12/1984 | Couvreur et al. |
| 4,845,205 A | 7/1989 | Huynh Dinh et al. |
| 4,981,957 A | 1/1991 | Lebleu et al. |
| 5,008,050 A | 4/1991 | Cullis et al. |
| 5,023,243 A | 6/1991 | Tullis |
| 5,034,506 A | 7/1991 | Summerton et al. |
| 5,112,963 A | 5/1992 | Pieles et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,264,423 A | 11/1993 | Cohen et al. |
| 5,264,562 A | 11/1993 | Matteucci |
| 5,264,564 A | 11/1993 | Matteucci |
| 5,264,618 A | 11/1993 | Felgner et al. |
| 5,270,163 A | 12/1993 | Gold et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,637,459 A | 6/1997 | Burke et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,830,653 A | 11/1998 | Froehler et al. |
| 6,005,096 A | 12/1999 | Matteucci et al. |
| 6,051,698 A | 4/2000 | Janjic et al. |
| 6,080,580 A | 6/2000 | Baker et al. |
| 6,228,642 B1 | 5/2001 | Baker et al. |
| 6,287,860 B1 | 9/2001 | Monia et al. |
| 6,361,944 B1 | 3/2002 | Mirkin et al. |
| 6,506,564 B1 | 1/2003 | Mirkin et al. |

(56) References Cited

U.S. PATENT DOCUMENTS

| | | |
|---|---|---|
| 6,677,153 B2 | 1/2004 | Iversen |
| 6,942,972 B2 * | 9/2005 | Farooqui ............ A61K 47/6807 |
| | | 435/177 |
| 7,048,949 B2 | 5/2006 | Sligar et al. |
| 7,223,833 B1 | 5/2007 | Nielsen et al. |
| 7,332,586 B2 | 2/2008 | Franzen et al. |
| 7,404,969 B2 | 7/2008 | Chen et al. |
| 7,514,099 B2 | 4/2009 | Chen et al. |
| 7,563,618 B2 | 7/2009 | Gryaznov et al. |
| 7,611,728 B2 | 11/2009 | Kidane et al. |
| 7,667,004 B2 | 2/2010 | Zhong et al. |
| 7,833,992 B2 | 11/2010 | Vargeese et al. |
| 7,956,176 B2 | 6/2011 | McSwiggen et al. |
| 7,964,578 B2 | 6/2011 | Vargeese et al. |
| 8,323,686 B2 | 12/2012 | Mirkin et al. |
| 8,431,544 B1 | 4/2013 | Agrawal et al. |
| 8,507,200 B2 | 8/2013 | Mirkin et al. |
| 9,139,827 B2 | 9/2015 | Mirkin et al. |
| 9,364,443 B2 | 6/2016 | Beduneau et al. |
| 9,506,056 B2 | 11/2016 | Mirkin et al. |
| 9,532,948 B2 | 1/2017 | Mirkin et al. |
| 9,549,901 B2 | 1/2017 | Shi et al. |
| 9,580,708 B2 | 2/2017 | Uhlmann et al. |
| 9,617,541 B2 | 4/2017 | Mirkin et al. |
| 9,844,562 B2 | 12/2017 | Mirkin et al. |
| 9,889,209 B2 | 2/2018 | Mirkin et al. |
| 9,902,959 B2 | 2/2018 | Collard et al. |
| 10,098,958 B2 | 10/2018 | Mirkin et al. |
| 10,182,988 B2 | 1/2019 | Mirkin et al. |
| 10,208,310 B2 | 2/2019 | Mader et al. |
| 10,370,656 B2 | 8/2019 | Mirkin et al. |
| 10,391,116 B2 | 8/2019 | Mirkin et al. |
| 10,398,784 B2 | 9/2019 | Mirkin et al. |
| 10,653,780 B2 | 5/2020 | Hope et al. |
| 10,792,251 B2 | 10/2020 | Mirkin et al. |
| 2002/0172711 A1 | 11/2002 | Martin et al. |
| 2003/0022848 A1 | 1/2003 | Baker et al. |
| 2003/0147966 A1 | 8/2003 | Franzen et al. |
| 2003/0181412 A1 | 9/2003 | Erikson |
| 2004/0014956 A1 | 1/2004 | Woolf et al. |
| 2004/0023382 A1 | 2/2004 | Dean et al. |
| 2004/0158051 A1 | 8/2004 | Ozkan et al. |
| 2004/0219565 A1 | 11/2004 | Kauppinen et al. |
| 2005/0197315 A1 | 9/2005 | Taira et al. |
| 2005/0214782 A1 | 9/2005 | Chen et al. |
| 2005/0244858 A1 | 11/2005 | Rossi et al. |
| 2006/0008907 A1 | 1/2006 | Friedman et al. |
| 2006/0019917 A1 | 1/2006 | Guerciolini et al. |
| 2006/0025363 A1 | 2/2006 | Breitenbach et al. |
| 2006/0035344 A1 | 2/2006 | Pachuk et al. |
| 2006/0083781 A1 | 4/2006 | Shastri et al. |
| 2006/0148124 A1 | 7/2006 | Wilson |
| 2006/0252037 A1 | 11/2006 | Kolesnick et al. |
| 2006/0292174 A1 | 12/2006 | de los Rios et al. |
| 2007/0148251 A1 | 6/2007 | Hossainy et al. |
| 2008/0097092 A1 | 4/2008 | Khvorova et al. |
| 2008/0194463 A1 | 8/2008 | Weller et al. |
| 2008/0213177 A1 | 9/2008 | Rademacher et al. |
| 2008/0220072 A1 | 9/2008 | Unger et al. |
| 2008/0274454 A1 | 11/2008 | Mirkin et al. |
| 2008/0292545 A1 | 11/2008 | Lin et al. |
| 2008/0306016 A1 | 12/2008 | Mirkin et al. |
| 2008/0311182 A1 | 12/2008 | Ferrari et al. |
| 2009/0018028 A1 | 1/2009 | Lindsay et al. |
| 2009/0209629 A1 | 8/2009 | Mirkin et al. |
| 2009/0299045 A1 | 12/2009 | Richards et al. |
| 2009/0317802 A1 | 12/2009 | Bhatia et al. |
| 2009/0324706 A1 | 12/2009 | Mirkin et al. |
| 2010/0003317 A1 | 1/2010 | Akinc et al. |
| 2010/0092486 A1 | 4/2010 | Kandimalla et al. |
| 2010/0111968 A1 | 5/2010 | Branigan et al. |
| 2010/0136682 A1 | 6/2010 | Mirkin et al. |
| 2010/0184844 A1 | 7/2010 | Mirkin et al. |
| 2010/0233084 A1 | 9/2010 | Narasimhaswamy et al. |
| 2010/0233141 A1 | 9/2010 | Polach et al. |
| 2010/0233270 A1 | 9/2010 | Mirkin et al. |
| 2010/0310872 A1 | 12/2010 | Nakamura |
| 2011/0020242 A1 | 1/2011 | Zheng et al. |
| 2011/0111974 A1 | 5/2011 | Mirkin et al. |
| 2011/0223257 A1 | 9/2011 | Zhao et al. |
| 2011/0229529 A1 | 9/2011 | Irvine et al. |
| 2011/0244026 A1 | 10/2011 | Guild et al. |
| 2011/0256224 A1 | 10/2011 | Sigalov |
| 2011/0262347 A1 * | 10/2011 | Ruoslahti ............... A61K 38/04 |
| | | 424/1.11 |
| 2012/0244230 A1 | 9/2012 | Mirkin et al. |
| 2012/0282186 A1 | 11/2012 | Mirkin et al. |
| 2012/0288935 A1 * | 11/2012 | Mirkin ............... A61K 41/0052 |
| | | 435/375 |
| 2013/0004520 A1 | 1/2013 | Andersson et al. |
| 2013/0034599 A1 | 2/2013 | Thaxton et al. |
| 2013/0123333 A1 | 5/2013 | Mirkin et al. |
| 2013/0136714 A1 | 5/2013 | Wang et al. |
| 2013/0178610 A1 | 7/2013 | Mirkin et al. |
| 2013/0295129 A1 | 11/2013 | Irvine et al. |
| 2013/0330839 A1 | 12/2013 | Suh et al. |
| 2014/0005258 A1 | 1/2014 | Mirkin et al. |
| 2014/0294927 A1 | 10/2014 | Thaxton et al. |
| 2016/0237429 A1 | 8/2016 | Cubillos-Ruiz et al. |
| 2016/0310425 A1 | 10/2016 | Mirkin et al. |
| 2017/0044544 A1 | 2/2017 | Mirkin |
| 2017/0130231 A1 | 5/2017 | Chae et al. |
| 2018/0200381 A1 * | 7/2018 | Kannan ................. A61K 45/06 |
| 2018/0344873 A1 | 12/2018 | Mirkin et al. |
| 2019/0030185 A1 | 1/2019 | Mirkin et al. |
| 2019/0275166 A1 | 9/2019 | Mirkin et al. |
| 2020/0022913 A1 | 1/2020 | Mirkin et al. |
| 2020/0101156 A1 | 4/2020 | Mirkin et al. |
| 2020/0291394 A1 | 9/2020 | Mirkin et al. |

FOREIGN PATENT DOCUMENTS

| | | | |
|---|---|---|---|
| EP | 1889911 A2 | 2/2008 | |
| EP | 2162117 A2 | 3/2010 | |
| EP | 2 366 406 A1 | 9/2011 | |
| EP | 2399608 A1 | 12/2011 | |
| WO | WO 1994/001550 A1 | 1/1994 | |
| WO | WO 1995/011910 A1 | 5/1995 | |
| WO | WO 97/12896 A1 | 4/1997 | |
| WO | WO-1997/012896 A1 | 4/1997 | |
| WO | WO-1998/039352 A1 | 9/1998 | |
| WO | WO-1999/014226 A2 | 3/1999 | |
| WO | WO 99/27086 A1 | 6/1999 | |
| WO | WO 00/20645 A1 | 4/2000 | |
| WO | WO 2002/044321 A2 | 6/2002 | |
| WO | WO 2003/008539 A2 | 1/2003 | |
| WO | WO 2003/051278 A2 | 6/2003 | |
| WO | WO 2004/047870 A1 | 6/2004 | |
| WO | WO 2005/116226 A2 | 12/2005 | |
| WO | WO 2006/088833 A2 | 8/2006 | |
| WO | WO-2006080946 A2 * | 8/2006 | ......... A61K 39/0005 |
| WO | WO 2006/138145 A1 | 12/2006 | |
| WO | WO 2007/044851 A2 | 4/2007 | |
| WO | WO-2007/047455 A2 | 4/2007 | |
| WO | WO 2007/064857 A2 | 6/2007 | |
| WO | WO 2007/089607 A2 | 8/2007 | |
| WO | WO-2007/122405 A1 | 11/2007 | |
| WO | WO 2008/42156 A1 | 4/2008 | |
| WO | WO-2008/098248 A2 | 8/2008 | |
| WO | WO 2008/106660 A2 | 9/2008 | |
| WO | WO 2008/127789 A2 | 10/2008 | |
| WO | WO-2008/151049 A2 | 12/2008 | |
| WO | WO 2009/012786 A2 | 1/2009 | |
| WO | WO 2009/026412 A1 | 2/2009 | |
| WO | WO 2009/72657 A1 | 6/2009 | |
| WO | WO 2009/105260 A2 | 8/2009 | |
| WO | WO 2009/120887 A2 | 10/2009 | |
| WO | WO 2010/017152 A2 | 2/2010 | |
| WO | WO 2010/017154 A2 | 2/2010 | |
| WO | WO 2010/060110 A1 | 5/2010 | |
| WO | WO 2010/081049 A1 | 7/2010 | |
| WO | WO 2010/081049 A2 | 7/2010 | |
| WO | WO 2010/105209 A1 | 9/2010 | |
| WO | WO 2010/120420 A1 | 10/2010 | |

(56) References Cited

FOREIGN PATENT DOCUMENTS

| | | | |
|---|---|---|---|
| WO | WO 2010/120420 A2 | 10/2010 | |
| WO | WO 2011/017456 A2 | 2/2011 | |
| WO | WO-2011/017690 A2 | 2/2011 | |
| WO | WO-2011/053940 A2 | 5/2011 | |
| WO | WO 2011/072133 A1 | 6/2011 | |
| WO | WO 2011/079290 A1 | 6/2011 | |
| WO | WO 2011/079290 A2 | 6/2011 | |
| WO | WO 2011/113054 A2 | 9/2011 | |
| WO | WO 2011/143608 A1 | 11/2011 | |
| WO | WO 2012/055933 A1 | 5/2012 | |
| WO | WO 2012/068470 A2 | 5/2012 | |
| WO | WO 2012/170771 A1 | 12/2012 | |
| WO | WO 2013/012628 A2 | 1/2013 | |
| WO | WO 2013/016193 A2 | 1/2013 | |
| WO | WO 2013/086207 A1 | 6/2013 | |
| WO | WO 2013/177419 A1 | 11/2013 | |
| WO | WO 2014/025795 A1 | 2/2014 | |
| WO | WO 2014/123935 A1 | 8/2014 | |
| WO | WO 2014/169264 A2 | 10/2014 | |
| WO | WO 2014/172698 A1 | 10/2014 | |
| WO | WO 2015/084884 A2 | 6/2015 | |
| WO | WO 2015/195628 A2 | 12/2015 | |
| WO | WO 2016/057549 A1 | 4/2016 | |
| WO | WO 2016/115320 A1 | 7/2016 | |
| WO | WO 2017/011662 A1 | 1/2017 | |
| WO | WO 2017/035278 A1 | 3/2017 | |
| WO | WO 2018/039629 A2 | 3/2018 | |
| WO | WO 2018/138585 A1 | 8/2018 | |
| WO | WO 2018/152327 A2 | 8/2018 | |
| WO | WO 2019/118883 A2 | 6/2019 | |
| WO | WO 2019/243430 A1 | 12/2019 | |

OTHER PUBLICATIONS

Lohcharoenkal et al., Protein Nanoparticles as Drug Delivery Carriers for Cancer Therapy. vol. 2014, Article ID 180549, 12 pages (Year: 2014).*
KeraFast. Chemoselective Ligation through Copper-free Click Chemistry. Sep. 21, 2012, pp. 1-2, published on-line at http://www.kerafast.com/PDF/Chemoselective_Ligation_Sheet.pdf (Year: 2012).*
Ming et al., Albumin-based Nanoconjugates for Targeted Delivery of Therapeutic Oligonucleotides. Biomaterials. Oct. 2013 ; 34(32):1-22 (Year: 2013).*
Hotz et al., VEGF antisense therapy inhibits tumor growth and improves survival in experimental pancreatic cancer. Surgery 2005; 137:192-9 (Year: 2005).*
Rajur et al., Covalent Protein-Oligonucleotide Conjugates for Efficient Delivery of Antisense Molecules. Bioconjugate Chem. 1997, 8, 935-940 (Year: 1997).*
Poussin et al., Biochemical and functional analyses of gp130 mutants unveil JAK1 as a novel therapeutic target in human inflammatory hepatocellular adenoma. OncoImmunology 2:12, e27090; Dec. 2013; p. 1-8. (Year: 2013).*
Duellman et al., Functional roles of N-linked glycosylation of human matrix metalloproteinase 9. Traffic. Oct. 2015; 16(10): 1108-1126. (Year: 2015).*
Takakura-Yamamoto et al., O-Glycosylated Species of Natural Human Tumor-Necrosis Factor-α. Euro J. Biochem, 1996, 235:431-437. (Year: 1996).*
Lin et al. Site-Specific Bioconjugation of a Murine Dihydrofolate Reductase Enzyme by Copper(I)-Catalyzed Azide-Alkyne Cycloaddition with Retained Activity (PLOS One, 2014, 9(6):e98403, pp. 1-10) (Year: 2014).*
Gosh et al. Use of Maleimide-thiol coupling chemistry for efficient syntheses of oligonucleotide-enzyme conjugate hybridization probe (Bioconjugate Chem, 1990, 1:71-76) (Year: 1990).*
Stevens et al. Chemical modification of enzymes: Critical evaluation of the graphical correlation between residual enzyme activity and number of groups modified. Bulletin Math Bio, 1980, 42:239-255. (Year: 1980).*

Murakami et al., Highly sensitive detection of DNA using enzyme-linked DNA-probe. 1. Colorimetric and fluorometric detection (NAR, 1989, 17:5587-5595) (Year: 1989).*
Cho et al., "Immunostimulatory DNA-based vaccines induce cytotoxic lymphocyte activity by a T-helper cell-independent mechanism," Nature Biotechnology 18:509-514 (2000).
Ahmadi et al., "Shape-Controlled Synthesis of Colloidal Platinum Nanoparticles," Science 272:1924-1926 (1996).
Altschul et al., "Basic Local Alignment Search Tool," J. Mol. Biol., 215:403-410 (1990).
Auyeung et al., "DNA-mediated nanoparticle crystallization into Wulff polyhedral," Nature 505(7481): 73-77 (2014).
Auyeung et al., "Synthetically programmable nanoparticle superlattices using a hollow three-dimensional spacer approach," Nat Nanotechnol 7(1):24-28 (2012).
Auyeung et al., "Transitioning DNA-Engineered Nanoparticle Superlattices from Solution to the Solid State," Adv Mater 24(38):5181-5186 (2012).
Bahnemann, "Mechanisms of Organic Transformations on Semiconductor Particles," Photochemical Conversion and Storage of Solar Energy, 251-276 (1991).
Beers et al., "A Spectrophotometric Method for Measuring the Breakdown of Hydrogen Peroxide by Catalase," J Biol Chem 195(1):133-140 (1952).
Brodin et al., "DNA-mediated engineering of multicomponent enzyme crystals," Proceedings National Academy of Sciences PNAS, 112(15):4564-4569 (2015).
Brodin et al., "Metal-directed, chemictally-tunable assembly of one-, two- and three-dimensional crystalline protein arrays," Nat Chem 4(5): 375-382 (2012).
Brus, "Quantum Crystallites and Nonlinear Optics," Appl. Phys. A53:465-474 (1991).
Cigler et al., "DNA-controlled assembly of a NaTI lattice structure from gold and protein nanoparticles," Nat Mater 9(11): 918-922 (2010).
Concise Encyclopedia of Polymer Science and Engineering, "Polynucleotides," J. I. Kroschwitz Ed., John Wiley & Sons, pp. 858-859 (1990).
Cook, "Medicinal chemistry of antisense oligonucleotides—future opportunities," Anti-Cancer Drug Design, 6:585-607 (1991).
Coyle et al., "DNA-Mediated Assembly of Protein Heterodimers on Membrane Surfaces," J Am Chem Soc 135(13):5012-5016 (2013).
Crawford et al., "Peptide aptamers: Tools for biology and drug discovery," Briefings in Functional Genomics and Proteomics, 2(1):72-79 (2003).
Curtis et al., "A Morphology-Selective Copper Organosol," Angew. Chem. Int. Ed. Engl., 27: 1530-1533 (1988).
De Mesmaeker et. al., "Backbone modifications in oligonucleotides and peptide nucleic acid systems," Current Opinion in Structural Biology, 5:343-355 (1995).
Dotan et al., "Self-Assembly of a Tetrahedral Lectin into Predesigned Diamondlike Protein Crystals," Angew Chem Int Ed 38(16): 2363-2366 (1999).
Eckstein, Oligonucleotides and Analogues, 1st Ed. (Oxford University Press, New York) (1991).
Eltoukhy, et al., "Nucleic acid-mediated intracellular protein delivery by lipid-like nanoparticles," Biomaterials 35(24):6454-6461 (2014).
Englisch et al., "Chemically Modified Oligonucleotides as Probes and Inhibitors," Angewandte Chemie, International Edition, 30:613-722 (1991).
Enustun, et al. "Coagulation of Colloidal Gold," J. Am. Chem. Soc. 85:3317-3328 (1963).
Fattal, et al., "Biodegradable polyalkylcyanoacrylate nanoparticles for the delivery of oligonucleotides," J. Controlled Release 53:137-143 (1998).
Freier et al., "The ups and downs of nucleic acid duplex stability: structure-stability studies on chemically-modified DNA:RNA duplexes," Nucleic Acids Research, 25:4429-4443 (1997).
Hames et al., Gene Probes 1 A Practical Approach, IRL Press, New York (1995).
Hayashi, "Ultrafine particles," J. Vac. Sci. Technol., A5(4):1375-1384 (1987).

(56) References Cited

OTHER PUBLICATIONS

Hayashi, "Ultrafine particles," Physics Today, pp. 44-51 (1987).
Hayat, M. A. (ed.) Colloidal Gold: Principles, Methods, and Applications (Academic Press, San Diego, 1991).
Henglein et al., "Absorption Spectrum and Some Chemical Reactions of Colloidal Platinum in Aqueous Solution," J. Phys. Chem., 99:14129-14136 (1995).
Henglein, "Mechanism of Reactions on Colloidal Microelectrodes and Size Quantization Effects," Topics in Curr. Chem., 143:113-180 (1988).
Henglein, "Small-Particle Research: Physicochemical Properties of Extremely Small Colloidal Metal and Semiconductor Particles," Chem. Rev., 89:1861-1873 (1989).
Hill et al., "Controlling the Lattice Parameters of Gold Nanoparticle FCC Crystals with Duplex DNA Linkers," Nano Lett 8(8): 2341-2344 (2008).
Hurst et al., "Maximizing DNA Loading on a Range of Gold Nanoparticle Sizes," Anal Chem 78(24): 8313-8318 (2006).
International Search Report and Written Opinion from PCT/US15/45971 dated Nov. 25, 2015.
Katz, "The reversible reaction of sodium thymonucleate and mercuric chloride," *J. Am. Chem. Soc.*, 74:2238-2245 (1951).
King et al., "Accurate design of coassembling multi-component protein nanomaterials," Nature 510(7503): 103-108 (2014).
King et al., "Computational design of self-assembling protein nanomaterials with atomic level accuracy," Science 336(6085): 1171-1174 (2012).
Kopylov et al., "Combinatorial Chemistry of Nucleic Acids: SELEX," Molecular Biology 34(6): 940-954 (2000).
Kopylov et al., "Combinatorial Chemistry of Nucleic Acids: SELEX," Molekulyarnaya Biologiya, vol. 34(6):1097-1113 (2000).
Kostiainen et al., "Electrostatic assembly of binary nanoparticle superlattices using protein cages," Nat Nanotechnol 8(1): 52-56 (2013).
Kosturko et al., "The Crystal and Molecular Structure of a 2:1 Complex of 1-Methylthymine-Mercury(II)," Biochemistry, 13:3949-3952 (1974).
Kukowska-Latallo et al., "Efficient transfer of genetic material into mammalian cells using Starburst polyamidoamine dendrimers," Proc. Natl. Acad. Sci. USA 93:4897-4902 (1996).
Liljestrom et al., "Self-assembly and modular functionalization of three-dimensional crystals from oppositely charged proteins," Nat Commun 5(4445) pp. 1-9 (2014).
Liu et al., "New poly(d-glucaramidoamine)s induce DNA nanoparticle formation and efficient gene delivery into mammalian cells," *J. Am. Chem. Soc.* 126:7422-7423 (2004).
Macfarlane et al., "Establishing the Design Rules for DNA-Mediated Programmable Colloidal Crystallization," Angew Chem Int Ed Engl 49(27): 4589-4592 (2010).
Macfarlane et al., "Nanoparticle Superlattice Engineering with DNA," Science 334:204-208 (2011).
Macfarlane et al., "Nucleic Acid-Modified Nanostructures as Programmable Atom Equivalents: Forging a New Table of Elements," Angew Chem Int Ed 52(22): 5688-5698 (2013).
Mann, "Life as a Nanoscale Phenomenon," Angew Chem Int Ed 47(29): 5306-5320 (2008).
Marinakos et al., "Gold Nanoparticles as Templates for the Synthesis of Hollow Nanometer-Sized Conductive Polymer Capsules," Adv. Mater. 11:34-37 (1999).
Marinakos et al., "Template Synthesis of One-Dimensional Au, Au-Poly)pyrrole), and Poly(pyrrole) Nanoparticle Arrays," Chem. Mater. 10:1214-1219 (1998).
Martin et al., "A New Access to 2'O-Alkylated Ribonucleosides and Properties of 2'-O-Alkylated Oligoribonucleotides," Helv. Chim. Acta, 78:486-504 (1995).
Massart, "Preparation of Aqueous Magnetic Liquids in Alkaline and Acidic Media," IEEE Transactions on Magnetics, 17:1247-1248 (1981).
Matijevic et al., "Fine Particles Part II: Formation Mechanisms and Applications," MRS Bulletin, pp. 16-47 (1990).

Mayer et al., Nucleic Acid and Peptide Aptamers: Methods and Protocols (Edited by Mayer, Humana Press) Methods in Molecular Biology (2009).
Mirkin et al., "A DNA-based method for rationally assembling nanoparticles into macroscopic materials," Nature 382:607-609 (1996).
Mozzarelli et al., "Protein Function in the Crystal," Annu Rev Bioph Biom 25:343-365 (1996).
Nielsen et al., "Sequence-selective recognition of DNA by strand displacement with a thymine-substituted polyamide," Science, 254:1497-1500 (1991).
Nykypanchuk et al., "DNA-guided crystallization of colloidal nanoparticles," Nature 451:549-552 (2008).
Olshavsky et al., "Organometallic Synthesis of GaAs Crystallites Exhibiting Quantum Confinement," J. Am. Chem. Soc., 112:9438-9439 (1990).
Oohora et al., "Supramolecular assembling systems formed by heme-heme pocket interactions in hemoproteins," Chem Commun 48(96):11714-11726 (2012).
Padilla et al., "Nanohedra: Using symmetry to design self assembling protein cages, layers, crystals, and filaments," Proc Natl Acad Sci USA 98(5): 2217-2221 (2001).
Park et al., "DNA-programmable nanoparticle crystallization," Nature 451: 553-556 (2008).
Remington's Pharmaceutical Sciences, 16th Edition (1980).
Ringler et al., "Self-Assembly of Proteins into Designed Networks," Science 302(5642):106-109 (2003).
Rudiuk et al., "Enhancement and Modulation of Enzymatic Activity through Higher-Order Structural Changes of Giant DNA-Protein Multibranch Conjugates," Angewandte Chemie International Edition, 51(51):12694-12698 (2012).
Rusling et al., "Functionalizing Designer DNA Crystals with a Triple-Helical Veneer," Angew Chem Int Ed 53(15): 3979-3982 (2014).
Sakai et al., "Protein crystalline frameworks with controllable interpenetration directed by dual supramolecular interactions," Nat Commun 5: 4634 (2014).
Sambrook et al., Molecular Cloning: A Laboratory Manual 2nd ed. (1989).
Samejima et al., "Reconstitution of Acid-denatured Catalase," J Biol Chem 238(10): 3256-3261 (1963).
Sanghvi, Chapter 15, Heterocyclic Base Modification in Nucleic Acids and Their Applications in Antisense Oligonucleotides, Antisense Research and Applications, pp. 289-302, Crooke, S. T. and Lebleu, B., ed., CRC Press (1993).
Schmid, G. (ed.) Clusters and Colloids (VCH, Weinheim) (1994).
Schuttelkopf et al., "PRODRG: a tool for high-throughput crystallography of protein-ligand complexes," Acta Crystallogr D 60: 1355-1363 (2004).
Seeman, "An Overview of Structural DNA Nanotechnology," Mol Biotechnol 37(3): 246-257 (2007).
Sinclair et al., "Generation of protein lattices by fusing proteins with matching rotational symmetry," Nat Nanotechnol 6(9): 558-562 (2011).
Strable et al., "Natural Nanochemical Building Blocks: Icosahedral Virus Particles Organized by Attached Oligonucleotides," Nano Lett 4(8): 1385-1389 (2004).
Stranges et al., "A comparison of successful and failed protein interface designs highlights the challenges of designing buried hydrogen bonds," Protein Sci 22(1): 74-82 (2013).
Thomas, "The Interaction of HgCl2 with Sodium Thymonucleate," J. Am. Chem. Soc., 76:6032-6034 (1954).
Tondelli et al., "Highly efficient cellular uptake of c-myb antisense oligonucleotides through specifically designed polymeric nanospheres," Nucl. Acids Res. 26:5425-5431(1998).
Tuerk et al., "Systematic Evolution of Ligands by Exponential Enrichment: RNA Ligands to Bacteriophage T4 DNA Polymerase," Science 249:505-510 (1990).
Uchida et al., "GaAs Nanocrystals Prepared in Quinoline," J. Phys. Chem., 95:5382-5384 (1992).
Wang et al., "Hierarchical Assembly of Plasmonic Nanosctuctures Using Virus Capsid Scaffolds on DNA Origami Templates," ACS Nano 8(8):7896-7904 (2014).

(56) References Cited

OTHER PUBLICATIONS

Wang et al., "Nanometer-sized Semiconductor Clusters: Materials Synthesis, Quantum Size Effects, and Photophysical Properties," J. Phys. Chem., 95:525-532 (1991).
Weller, "Colloidal Semiconductor Q-Particles: Chemistry in the Transition Region Between Solid State and Molecules," Angew. Chem. Int. Ed. Engl., 32:41-53 (1993).
Wilner et al., "Enzyme cascades activated on topologically programmed DNA scaffolds," Nat Nanotechnol 4(4): 249-254 (2009).
Winfree et al., "Design and self-assembly of two-dimensional DNA crystals," Nature 394(6693): 539-544 (1998).
Xiong et al., "Phase Behavior of Nanoparticles Assembled by DNA Linkers," Phys Rev Lett 102(1): 015504 (2009).
Yamane et al., "On the complexing of desoxyribonucleic acid (DNA) by mercuric ion," J. Am. Chem. Soc., 83:2599-2607 (1961).
Yan et al., "Aptamers and aptamer targeted delivery," RNA Biol. 6(3) 316-320 (2009).
Yan et al., "DNA-Templated Self-Assembly of Protein Arrays and Highly Conductive Nanowires," Science 301(5641): 1882-1884 (2003).
Zhang et al., "A general approach to DNA-programmable atom equivalents," Nat Mater 12(8): 741-746 (2013).
Zhang et al., "A general strategy for the DNA-mediated self-assembly of functional nanoparticles into heterogeneous systems," Nat Nanotechnol 8(11): 865-872 (2013).
Zhang et al., "An extremely stable and orthogonal DNA base pair with a simplified three-carbon backbone," J. Am. Chem. Soc., 127:74-75 (2005).
Zhang et al., "DNA-Directed Three-Dimensional Protein Organization," Angew Chem Int Ed 51(14): 3382-3385 (2012).
Zhang et al., "PowerBLAST: A new network BLAST application for interactive or automated sequence analysis and annotation," Genome Res., 7:649-656 (1997).
Zheng et al., "From Molecular to Macroscopic via the Rational Design of a Self-Assembled 3D DNA Crystal," Nature 461(7260): 74-77 (2009).
Zheng, et al. "Sterically Controlled docking of gold nanoparticles on ferritin surface by DNA hybridization," Nanotechnology 22(27):275312, pp. 1-7 (2011).
Zimmermann, et al., "A Novel Silver(I)-Mediated DNA Base Pair," J. Am. Chem. Soc., 124:13684-13685 (2002).
International Preliminary Report on Patentability from International Application No. PCT/US2015/045971 dated Feb. 21, 2017.
Agbasi-Porter et al., Transcription inhibition using oligonucleotide-modified gold nanoparticles, Bioconjugate Chem., 17(5):1178-83 (2006).
Akhter et al., Gold nanoparticles in theranostic oncology: current state-of-the-art. Expert Opin Drug Deliv. Oct. 2012;9(10):1225-43. Epub Aug. 16, 2012.
Banga et al., Liposomal spherical nucleic acids. J Am Chem Soc. Jul. 16, 2014;136(28):9866-9. doi: 10.1021/ja504845f. Epub Jul. 1, 2014.
Barrat et al., Nucleic acids of mammalian origin can act as endogenous ligands for Toll-like receptors and may promote systemic lupus erythematosus. J Exp Med. Oct. 17, 2005;202(8):1131-9.
Bhattarai et al., "Enhanced Gene and siRNA Delivery by Polycation-Modified Mesoporous Silica Nanoparticles Loaded with Chloroquine," Pharm. Res., 2010, 27, 2556-2568.
Bonoiu et al., Nanotechnology approach for drug addiction therapy: gene ; silencing using delivery of gold nanorod-siRNA nanoplex in dopaminergic neurons. Proc Natl Acad Sci U S A. Apr. 7, 2009;106(14):5546-50. doi:; 10.1073/pnas.0901715106. Epub Mar. 23, 2009.
Briley et al., In Nanomaterials for Biomedicine; American Chemical Society. 2012;1119:1-20.
Calabrese et al., Biocompatible infinite-coordination-polymer nanoparticle-nucleic acid conjugates for antisense gene regulation. Angew Chem Int Ed Engl. Jan. 7, 2015;54(2):476-480. doi: 10.1002/anie.201407946. Epub Nov. 13, 2014.

Chen et al., Kinetics and thermodynamics of DNA hybridization on gold nanoparticles. Nucleic Acids Res. Jun. 2009;37(11):3756-65. doi: 10.1093/nar/gkp230. Epub Apr. 20, 2009.
Chen et al., Nanoparticle-aptamer: an effective growth inhibitor for human cancer cells. IMECE 2009-11966. Jul. 8, 2010;271-2. https://doi.org/10.1115/IMECE2009-11966. 2 pgs.
Chinnathambi et al., Binding mode of CpG Oligodeoxynucleotides to nanoparticles regulates bifurcated cytokine induction via Toll-like Receptor 9. Sci Reports. 2012;2(534):1-9.
Cho et al., Targeted delivery of siRNA-generating DNA nanocassettes using multifunctional nanoparticles. Small. Jun. 10, 2013;9(11):1964-73. doi: 10.1002/smll.201201973. Epub Jan. 6, 2013.
Choi et al., DNA aptamer-passivated nanocrystal synthesis: a facile approach for nanoparticle-based cancer cell growth inhibition. Small. Mar. 2009;5(6):672-5. doi: 10.1002/smll.200801821.
Choi et al., Mechanism for the endocytosis of spherical nucleic acid nanoparticle conjugates, Proc. Natl. Acad. Sci. U.S.A. 2013;110:7625-7630.
Cutler et al., Polyvalent nucleic acid nanostructures. J Am Chem Soc. Jun. 22, 2011;133(24):9254-7. doi:10.1021/ja203375n. Epub Jun. 1, 2011.
Cutler et al., Polyvalent oligonucleotide iron oxide nanoparticle "click" conjugates. Nano Lett. Apr. 14, 2010;10(4):1477-80. doi: 10.1021/nl100477m.
Cutler et al., Spherical nucleic acids. J Am Chem Soc. Jan. 25, 2012;134(3):1376-91. doi: 10.1021/ja209351u. Epub Jan. 9, 2012.
Daniel et al., Gold nanoparticles: assembly, supramolecular chemistry, quantum-size-related properties, and applications toward biology, catalysis, and nanotechnology. Chem Rev. Jan. 2004;104(1):293-346.
Dhar et al., Polyvalent oligonucleotide gold nanoparticle conjugates as delivery vehicles for platinum (IV) warheads. J Am Chem Soc. Oct. 21, 2009;131(41):14652-3. doi: 10.1021/ja907182.
Ding et al., A biomimetic nanovector-mediated targeted cholesterol-conjugated siRNA delivery for tumor gene therapy. Biomaterials. Dec. 2012;33(34):8893-905. doi: 10.1016/j.biomaterials.2012.08.057. Epub Sep. 12, 2012.
Ding et al., A Crosslinked Nucleic Acid Nanogel for Effective siRNA Delivery and Antitumor Therapy. Angew Chem Int Ed Engl. Mar. 12, 2018;57(12):3064-3068. doi:10.1002/anie.201711242. Epub Feb. 22, 2018.
Elbakry et al., "Layer-by-Layer Assembled Gold Nanoparticles for siRNA Delivery," Nano Lett., 2009, 9 (5), 2059-2064.
Englisch et al., "Chemically Modified Oligonucleotides as Probes and Inhibitors" Angewandte Chemie, International Edition, 30:613-629 (1991).
Extended European Search Report mailed Dec. 8, 2017 in connection with EP Application No. 15833938.2.
Fan et al., "Self-Assembly of Ordered, Robust, Three-Dimensional Gold Nanocrystal/Silica Arrays," Science, 2004, 403, 567-571.
Farokhzad et al., Nanomedicine: developing smarter therapeutic and diagnostic modalities, Drug Delivery Rev., 58:1456 (2006).
Giljohann et al., Gene regulation with polyvalent siRNA-nanoparticle conjugates. J Am Chem Soc. Feb. 18, 2009;131(6):2072-3.
Giljohann et al., Gold nanoparticles for biology and medicine. Angew Chem Int Ed Engl. Apr. 26, 2010;49(19):3280-94. doi: 10.1002/anie.200904359.
Giljohann et al., Oligonucleotide loading determines cellular uptake of DNA-modified gold nanoparticles. Nano Lett. Dec. 2007;7(12):3818-21. Epub Nov. 13, 2007.
Godard, G. et al., "Antisense Effects of Cholesterol-Oligodeoxynucleotide Conjugates Associated with Poly(alkylcyanoacrylate) Nanoparticles," Eur. J. Biochem., 1995, 232 (2), 404-410.
Grijalvo et al., Oligonucleotide delivery: a patent review (2010-2013). Expert Opin Ther Pat. Jul. 2014;24(7):801-19. doi:10.1517/13543776.2014.915944. Epub May 5, 2014.
Gryaznov, Oligonucleotide n'-->p5' phosphoramidates and thiophoshoramidates as potential therapeutic agents. Chem Biodivers. Mar. 2010;7(3):477-93. doi: 10.1002/cbdv.200900187. Review.

(56) References Cited

OTHER PUBLICATIONS

Han et al., Drug and gene delivery using gold nanoparticles. NanoBiotechnology. Mar. 2007;3(1):40-5.
Hashmi, Gold-catalyzed organic reactions. Chem Rev. Jul. 2007;107(7):3180-211. Epub Jun. 20, 2007.
Hellstrom et al., Epitaxial growth of DNA-assembled nanoparticle superlattices on patterned substrates. Nano Lett. 2013;13(12):6084-90. doi: 10.1021/nl4033654. Epub Nov. 20, 2013.
Ivanov et al., Interleukin-17 as a drug target in human disease. Trends Pharmacol Sci. Feb. 2009;30(2):95-103. doi: 10.1016/j.tips. 2008.11.004. Epub Jan. 21, 2009.
Jensen et al., Spherical nucleic acid nanoparticle conjugates as an RNAi-based therapy for glioblastoma, Sci. Trans. Med., 5:209ra152 (2013).
Kim et al., Cationic solid lipid nanoparticles reconstituted from low density lipoprotein components for delivery of siRNA. Mol Pharm. Jul.-Aug. 2008;5(4):622-31. doi: 10.1021/mp8000233. Epub May 8, 2008.
Kong et al., Cationic lipid-coated gold nanoparticles as efficient and non-cytotoxic intracellular siRNA delivery vehicles. Pharm Res. Feb. 2012;29(2):362-74. doi: 10.1007/s11095-011-0554-y. Epub Aug. 13, 2011.
Kwoh et al., Stabilization of poly-L-lysine/DNA polyplexes for in vivo gene delivery to the liver. Biochim Biophys Acta. Feb. 16, 1999;1444(2):171-90.
Langer, New methods of drug delivery. Science. Sep. 28, 1990;249(4976):1527-33.
Leander, "Mixed-Monolayer Gold Nanoparticles for Cancer Therapeutics," Nanoscape, 2010, 7 (1), 11-14.
Lee et al., All-in-one target-cell-specific magnetic nanoparticles for simultaneous molecular imaging and siRNA delivery. Angew Chem Int Ed Engl. 2009;48(23):4174-9. doi:10.1002/anie.200805998.
Lee et al., Silver nanoparticle-oligonucleotide conjugates based on DNA with triple cyclic disulfide moieties, Nano Lett., 7: 2112 (2007).
Lenert et al., DNA-like class R inhibitory oligonucleotides (INH-ODNs) preferentially block autoantigen-induced B-cell and dendritic cell activation in vitro and autoantibody production in lupus-prone MRL-Faslpr/lprmice in vivo. Arthritis Research & Therapy. May 2009;11:R79.
Lenert et al., Inhibitory oligonucleotides block the induction of AP-1 transcription factor by stimulatory CpG oligonucleotides in B cells. Antisense Nucleic Acid Drug Dev. 2003;13(3):143-50.
Lennox et al., Characterization of modified antisense oligonucleotides in Xenopus laevis embryos. Oligonucleotides. 2006 Spring;16(1):26-42.
Li et al., Nanofabrication by DNA self-assembly. Materials Today. Elsevier Science. May 1, 2009;12(5)24-32.
Li et al., Nucleolin-targeting liposomes guided by aptamer AS1411 for the delivery of siRNA for the treatment of malignant melanomas. Biomaterials. Apr. 2014;35(12):3840-50. doi: 10.1016/j.biomaterials.2014.01.019. Epub Jan. 31, 2014.
Li et al., Reversible and Chemically Programmable Micelle Assembly with DNA Block-Copolymer Amphiphiles, Nano Lett. 2004;4:1055.
Li et al., Thermal stability of DNA functionalized gold nanoparticles, Bioconjugate Chem., 24:1790-7 (2013).
Liu et al., Membrane anchored immunostimulatory oligonucleotides for in vivo cell modification and localized immunotherapy. Angew Chem Int Ed Engl. Jul. 25, 2011;50(31):7052-5. doi: 10.1002/anie.201101266. Epub Jun. 17, 2011.
Liu, J. et al., Silica Nanoparticle Supported Lipid Bilayers for Gene Delivery, Chem. Commun., 2009, 5100-5102.
Ljubimova et al., Nanoconjugate based on polymalic acid for tumor targeting. Chem Biol Interact. Jan. 30, 2008;171(2):195-203. Epub Feb. 8, 2007.
Luthi et al., Nanotechnology for synthetic high-density lipoproteins. Trens Mol Med. Dec. 2010;16(12):553-60. doi: 10.1016/j.molmed. 2010.10.006. Epub Nov. 17, 2010.
Lytton-Jean et al., A thermodynamic investigation into the binding properties of DNA functionalized gold nanoparticle probes and molecular fluorophore probes. J Am Chem Soc. Sep. 21, 2005;127(37):12754-5.
Lytton-Jean et al., Highly Cooperative Behavior of Peptide Nucleic Acid-Linked DNA-Modified Gold-Nanoparticle and Comb-Polymer Aggregates, Advanced Materials, 21: 706 (2009).
Martin et al., Ein neur Zugang zu 2'-O-alkylribonucleosiden and Eigenschaften deren oligonucleotide Hely, Chim. Acta, 78:486-504 (1995).
Massich et al., Regulating immune response using polyvalent nucleic acid-gold nanoparticle conjugates. Mol Pharm. Nov.-Dec. 2009;6(6):1934-40.
McAllister et al., Polymeric nanogels produced via inverse microemulsion polymerization as potential gene and antisense delivery agents, J. Am. Chem. Soc., 124:15198 (2002).
McKay et al., Characterization of a potent and specific class of antisense oligonucleotide inhibitor of human protein kinase C-alpha expression. J Biol Chem. Jan. 15, 1999;274(3):1715-22.
McMahon et al., Biomimetic high density lipoprotein nanoparticles for nucleic acid delivery. Nano Lett. Mar. 9, 2011;11(3):1208-14. doi: 10.1021/nl1041947. Epub Feb. 14, 2011.
Medintz et al., A reactive peptidic linker for self-assembling hybrid quantum dot-DNA bioconjugates. Nano Lett. Jun. 2007;7(6):1741-8. Epub May 26, 2007.
Monia et al., Nuclease resistance and antisense activity of modified oligonucleotides targeted to Ha-ras. J Biol Chem. Jun. 14, 1996;271(24):14533-40.
Munde et al., Induced fit conformational changes of a "reversed amidine" heterocycle: optimized interactions in a DNA minor groove complex. J Am Chem Soc. May 2, 2007;129(17):5688-98. Epub Apr. 11, 2007.
Neeper et al., Cloning and expression of a cell surface receptor for advanced glycosylation end products of proteins. J Biol Chem. Jul. 25, 1992;267(21):14998-5004.
Niemeyer et al., "Bifunctional DNA-Gold Nanoparticle Conjugates as Building Blocks for the Self-Assembly of Cross-Linked Particle Layers," Biochemical and Biophysical Research Communications, 2003, 311 (4), 995-999.
No Author Listed Spacer 18 (Hexathylene glycol) Oligonucleotide Modification. BioSynthesis. Last accessed Nov. 7, 2019 via https://www.biosyn.com/oligonucleotideproduct/spacer-18-heg-oligonucleotide-modification.aspx. 3 pages.
No Author Listed Spacer 18 (hexathyleneglycol) GeneLink. Last accessed Nov. 7, 2019 via http://genelink.com/newsite/products/mod_detail.asp?modid=19. 2 pages.
Pan et al., Dendrimer-Modified Magnetic Nanoparticles Enhance Efficiency of Gene Delivery System. Cancer Res. 2007;67:8156-8163.
Patel et al., Peptide antisense nanoparticles. Proc Natl Acad Sci U S A. Nov. 11, 2008;105(45):17222-6. doi: 10.1073/pnas.0801609105.
Patel et al., Scavenger receptors mediate cellular uptake of polyvalent oligonucleotide-functionalized gold nanoparticles, Bioconj. Chem., 21:2250 (2010).
Paul, New Way to Kill Lymphoma without Chemotherapy uses Golden Nanoparticles. Feinberg School of Medicine: Northwestern University. Jan. 22, 2013. 4 pages. ww.feinberg.northwestern.edu/news/2013/01/lymphoma_nanoparticales.html.
Peter et al., Characterization of suppressive oligodeoxynucleotides that inhibit Toll-like receptor-9-mediated activation of innate immunity. Immunology. Jan. 2008;123(1):118-28. Epub Oct. 23, 2007.
Prigodich et al., Nano-flares for mRNA regulation and detection, ACS Nano, 3:2147 (2009).
Qin et al., Significantly improved analytical sensitivity of lateral flow immunoassays by using thermal contrast. Angew Chem Int Ed Engl. Apr. 27, 2012;51(18):4358-61. doi:10.1002/anie.201200997. Epub Mar. 23, 2012.
Ramos-Casals et al., Autoimmune diseases induced by TNF-targeted therapies: analysis of 233 cases. Medicine (Baltimore). Jul. 2007;86(4):242-51.

(56) References Cited

OTHER PUBLICATIONS

Rana et al., Monolayer coated gold nanoparticles for delivery applications. Adv Drug Deliv Rev. Feb. 2012;64(2):200-16. doi: 10.1016/j.addr.2011.08.006. Epub Sep. 6, 2011.
Rosenzweig et al., Self-assembly of a four-helix bundle on a DNA quadruplex. Angew Chem Int Ed Engl. 2009;48(15):2749-51. doi: 10.1002/anie.200804849.
Rosi et al., Oligonucleotide-modified gold nanoparticles for intracellular gene regulation. Science. May 19, 2006;312(5776):1027-30.
Rush et al., Intracellular mRNA regulation with self-assembled locked nucleic acid polymer nanoparticles. J Am Chem Soc. May 28, 2014;136(21):7615-8. doi: 10.1021/ja503598z. Epub May 14, 2014.
Schwab et al., An approach for new anticancer drugs: Oncogene-targered antisense DNA. Ann Oncol. 1994;5(Suppl4):S55-8.
Seferos et al., Locked nucleic acid-nanoparticle conjugates, Chem. Bio. Chem., 8:1230 (2007).
Seferos et al., Polyvalent DNA nanoparticle conjugates stabilize nucleic acids. Nano Lett. Jan. 2009;9(1):308-11.
Shahzad et al., Targeted delivery of small interfering RNA using reconstituted high-density lipoprotein nanoparticles. Neoplasia. Apr. 2011;13(4):309-19.
Stunz et al., Inhibitory oligonucleotides specifically block effects of stimulatory CpG oligonucleotides in B cells. Eur J Immunol. May 2002;32(5):1212-22.
Suga et al., Conformational change of single-stranded RNAs induced by liposome binding. Nucleic Acids Res. Nov. 1, 2011;39(20):8891-900. doi: 10.1093/nar/gkr568. Epub Jul. 23, 2011.
Tiwari et al., Functionalized gold nanoparticles and their biomedical applications. Nanomaterials. 2011;1:31-63. doi: 10.3390/nano1010031.
Tripathy et al., High Density Lipoprotein Nanoparticles Deliver RNAi to Endothelial Cells to Inhibit Angiogenesis. Part Part Syst Charact. Nov. 1, 2014;31(11):1141-1150.
Vickers et al., . MicroRNAs are transported in plasma and delivered to recipient cells by highdensity; lipoproteins. Nat Cell Biol. Apr. 2011;13(4):423-33. doi: 10.1038/ncb2210. Epub 2011; Mar. 20. Erratum in: Nat Cell Biol. Jan. 2015;17(1):104.
Vorobjev et al., Nuclease resistance and RNase H sensitivity of oligonucleotides bridged by oligomethylenediol and oligoethylene glycol linkers. Antisense Nucleic Acid Drug Dev. Apr. 2001;11(2):77-85.
Whitehead et al., Knocking down barriers: advances in siRNA delivery, Nat. Rev. Drug. Discov., 8:129 (2009).
Wilton et al. Antisense oligonucleotide-induced exon skipping across the human dystrophin gene transcript. Mol Ther. Jul. 2007; 15(7):1288-96. Epub Feb. 6, 2007.
Wolfrum et al., Mechanisms and optimization of in vivo delivery of lipophilic siRNAs. Nat Biotechnol. Oct. 2007;25(10):1149-57. Epub Sep. 16, 2007.
Xiao et al., Mannosylated bioreducible nanoparticle-mediated macrophage-specific TNF-? RNA interference for IBD therapy. Biomaterials. Oct. 2013;34(30):7471-82. doi: 10.1016/j.biomaterials.2013.06.008. Epub Jun. 29, 2013.
Yang et al., Inhibition of a C-rich oligodeoxynucleotide on activation of immune cells in vitro and enhancement of antibody response in mice. Immunology. Dec. 2010;131(4):501-12. doi: 10.1111/j.1365-2567.2010.03322.x.
Yin et al., Supramolecular self-assembled nanoparticles mediate oral delivery of therapeutic TNF-? siRNA against systemic inflammation. Angew Chem Int Ed Engl. May 27, 2013;52(22):5757-61. doi: 10.1002/anie.201209991. Epub Apr. 22, 2013.
Young et al., Hollow spherical nucleic acids for intracellular gene regulation based upon biocompatible silica shells, Nano Lett., 12:3867 (2012).
Zhang et al., Antibody-linked spherical nucleic acids for cellular targeting, J. Am. Chem. Soc., 134:16488-91 (2012).
Zhang et al., Cationic lipids and polymers mediated vectors for delivery of siRNA. J Control Release. Oct. 18, 2007;123(1):1-10. Epub Aug. 7, 2007. Review.
Zhang et al., Nanopod formation through gold nanoparticle templated and catalyzed cross-linking of polymers bearing pendant propargyl ethers. J Am Chem Soc. Nov. 3, 2010;132(43):15151-3.
Zhang et al., TLR9-mediated siRNA delivery for targeting of normal and malignant human hematopoietic cells in vivo. Blood. Feb. 21, 2013;121(8):1304-15. doi: 10.1182/blood-2012-07-442590. Epub Jan. 3, 2013.
Zheng et al., Topical delivery of siRNA-based spherical nucleic acid nanoparticle conjugates for gene regulation. Proc Natl Acad Sci U S A. Jul. 24, 2012;109(30):11975-80. doi: 10.1073/pnas.1118425109. Epub Jul. 6, 2012.
Agrawal et al., Antisence therapeutics: Is it as simple as complementary base recognition? Mol. Med. Today. 2000; 6: 72-81.
Aynie et al., Spongelike alginate nanoparticles as a new potential system for the delivery of antisense oligonucleotides. Antisense Nucl. Acid Drug Dev. 1999; 9: 301-12.
Berton et al., Highly loaded nanoparticulate carrier using an hydrophobic antisense oligonucleotide complex. Eur. J. Pharma. Sci. 1999;9:163-70.
Crooke et al., Progress in antisense technology. Ann. Rev. Med. 2004;55: 61-95.
Demesmaeker et al., Antisense oligonucleotides. Acc. Chem. Res. 1995;28(9): 366-74.
D'ydewalle et al., The Antisense Transcript SMN-AS1 Regulates SMN Expression and is a Novel Therapeutic Target for Spinal Muscular Atrophy. Neuron. 2017;93(1):66-79.
Hamilton et al., A species of small antisense RNA in post-transcriptional gene silencing in plants. Science. 1999;286: 950-2.
Jason et al., Toxicology of antisense therapeutics. Toxicol. Appl. Pharmacol. 2004;201(1): 66-83.
Jeong et al., Novel intracellular delivery system of antisense oligonucleotide by self-assembled hybrid micelles composed of DNA/PEG conjugate and cationic fusogenic peptide. Bioconjugate Chem. 2003;14: 473-9.
Kaczmarek et al., 2,-Linking of lipids and other functions to uridine through 1,2,3-triazoles and membrane anchoring of the amphiphilic products. Eur J Org Chem. Mar. 1, 2010;2010(8):1579-86. DOI: 10.1002/ejoc.200901073.
Lebedeva et al., Antisense oligonucleotides: Promise and reality. Annu. Rev. Pharmacol. Toxicol. 2001;41: 403-19.
Li et al., Targeted delivery of antisense oligodeoxynucleotide and small interference RNA into lung cancer cells. Mol Pharm. Sep.-Oct. 2006;3(5):579-88. doi: 10.1021/mp060039w. Publication Date:Jul. 12, 2006.
McManus et al., Gene silencing in mammals by small interfering RNAs. Nat. Rev. Genet. 2002;3(10): 737-47.
Mendell, MicroRNAs: critical regulators of development, cellular physiology and malignancy. Cell Cycle. 2005;4(9):1179-84.
Miller et al., Antisense oligonucleotides: Strategies for delivery. PSTT. 1998;1(9): 377-86.
Nitin, et al. Oligonucleotide-Coated Metallic Nanoparticles as a Flexible Platform for Molecular Imaging Agents. Bioconjugate Chem. 2007;18:2090-2096.
Opalinska et al., Nucleic-acid therapeutics: basic principles and recent applications. Nat. Rev. Drug Discov. 2002;1: 503-14.
Osman et al., Morpholino antisense oligonucleotides targeting intronic repressor Element1 improve phenotype in SMA mouse models. Human Molecular Genetics. 2014;23(18):4832-45.
Ozpolat et al., Nanomedicine based approaches for the delivery of siRNA in cancer. J. Intern. Med. 2010;267(1):44-53.
Pao et al., Dual Masking of Specific Negative Splicing Regulatory Elements Resulted in Maximal Exon 7 Inclusion of SMN2 Gene. Molecular Therapy. 2014;22(4):854-61.
Patil et al., DNA-based therapeutics and DNA delivery systems: a comprehensive review. AAPS J., 2005;7(1): E61-77.
Schifferlers et al., Cancer siRNA therapy by tumor selective delivery with ligand-targeted sterically stabilized nanoparticle. Nucl. Acid Res., 2004;32(19): e149.
Sharma et al., Targeting mitogen-activated protein kinase/extracellular signal-regulated kinase kinase in the mutant (V600E) B-Raf signaling cascade effectively inhibits melanoma lung metastases. Cancer Res., 2006;66: 8200-9.

(56) References Cited

OTHER PUBLICATIONS

Sharp et al., RNA interference—2001. Genes Dev., 2001;15: 485-90.
Shu et al., Gradient cross-linked biodegradable polyelectrolyte nanocapsules for intracellular protein drug delivery. Biomaterials, 2010;31 (23):6039-49.
Stahl et al., Deregulated Akt3 activity promotes development of malignant melanoma. Cancer Res., 2004;64: 7002-10.
Tondelli, et al., Highly efficient cellular uptake of c-myb antisense oligonucleotides through specifically designed polymeric nanospheres. Nucl. Acids Res. 1998;26:5425-5431.
Wagner et al., Gene inhibition using antisense oligodeoxynucleotides. Nature, 1994;372: 333-5.
Yang et al., Evidence that processed small dsRNAs may mediate sequence-specific mRNA degradation during RNAi in *Drosophila* embryos. Curr. Biol., 2000;10: 1191-200.
Zamore et al., RNAi: Double-Stranded RNA Directs the ATP-Dependent Cleavage of mRNA at 21 to 23 Nucleotide Intervals. Cell. 2000;101:25-33.
Zimmer, Antisense oligonucleotide delivery with polyhexylcyanoacrylate nanoparticles as carriers. Methods, 1999;18: 286-95.
U.S. Appl. No. 16/772,551 filed Jun. 12, 2020, Mirkin et al.
[No Author Listed] Modern Pharmaceutical Design. 2006. Chapter 5. p. 273. English language summary. 2 pages.
Dokka et al., Dermal delivery of topically applied oligonucleotides via follicular transport in mouse skin. J Invest Dermatol. 2005;124(5):971-975. doi: 10.1111/j.0022-202X.2005.23672.x.
Holen et al., Positional effects of short interfering RNAs targeting the human coagulation trigger tissue factor. Nucl. Acids Res. 2002;30: 1757-66.
Hong et al., Directed Assembly of Nucleic Acid-Based Polymeric Nanoparticles from Molecular Tetravalent Cores, *J. Am. Chem. Soc.* 137:8184-91 (2015).
Hsu et al., Delivery of siRNA and other macromolecules into skin and cells using a peptide enhancer. Proc Natl Acad Sci U S A. 2011;108(38):15816-15821. doi:10.1073/pnas.1016152108.
Leachman et al., Therapeutic siRNAs for dominant genetic skin disorders including pachyonychia congenita. J Dermatol Sci. 2008;51(3):151-157. doi:10.1016/j.jdermsci.2008.04.003.
Massich et al., Cellular response of polyvalent oligonucleotide-gold nanoparticle conjugates, ACS Nano. 4:5641-6 (2010).
Rubenstein et al., Antisense oligonucleotide intralesional therapy for human PC-3 prostate tumors carried in athymic nude mice. J Surg Oncol. Jul. 1996;62(3):194-200. doi: 10.1002/(SICI)1096-9098(199607)62:3<194::AID-JSO9>3.0.CO;2-2.
Tran et al., Targeting V600EB-Raf and Akt3 using nanoliposomal-small interfering RNA inhibits cutaneous melanocytic lesion development. Cancer Res. Sep. 15, 2008;68(18):7638-49. doi: 10.1158/0008-5472.CAN-07-6614.
Wang et al., Co-delivery of drugs and DNA from cationic core-shell nanoparticles self-assembled from a biodegradable copolymer. Nat Mater. Oct. 2006;5(10):791-6. doi: 10.1038/nmat1737. Epub Sep. 24, 2006. PMID: 16998471.
Watson et al., DNA-block copolymer conjugates, *J. Am. Chem. Soc.* 123:5592-3 (2001).
Centa et al., Therapeutic efficacy of antisense oligonucleotides in mouse models of CLN3 Batten disease. Nat Med. Sep. 2020;26(9):1444-1451. doi: 10.1038/s41591-020-0986-1. Epub Jul. 27, 2020.
Dunn et al., Reductively responsive siRNA-conjugated hydrogel nanoparticles for gene silencing. J Am Chem Soc. May 2, 2012;134(17):7423-30. Doi: 10.1021/ja300174v. Epub Apr. 19, 2012. Author Manuscript, 18 pages.
Dutta et al., Templated Self-Assembly of a Covalent Polymer Network for Intracellular Protein Delivery and Traceless Release. J Am Chem Soc. Apr. 26, 2017;139(16):5676-5679. Doi: 10.1021/jacs.7b01214. Epub Apr. 13, 2017. Author Manuscript, 13 pages.
Hirosue et al., Antigen delivery to dendritic cells by poly(propylene sulfide) nanoparticles with disulfide conjugated peptides: Cross-presentation and T cell activation. Vaccine. Nov. 23, 2010;28(50):7897-906. Doi: 10.1016/j.vaccine.2010.09.077. Epub Oct. 8, 2010.
Liu et al., Structure-based programming of lymph-node targeting in molecular vaccines. Nature. Mar. 27, 2014;507(7493):519-22. Doi: 10.1038/nature12978. Epub Feb. 16, 2014. Author Manuscript, 23 pages.
Wang et al., SPINK5 knockdown in organotypic human skin culture as a model system for Netherton syndrome: effect of genetic inhibition of serine proteases kallikrein 5 and kallikrein 7. Exp Dermatol. Jul. 2014;23(7):524-6. doi: 10.1111/exd.12451.
Zammarchi et al., Antitumorigenic potential of STAT3 alternative splicing modulation. Proc Natl Acad Sci U S A. Oct. 25, 2011;108(43):17779-84. doi: 10.1073/pnas.1108482108. Epub Oct. 17, 2011.
U.S. Appl. No. 15/527,840, filed May 18, 2017, Mirkin et al.
U.S. Appl. No. 16/611,502, filed Nov. 7, 2019, Mirkin et al.
U.S. Appl. No. 16/611,548, filed Nov. 7, 2019, Mirkin et al.
U.S. Appl. No. 16/160,196, filed Oct. 15, 2018, Mirkin et al.
U.S. Appl. No. 16/328,025, filed Feb. 25, 2019, Mirkin et al.
U.S. Appl. No. 17/011,658, filed Sep. 3, 2020, Mirkin et al.
Condori et al., Enzyme replacement for GM1-gangliosidosis: Uptake, lysosomal activation, and cellular disease correction using a novel ß-galactosidase:RTB lectin fusion. Mol Genet Metab. Feb. 2016;117(2):199-209. doi: 10.1016/j.ymgme.2015.12.002. Epub Dec. 8, 2015.
Ming et al., Bioconjugates for targeted delivery of therapeutic oligonucleotides. Adv Drug Deliv Rev. Jun. 29, 2015;87:81-9. doi: 10.1016/j.addr.2015.02.002. Epub Feb. 15, 2015.
Nandi et al., Role of Catalase in Oxidative Stress- and Age-Associated Degenerative Diseases. Oxid Med Cell Longev. Nov. 11, 2019;2019:9613090. doi: 10.1155/2019/9613090.
Rosado et al., Enzyme replacement therapy for primary adult lactase deficiency. Effective reduction of lactose malabsorption and milk intolerance by direct addition of beta-galactosidase to milk at mealtime. Gastroenterology. Nov. 1984;87(5):1072-82.
Singh et al., Synthesis of gold, silver and their alloy nanoparticles using bovine serum albumin as foaming and stabilizing agent. J Mater Chem. Dec. 2005;15(48):5115-5121. doi:10.1039/b510398c.
Watts et al., Silencing disease genes in the laboratory and the clinic. J Pathol. Jan. 2012;226(2):365-79. doi: 10.1002/path.2993. Epub Nov. 9, 2011.
Hammer et al., Cleavable carbamate linkers for controlled protein delivery from hydrogels. J Control Release. Jun. 10, 2014;183:67-76. doi: 10.1016/j.jconrel.2014.03.031. Epub Mar. 25, 2014.

* cited by examiner

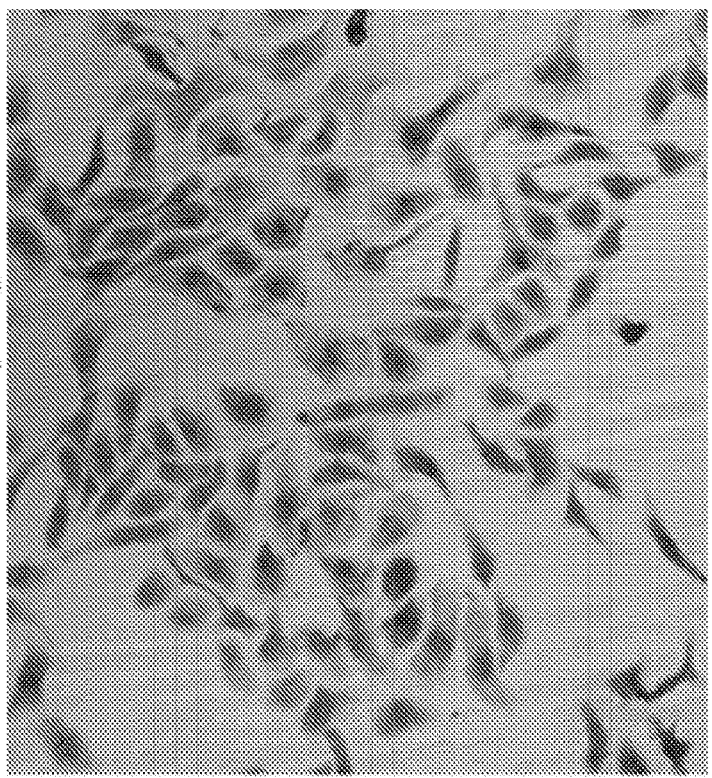
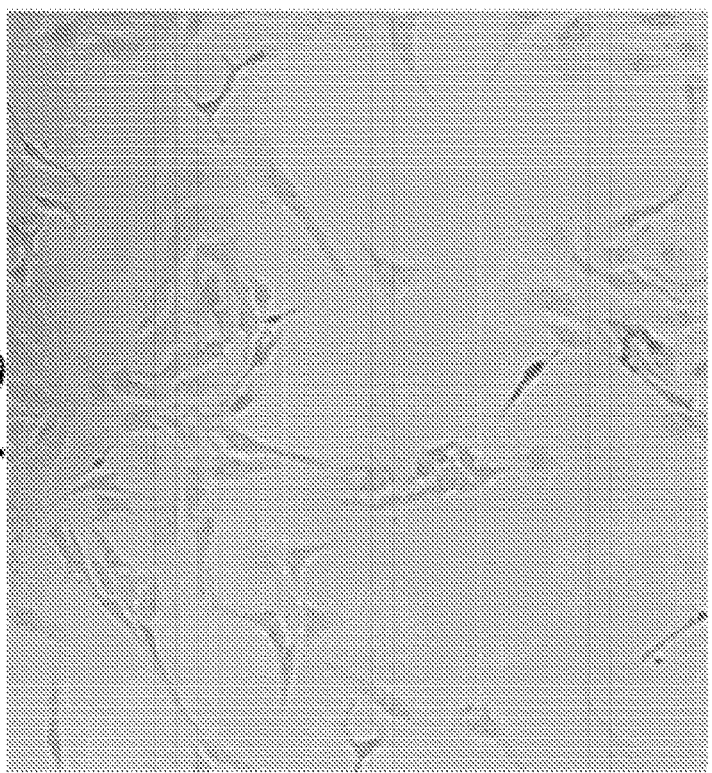
Figure 13

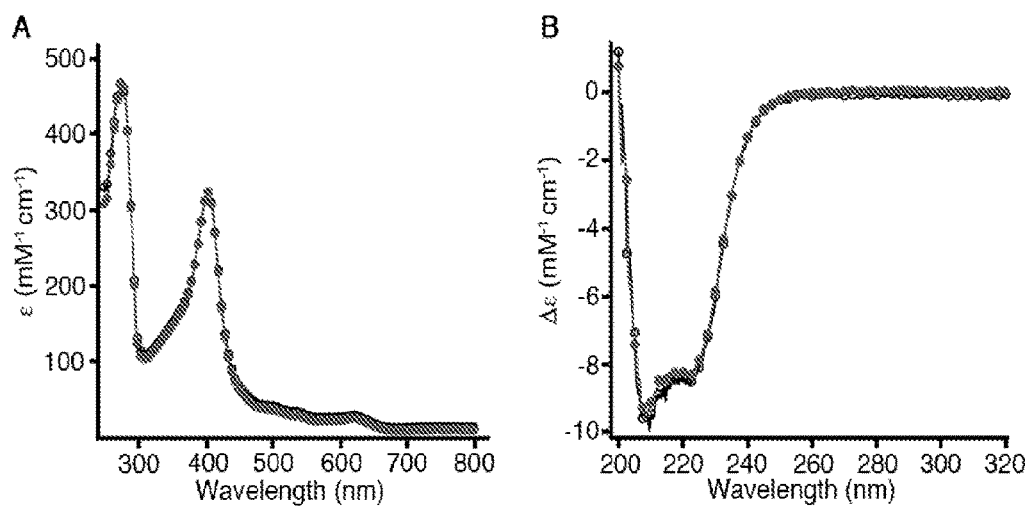
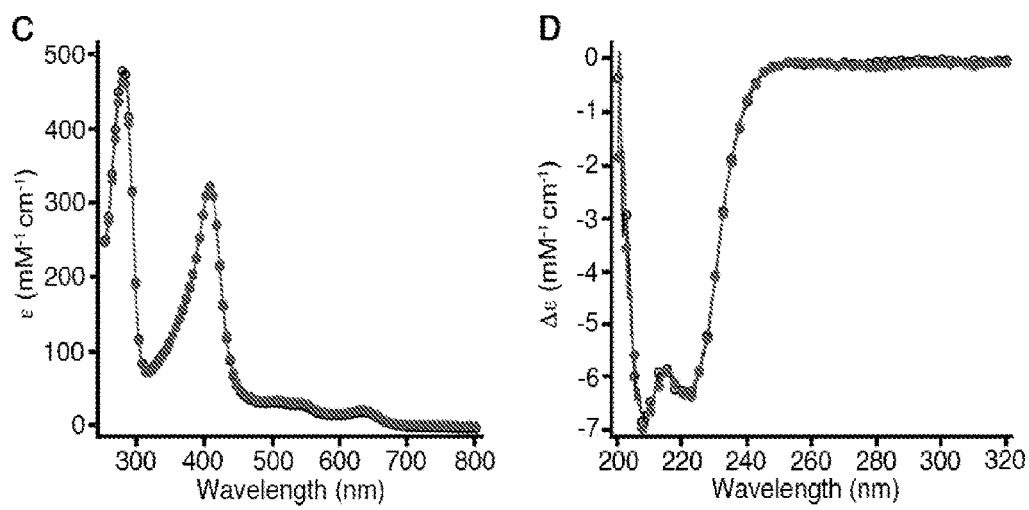
Figure 18

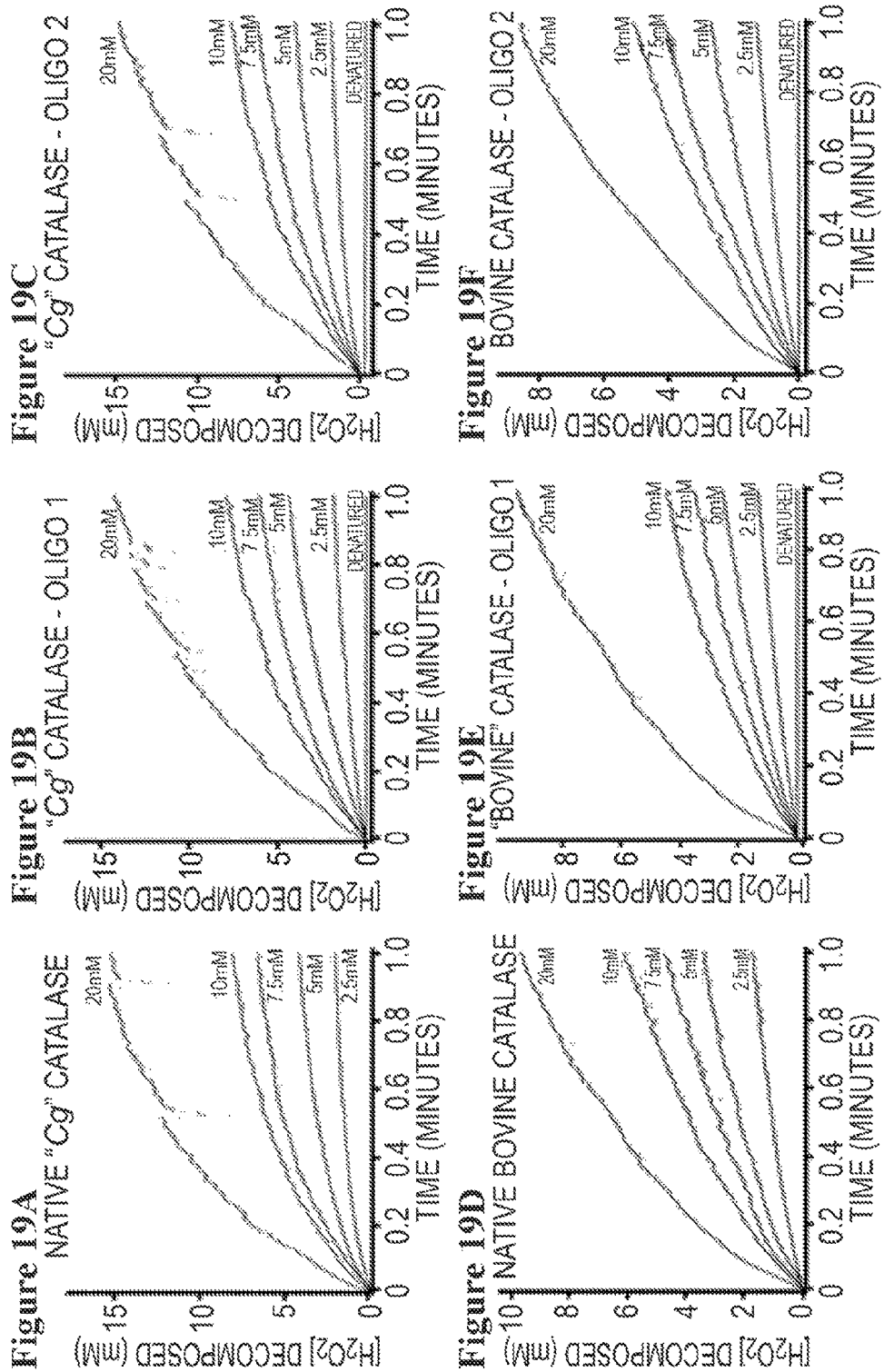

Figure 19H
SUMMARY OF STANDARD VELOCITY CONSTANTS FOR H2O2 DECOMPOSITION
| PROTEIN | $K_S$ (M$^{-1}$ s$^{-1}$ X 10$^7$) |
|---|---|
| NATIVE "Cg" CATALASE | 3.4 ± 0.2 |
| "Cg" CATALASE OLIGONUCLEOTIDE 1 | 2.4 ± 0.1 |
| "Cg" CATALASE OLIGONUCLEOTIDE 2 | 2.5 ± 0.10 |
| NATIVE BOVINE CATALASE | 1.8 ± 0.1 |
| BOVINE CATALASE - OLIGONUCLEOTIDE 1 | 1.19 ± 0.03 |
| BOVINE CATALASE - OLIGONUCLEOTIDE 2 | 1.38 ± 0.06 |
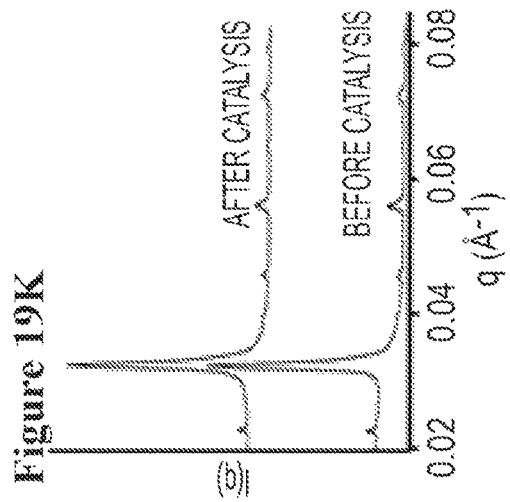
Figure 19K
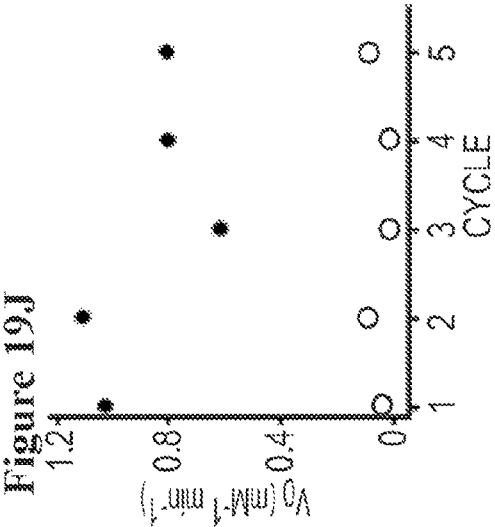
Figure 19J
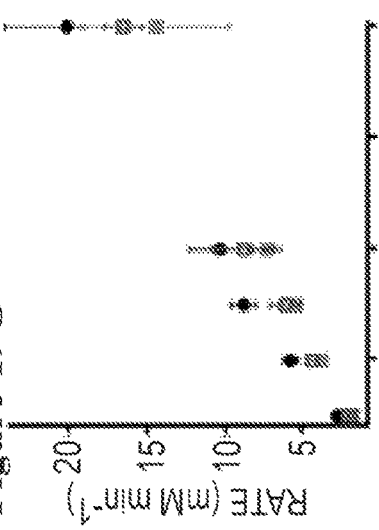
Figure 19G
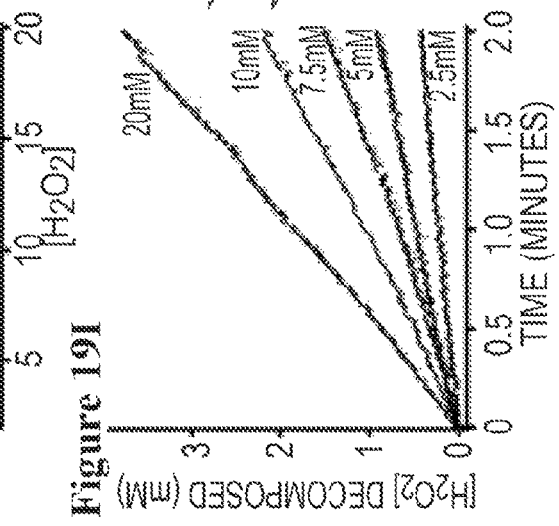
Figure 19I

PROTEIN/OLIGONUCLEOTIDE CORE-SHELL NANOPARTICLE THERAPEUTICS

CROSS REFERENCE TO RELATED APPLICATIONS

This application claims the priority benefit under 35 U.S.C. § 119(e) of U.S. Provisional Application No. 62/039,340, filed Aug. 19, 2014, U.S. Provisional Application No. 62/039,608, filed Aug. 20, 2014 and U.S. Provisional Application No. 62/137,183, filed Mar. 23, 2015, the disclosures of which are incorporated herein by reference in their entirety.

STATEMENT OF GOVERNMENT SUPPORT

This application is a U.S. National Phase of PCT/US2015/045971 filed Aug. 19, 2015, which claims the priority benefit under 35 U.S.C. § 119(e) of U.S. Provisional Application No. 62/039,340, filed Aug. 19, 2014, U.S. Provisional Application No. 62/039,608, filed Aug. 20, 2014 and U.S. Provisional Application No. 62/137,183, filed Mar. 23, 2015, the disclosures of which are incorporated herein by reference in their entirety.

INCORPORATION BY REFERENCE OF MATERIAL SUBMITTED ELECTRONICALLY

This application contains, as a separate part of the disclosure, a Sequence Listing in computer-readable form which is incorporated by reference in its entirety and identified as follows: Filename: E060570000US02-SEQ-DQB.txt; 4,735 bytes, created Dec. 5, 2024.

BACKGROUND

Proteins represent a rapidly expanding class of therapeutics, with potential applications in drug delivery, drug targeting, cancer therapy and enzyme replacement therapy. However, issues such as poor cellular uptake, activation of the innate immune response, poor bioavailability, degradation by cellular proteases, or aggregation and inactivation upon prolonged storage currently limit the therapeutic potential of proteins.

DNA-mediated assembly strategies [Mirkin et al., Nature 382(6592): 607-609 (1996); Seeman, Mol Biotechnol 37(3): 246-257 (2007)] that take advantage of rigid building blocks, functionalized with oriented oligonucleotides to create entities with well-defined "valencies," have emerged as powerful new ways for programming the formation of crystalline materials [Park et al., Nature 451(7178): 553-556 (2008); Nykypanchuk et al., Nature 451(7178): 549-552 (2008)]. With such methods, one can make architectures with well-defined lattice parameters [Hill et al., Nano Lett 8(8): 2341-2344 (2008); Macfarlane et al., Angew Chem Int Ed Engl 49(27): 4589-4592 (2010); Macfarlane et al., Science 334(6053): 204-208 (2011); Xiong et al., Phys Rev Lett 102(1): 015504 (2009); Auyeung et al., Nat Nanotechnol 7(1): 24-28 (2012); Auyeung et al., Nature 505(7481): 73-77 (2014); Zhang et al., Nat Mater 12(8): 741-746 (2013)], symmetries [Park et al., Nature 451(7178): 553-556 (2008); Macfarlane et al., Science 334(6053): 204-208 (2011); Auyeung et al., Nat Nanotechnol 7(1): 24-28 (2012); Zhang et al., Nat Mater 12(8): 741-746 (2013)], and compositions [Auyeung et al., Nat Nanotechnol 7(1): 24-28 (2012); Zhang et al., Nat Mater 12(8): 741-746 (2013); Zhang et al., Nat Nanotechnol 8(11): 865-872 (2013)], but to date they have been confined primarily to the use of hard inorganic nanoparticles or highly branched pure nucleic acid materials [Seeman, Mol Biotechnol 37(3): 246-257 (2007); Winfree et al., Nature 394(6693): 539-544 (1998); Zheng et al., Nature 461(7260): 74-77 (2009)]. In contrast, nature's most powerful and versatile nanostructured building blocks are proteins, and are used to effect the vast majority of processes in living systems [Mann, Angew Chem Int Ed 47(29): 5306-5320 (2008)]. Unlike most inorganic nanoparticle systems, proteins can be made in pure and perfectly monodisperse form, making them ideal synthons for supramolecular assemblies. However, the ability to engineer lattices composed of multiple proteins, or of proteins and inorganic nanomaterials, has been limited, and the choice of protein building blocks is often restricted by structural constraints, which limits the catalytic functionalities that can be incorporated into these structures. Currently, the primary methods for making protein lattices have relied on the use of natural protein-protein interactions [Liljestrom et al., Nat Commun 5: 4445 (2014)], interactions between proteins and ligands on the surfaces of inorganic nanoparticles (NPs) [Liljestrom et al., Nat Commun 5: 4445 (2014); Kostiainen et al., Nat Nanotechnol 8(1): 52-56 (2013)], metal coordination chemistry [Brodin et al., Nat Chem 4(5): 375-382 (2012)], small molecule ligand-protein interactions [Dotan et al., Angew Chem Int Ed 38(16): 2363-2366 (1999); Ringler et al., Science 302(5642): 106-109 (2003); Sakai et al., Nat Commun 5: 4634 (2014); Oohora et al., Chem Commun 48(96): 11714-11726 (2012)], genetically fusing protein complexes with specific symmetries [Padilla et al., Proc Natl Acad Sci USA 98(5): 2217-2221 (2001); Sinclair et al., Nat Nanotechnol 6(9): 558-562 (2010], or DNA-mediated assembly of viruses [Strable et al., Nano Lett 4(8): 1385-1389 (2004); Cigler et al., Nat Mater 9(11): 918-922 (2010)].

DNA-directed assembly has proven to be a powerful method for the construction of crystalline materials form nanoscale precursors. However, despite repeated demonstrations showing the utility of this approach, the systems studied have largely been limited to metallic nanoparticles.

SUMMARY OF THE INVENTION

To overcome the aforementioned issues, the present disclosure provides products and methods whereby the surface of a protein is chemically functionalized with a dense shell of oligonucleotides, generating a protein/DNA core-shell nanoparticle (NP). Protein/DNA core-shell nanoparticles consist of a protein core and a dense shell of oligonucleotides. These hybrid macromolecules can be used to construct crystalline materials from catalytically active proteins. Additionally, the strategy of DNA-templated protein crystallization can be used to assemble crystals suitable for protein structure determination by X-ray crystallography. It is contemplated herein that the dense and highly anionic surface imparted on the protein by the oligonucleotide shell prevents aggregation and unfolding of the functionalized proteins, and will also provide a barrier that limits degradation by cellular proteases. In analogy to other nanomaterials modified with a dense shell of nucleic acids, the modified proteins provided by the disclosure will efficiently enter cells and elicit a minimal immune response. Further, the protein-oligonucleotide conjugates function as dual-function therapeutics where the native chemical functionality of an enzyme and the gene regulation capability of the oligonucleotide shell each elicit a distinct therapeutic response.

The ability to predictably control the co-assembly of multiple nanoscale building blocks, especially those with disparate chemical and physical properties such as biomolecules and inorganic nanoparticles, has far-reaching implications in catalysis, sensing and photonics, but a generalizable strategy for engineering specific contacts between these particles is an outstanding challenge. This is especially true in the case of proteins, where the types of possible interparticle interactions are numerous, diverse, and complex. Herein, the concept of trading protein-protein interactions for DNA-DNA interactions is provided to direct the assembly of two nucleic-acid functionalized proteins with distinct surface chemistries into six unique lattices composed of catalytically active proteins, or of a combination of proteins and DNA-modified gold nanoparticles. The programmable nature of DNA-DNA interactions employed in this strategy allows for the control of lattice symmetries and unit cell constants, as well as the compositions and habit, of the resulting crystals. The disclosure provides a generalizable strategy for constructing a unique class of materials that take advantage of the diverse morphologies, surface chemistries and functionalities of proteins for assembling functional crystalline materials.

Accordingly, in various aspects the disclosure provides a method for effecting protein crystallization by trading protein-protein interactions for complementary oligonucleotide-oligonucleotide interactions. By using different proteins functionalized with the appropriate oligonucleotides, along with the design rules introduced for inorganic systems [Macfarlane et al., Angew Chem Int Ed Engl 49(27): 4589-4592 (2010); Macfarlane et al., Science 334(6053): 204-208 (2011); Macfarlane et al., Angew Chem Int Ed 52(22): 5688-5698 (2013)], the disclosure shows that different combinations of DNA-functionalized enzymes, and enzymes and inorganic nanoparticles, are assembled deliberately into preconceived lattices and, in some cases, well-defined crystal habits. Importantly, the enzymes retain their native structures and catalytic functionalities after extensive modification of their surfaces with DNA and assembly into crystalline superlattices. The disclosure demonstrates, inter alia, that DNA can be used for assembling many readily accessible functional proteins into ordered materials, regardless of their atomic compositions.

Disclosed herein is the synthesis of a class of protein-based materials composed of a protein core and a dense oligonucleotide shell. The oligonucleotide shell not only imparts stability on the enzyme core, but also serves as a universal scaffold to which additional oligonucleotides can be hybridized, ultimately providing DNA-directed assembly of proteins into crystalline materials. Compared to other approaches for programming the assembly of proteins into supramolecular structures, the DNA-templating strategy provided by the disclosure is, for example and without limitation, generalizable to any protein, does not require genetic manipulation of the protein core, and allows for the assembly of lattices with multiple components (e.g., multiple proteins or a combination of proteins and inorganic nanostructures) into materials with defined stoichiometries and relative orientations. It is expected that employing this approach with a wide range of proteins will lead to applications in catalysis and sensing, and serve as a strategy assembling protein crystals suitable for structure determination.

Thus, in some aspects the disclosure provides a core-shell nanoparticle, the core comprising a single protein, and the shell comprising a plurality of polynucleotides, the polynucleotides attached to the protein surface via covalent bonds. In various embodiments, the protein exhibits catalytic, signaling, therapeutic, or transport activity. In some embodiments, each polynucleotide of the plurality is the same. In further embodiments, at least two of the polynucleotides of the plurality are different.

In some embodiments, the density of polynucleotides on the protein surface is about 2 pmol/cm$^2$ to about 200 pmol/cm$^2$. In further embodiments, the density of polynucleotides on the protein surface is about 10 pmol/cm$^2$. In still further embodiments, the density of polynucleotides on the protein surface is about 100 pmol/cm$^2$.

In some embodiments, a core-shell nanoparticle of the disclosure further comprises an additional agent covalently or non-covalently attached to at least one of the plurality of polynucleotides. In various embodiments, the additional agent is a polynucleotide, a peptide, a protein, a phospholipid, an oligosaccharide, a metal complex, a small molecule, a therapeutic agent, a contrast agent or a combination thereof. In some embodiments, the additional agent is non-covalently attached to at least one of the plurality of polynucleotides through hybridization. In further embodiments, the additional agent is covalently associated with at least one of the plurality of polynucleotides.

The disclosure also provides embodiments wherein at least one polynucleotide of the shell is attached to the protein surface via a surface amino group of the protein. In some embodiments, the surface amino group is from a Lys residue.

In some embodiments, the at least one polynucleotide is attached via a triazole linkage formed from reaction of (a) an azide moiety attached to the surface amino group and (b) an alkyne functional group on the at least one polynucleotide.

In additional embodiments, the at least one polynucleotide is attached to the protein surface is via a linkage as shown in Formula (I), (II), or both:

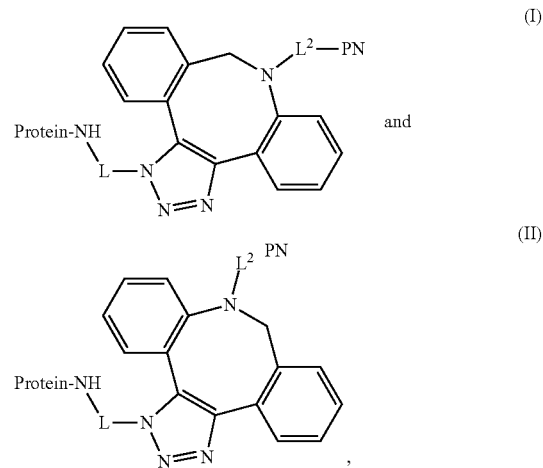

L and L$^2$ are each independently selected from C$_{1-10}$ alkylene, —C(O)—C$_{1-10}$ alkylene-Y—, and —C(O)—C$_{1-10}$ alkylene-Y—C$_{1-10}$ alkylene-(OCH$_2$CH$_2$)$_m$—Y—;

each Y is independently selected from the group consisting of a bond, C(O), O, NH, C(O)NH, and NHC(O);

m is 0, 1, 2, 3, 4, or 5; and

PN is the at least one polynucleotide.

In still further embodiments, at least one polynucleotide of the shell is attached to the protein surface via a surface carboxyl group of the protein. In some embodiments, at least one polynucleotide of the shell is attached to the protein surface via a surface thiol group of the protein. In additional embodiments, at least one polynucleotide of the shell is sufficiently complementary to a target polynucleotide to hybridize to and inhibit the expression of the target polynucleotide.

The additional agent, in some embodiments, is a polynucleotide that is sufficiently complementary to a target polynucleotide to hybridize to and inhibit the expression of the target polynucleotide.

In some aspects, the disclosure provides a composition comprising a plurality of the core-shell nanoparticles of any one of the preceding claims. In some embodiments, the plurality of core-shell nanoparticles forms a crystalline structure.

In some embodiments, each core-shell nanoparticle comprises the same protein. In further embodiments, at least two core-shell nanoparticles comprise different proteins.

In additional embodiments, the composition further comprises a metallic nanoparticle. In various embodiments, the metallic nanoparticle comprises gold, silver, platinum, aluminum, palladium, copper, cobalt, indium, nickel, or a mixture thereof.

In further embodiments, the plurality of polynucleotides of a first core-shell nanoparticle have a polynucleotide sequence that is sufficiently complementary to a polynucleotide sequence of the plurality of polynucleotides of a second core-shell nanoparticle to hybridize and form a superlattice structure.

In further aspects of the disclosure, a method of catalyzing a reaction is provided comprising contacting reagents for the reaction with a composition of the disclosure, wherein contact between the reagents and the composition results in the reaction being catalyzed.

In additional aspects, the disclosure provides a method of detecting a target molecule comprising contacting the target molecule with a core-shell nanoparticle or a composition of the disclosure, wherein contact between the target molecule and the core-shell nanoparticle or the composition results in a detectable change. In some embodiments, the detecting is in vitro. In some embodiments, the detecting is in vivo.

In some aspects, a method of inhibiting expression of a gene product encoded by a target polynucleotide is provided, comprising contacting the target polynucleotide with a core-shell nanoparticle or a composition of the disclosure under conditions sufficient to inhibit expression of the gene product. In some embodiments, expression of the gene product is inhibited in vivo. In some embodiments, expression of the gene product is inhibited in vitro. In some embodiments, expression of the gene product is inhibited by at least about 5%.

In further aspects of the disclosure, a method of delivering a therapeutic protein to a cell is provided, comprising administering a core-shell nanoparticle or a composition of the disclosure to the cell, wherein the protein of the core-shell nanoparticle is the therapeutic protein. In some embodiments, the delivery is in vitro delivery. In some embodiments, the delivery is in vivo delivery.

In various embodiments, the cell is in a subject. In further embodiments, the subject is in need of the therapeutic protein.

In some embodiments of the disclosure, the method provides a reduced immunogenic response in the subject compared to administration of the therapeutic protein alone. In further embodiments, the method provides increased cellular uptake of the therapeutic protein compared to administration of the therapeutic protein alone.

In some aspects, the disclosure provides a method of preparing a core-shell nanoparticle comprising contacting a protein with a plurality of polynucleotides under conditions sufficient to covalently attach the plurality of polynucleotides to the surface of the protein.

In some embodiments, the protein has a structure:

Protein-X-L-N$_3$,

X is from a surface amino group, carboxylic group, or thiol group on the protein;

L is selected from $C_{1-10}$ alkylene, —Y—C(O)—$C_{1-10}$ alkylene-Y—, and —Y—C(O)—$C_{1-10}$ alkylene-Y—$C_{1-10}$ alkylene-(OCH$_2$CH$_2$)$_m$—Y—;

each Y is independently selected from the group consisting of a bond, C(O), O, NH, C(O)NH, and NHC(O); and m is 0, 1, 2, 3, 4, or 5.

In further embodiments, at least one polynucleotide has a structure:

Polynucleotide-L$^2$-X—≡—R;

L$^2$ is selected from $C_{1-10}$ alkylene, —C(O)—$C_{1-10}$ alkylene-Y—, and —C(O)—$C_{1-10}$ alkylene-Y—$C_{1-10}$ alkylene-(OCH$_2$CH$_2$)$_m$—Y—;

each Y is independently selected from the group consisting of a bond, C(O), O, NH, C(O)NH, and NHC(O);

m is 0, 1, 2, 3, 4, or 5; and

X is a bond and R is H or $C_{1-10}$ alkyl;

or X and R together with the carbons to which they are attached form a 8-10 membered carbocyclic or 8-10 membered heterocyclic group.

In still further embodiments, the at least one polynucleotide has a structure:

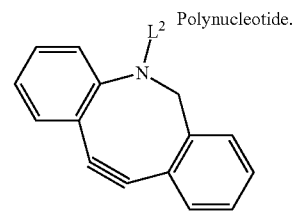

DESCRIPTION OF THE FIGURES

FIG. 6b) Photograph of DNA-labeled bovine catalase after the addition of self-complementary linkers. The unaggregated sample (right) shows that addition of a non-self-complementary linker does not result in aggregation. FIG. 6c) Thermally induced disassembly of protein aggregates followed by UV spectroscopy.

FIG. 7b) Photograph of a DNA-templated aggregate containing both bovine and Cg catalases that forms upon the addition of self-complementary linkers. FIG. 7c) Thermally induced disassembly of binary protein aggregates followed by UV spectroscopy. FIG. 7d) Photograph of a DNA-templated aggregate containing bovine catalase and AuNPs that forms upon the addition of linkers that are complementary to the linker on the other particle type. FIG. 7e) Thermally induced disassembly of binary protein AuNP aggregates followed by UV spectroscopy.

FIG. 8a) Depiction of a body-centered cubic (BCC) unit cell composed entirely of protein building blocks. FIG. 8b) Experimental (red) and theoretical (black) 1-D SAXS scattering profiles of BCC superlattices. FIG. 8c) Depiction of a BCC unit cell formed from a combination of protein and Au PAEs. FIG. 8d) 1-D SAXS scattering profile of binary Au-protein superlattices.

FIG. 13 shows the catalytic activity of Native (left) and DNA-functionalized (right) β-gal within transfected cells.

FIG. 14a) Cartoon depictions of bovine and Cg catalases showing their molecular topologies and the locations of surface-accessible amines. FIG. 14b) Scheme for the synthesis and assembly of DNA-functionalized catalases. Surface-accessible amines were modified with azides containing NHS and N3 moieties at opposing termini (i), after which the covalently attached azides were conjugated to two distinct 5'-DBCO-modified DNA strands via a copper-free "click chemistry" reaction (ii). Hybridization of linker strands to the DNA-functionalized proteins (iii) followed by mixing of proteins with complementary linkers (iv) results in the assembly of the proteins into BCC or CsCl-type unit cells. FIGS. 14c-e) Comparison of the hydrodynamic diameters of native (FIG. 14c), N3-functionalized (FIG. 14d), and DNA-functionalized (FIG. 14e) Cg catalases, as determined by DLS. (FIG. 14f) Comparison of the enzyme-catalyzed rates of the disproportionation of $H_2O_2$ as a function of substrate concentration by native (black circles), DNA-functionalized (red (strand 1) and blue (strand 2) squares), and crystalline (cyan triangles) Cg catalase. FIG. 14g) Thermal melting transition of DNA-templated aggregates composed of Cg catalase.

FIG. 15a) Cartoon depiction of DNA-functionalized Cg catalase showing the relative contributions of the DNA, protein, and linker to the hydrodynamic diameter of the conjugate. The linker region (cyan) is composed of a tetraethylene glycol spacer from the azide linker and a spacer between the DBCO and thymidine moieties of the DBCO dT synthetic phosphoramidite (inset). Two spacer 18 phosphoramidites were also included in the DNA design and are not depicted in the cartoon for clarity. FIGS. 15b-d) Dynamic light scattering (DLS) spectra of native (b), azide-functionalized (c), and DNA-functionalized (d) bovine catalases. FIG. 15e) Summary of the hydrodynamic diameters of bovine and Cg catalases, and their azide- and DNA-functionalized variants. Note that the distances in FIG. 15a are estimates based on the distance per base pair in the crystalline state and the linker adopting idealized bond distances and angles, as calculated by the ProDrug Server [Schuttelkopf et al., Acta Crystallogr D 60: 1355-1363 (2004)].

FIG. 16e) Summary of the extents of protein functionalization with azides and each oligonucleotide. The number of surface-accessible lysines was calculated from a surface representation of each protein generated in the Pymol Molecular Graphics System [The PyMOL Molecular Graphics System, Version 1.5.0.4 Schrödinger, LLC.]. The actual solvent accessibility of each amine varies, which likely explains why the observed yields are less than those that are theoretically possible. Nevertheless, the number of functionalized amines was highly reproducible over several labeling reactions (Between 15 and 16 for bovine catalase and 11 and 12 for Cg catalase). The apparent excess of DNA strands for Oligo 2 on bovine catalase is likely due to error in estimating the protein concentration and/or slight changes in the extinction of the DNA in the crowded environment on the protein's surface or uncertainties in the calculated extinction of the DNA.

FIGS. 18a-d show spectroscopic characterizations of the structure of bovine (FIGS. 18a and b) and "Cg" (FIGS. 18c and d) catalases before (open circles) and after (closed circles) functionalization with azide linkers. FIGS. 18a and c) UV-visible absorbance spectra of native and N3-functionalized bovine (FIG. 18a) and Cg (FIG. 18c) catalases. The nearly identical visible absorbance spectra of the N3-functionalized protein variants relative to the native enzymes confirms that the active site of the protein is largely intact after functionalization. The retention of 405:280 ratio confirms that heme loss does not occur during the functionalization procedure. FIGS. 18b and d) CD spectra of bovine (FIG. 18b) and Cg (FIG. 18d) catalases. The retention of the characteristic absorbance features and intensities confirm that the enzymes retain their secondary structures after functionalization with azides.

FIGS. 19a-k show catalytic decomposition of $H_2O_2$ by native catalases, DNA-functionalized catalases, and Cg catalase crystals. Changes in the absorbance at 240 nm after the addition of native (FIGS. 19a and d) or DNA-functionalized (FIGS. 19b-c and e-f) Cg (FIGS. 19a-c) and bovine (FIGS. 19d-f) catalases were converted to the concentration of $H_2O_2$ decomposed by dividing by the molar extinction coefficient of $H_2O_2$ (43 $M^{-1}$ $cm^{-1}$) and plotted as a function of time. The initial reaction rates for each $H_2O_2$ concentration were calculated and are plotted in FIG. 14f (Cg catalase) and 19g (bovine catalase). FIG. 19h) Summary of the velocity constants for the decomposition of $H_2O_2$ by each enzyme variant. FIG. 19i) Decomposition of $H_2O_2$ by Cg catalase crystals at various substrate concentrations. FIG. 19j) Recycling of enzyme crystals. Lower and upper dots correspond to the supernatant and pellet, respectively. FIG. 19k) Structure of protein crystals before (bottom) and after (top) 5 rounds of catalysis, centrifugation and resuspension.

FIG. 20g) Summary of the melting temperatures and full widths at half maximum of the first derivative of each melting curve.

FIG. 22d) A high magnification TEM image of a single Cg catalase crystal with clearly visible lattice planes demonstrating its single crystalline nature. Scale bars are 5 μm for (FIG. 22a) and (FIG. 22c), 500 nm for (FIGS. 22b) and 200 nm for (FIG. 22d).

DETAILED DESCRIPTION

Due to their unique structures and diverse catalytic functionalities, proteins represent a nearly limitless set of precursors for constructing functional supramolecular materials. However, programming the assembly of even a single protein into ordered superlattices is a difficult task, and a generalizable strategy for co-assembling multiple proteins with distinct surface chemistries, or proteins and inorganic nanoparticles, does not currently exist. Here, the high fidelity interactions characteristic of DNA-DNA "bonds" are employed to direct the assembly of, in various embodiments, two proteins into six unique superlattices composed of either a single protein, multiple proteins, or proteins and gold nanoparticles. Significantly, the DNA-functionalized proteins retain their native catalytic functionalities both in the solution and crystalline states.

Figure 24:
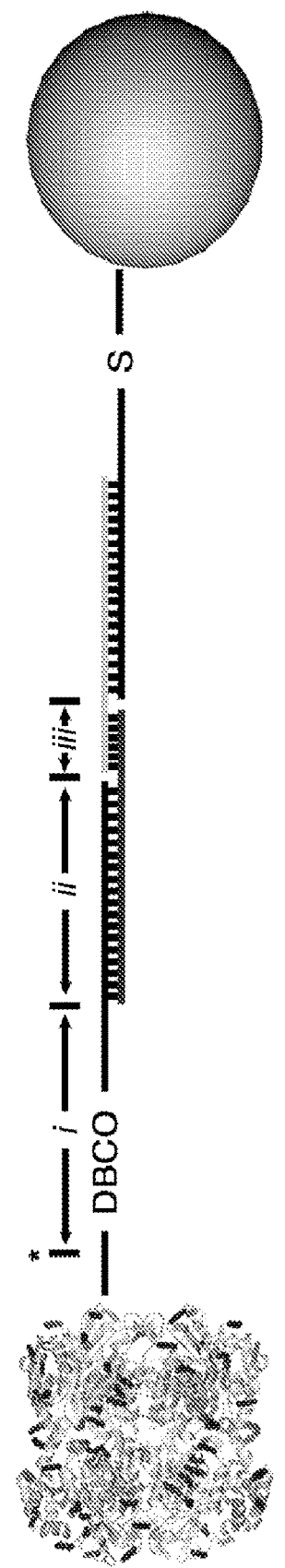
FIG. 24 is a scheme illustrating the DNA-mediated interactions between particles functionalized with complementary oligonucleotides. Each particle (protein=magenta cartoon and AuNP=gold sphere) is functionalized with an oligonucleotide that consists of a region (i) containing a chemically reactive moiety for particle attachment (thiol and DBCO moieties for AuNPs and proteins, respectively) and a short flexible region that consists of PEG spacers (Sp). These spacers, which are also included between the recognition and sticky end portions of the linker strands, are included to increase the flexibility of the DNA interconnects and promote the formation of high quality crystals. The flexible region is flanked by a recognition sequence (ii) that hybridizes to a complementary linker strand (blue or yellow). The terminus of each linker consists of a short sticky end (iii) that is complementary to the sticky end on the other particle type. Although only one protein-DNA or AuNP-DNA linkage is shown for clarity, the surface of the protein contains many potentially functionalizable lysine residues (blue sticks).

DNA-mediated nanoparticle (NP) assembly and crystallization [Mirkin et al., Nature 382(6592): 607-609 (1996); Park et al., Nature 451(7178): 553-556 (2008); Nykypanchuk et al., Nature 451(7178): 549-552 (2008)], requires that the surface of the component building blocks be modified with a dense monolayer of radially-oriented oligonucleotides. This architecture, also referred to as a programmable atom equivalent [Macfarlane et al., Angew Chem Int Ed 52(22): 5688-5698 (2013)] or a spherical nucleic acid (SNA)-NP conjugate, enables the formation of multivalent interactions between particles hybridized to linker strands bearing short complementary sticky ends (FIGS. 1 and 24). When nanoparticles bearing complementary sticky ends are combined, heated to a temperature sufficient to disrupt these multivalent interactions, and then slowly cooled to room temperature, the reversible formation of many individually weak interparticle interactions collectively favor the formation of thermodynamically stable single-crystalline superlattices over kinetically trapped amorphous aggregates [Auyeung et al., Nature 505(7481): 73-77 (2014)]. The inclusion of functional proteins into DNA-mediated superlattices is possible provided that their surfaces can be sufficiently functionalized with oligonucleotides while leaving their native structures intact, which is crucial to maintaining their functionality. A two-step reaction scheme was developed for appending oligonucleotides to protein surfaces under mild conditions, the DNA-functionalized proteins were characterized to ensure that they maintained their native structures and functions, and their DNA-mediated assembly into single-crystalline superlattices was observed.

This disclosure is directed to a variety of applications including, but not limited to:

A method for chemically modifying the surface of a protein with a dense shell of oligonucleotides;
Stabilization of potential protein-based therapeutics towards degradation by cellular proteases or upon prolonged storage Application of the protein-oligonucleotide conjugates for replacement of deficient enzymes (e.g., for lysosomal storage disorders) or for the enzymatic conversion of toxic metabolites (e.g., catalase to decompose $H_2O_2$ after traumatic brain injuries or stroke);
Combined functionalization of proteins with oligonucleotides for cell entry and other chemical moieties for targeting (e.g., Mannose 6-phosphate for targeting to the lysosome);
Application of protein-oligonucleotide conjugates as multifunctional therapeutics Advantages provided by this disclosure include, but are not limited to The use of oligonucleotides as a coating allows for joint therapeutic strategies;
The use of an enzyme core imparts additional functionality compared to other methods for delivery of oligonucleotides;
The sequence of the oligonucleotide shell can be tailored to degrade at a specific rate and expose the protein surface to allow control of cellular processes (e.g., receptor binding to control signaling cascades);
The surface of a protein presents multiple functional groups with orthogonal chemical modification chemistries. This should allow, for instance, modification of the protein surface with multiple oligonucleotides or conjugation of a targeting moiety in addition to the oligonucleotide shell.

The disclosure provides solutions to many of the challenges associated with the use of protein therapeutics (poor cellular uptake, activation of the innate immune response, poor bioavailability, degradation by cellular proteases, or aggregation and inactivation upon prolonged storage).

The disclosed particles are a core technology that can be extended to many different protein-based products. It has the potential to stabilize and improve the pharmacodynamic properties of any enzyme and could therefore be applied to treatment for an array of diseases. Additionally, whereas traditional scaffolds for DNA delivery function solely as a support, protein-based scaffolds can themselves be used as a therapeutic.

Protein-oligonucleotide core-shell NPs consist of a protein core chemically modified with a dense shell of oligonucleotides. The protein core can be chosen from a wide range of proteins with, for example and without limitation, therapeutic, catalytic, signaling, or transport functionalities. Similarly, the oligonucleotide shell can be chosen for its therapeutic value or to have a tunable degradation rate, such that the protein core becomes functional in a physiological setting.

The invention allows the predictable assembly of functional proteins into supramolecular materials. This will allow for the synthesis of materials with defined ratios of two or more components (e.g., multiple proteins or proteins and inorganic nanostructures).

Applications of this technology include but are not limited to: a general method for the synthesis of protein/DNA core-shell nanoparticles; stabilization of proteins upon prolonged storage at room temperature; assembly of enzymatically active crystals; assembly of crystals containing more than one protein that have applications in tandem catalysis; assembly of multicomponent crystals composed of protein molecules and inorganic nanoparticles; and crystallization of proteins for use in structure determination.

Some advantages of this technology include but are not limited to: the high fidelity of DNA duplex formation allows one to predict the assembly behavior of oligonucleotide-functionalized proteins to an extent not possible using other strategies; proteins have many inherent characteristics that make them ideal building block for assembling functional materials, such as a uniform atomic composition and high degree of structural uniformity relative to other nanoscale materials, the presence of surfaces containing multiple chemically modifiable functional groups with orthogonal chemistries and a wide range of catalytic functionalities.

As used herein, a "plurality" means more than one. In the context of polynucleotides, the plurality is a number of polynucleotides attached to the protein core surface that provide sufficient coverage to form a "shell." In some cases, that plurality is measured by polynucleotide density.

As used herein, a "biomolecule" is understood to include a polynucleotide, peptide, protein, phospholipid, oligosaccharide, small molecule, therapeutic agent, contrast agent and combinations thereof.

It is noted here that, as used in this specification and the appended claims, the singular forms "a," "an," and "the" include plural reference unless the context clearly dictates otherwise.

It is also noted that the term "about" as used herein is understood to mean approximately.

Core-Shell Nanoparticle

The basic components of a core-shell nanoparticle of the disclosure are a plurality of polynucleotides and a single protein. In various aspects of the core-shell nanoparticle, all of the polynucleotides are identical, or in the alternative, at least two polynucleotides are different.

Proteins

As used herein, protein is used interchangeably with "polypeptide" and refers to a polymer comprised of amino acid residues. A "single protein" as used herein refers to a contiguous polymer of amino acid residues. Proteins as disclosed herein generally function as the "core" of the core-shell nanoparticle.

Proteins are understood in the art and include without limitation an antibody, an enzyme, a structural protein and a hormone. Thus, proteins contemplated by the disclosure include without limitation those having catalytic, signaling, therapeutic, or transport activity. In various embodiments, catalytic functionalities include biomedically related functions, such as replacing enzymes deficient in lysosomal storage disorders (α-galactosidase, β-glucosidase, β-cerebrosidase, alglucosidase-α, α-mannosidase, β-glucuronidase, α-glucosidase, β-hexosaminidase A, acid lipase, amongst others and variants of these enzymes), enzymes deficient in gastrointestinal disorders (lactase, lipases, amylases, or proteases), or enzymes involved in immunodeficiencies (adenosine deaminase), or include enzymes relevant for technological applications (hydrogenases, lipases, proteases, oxygenases, or laccases), which are in various embodiments used intra- or extracellularly. Signaling proteins include growth factors such as TNF-α or caspases. Human serum albumin are contemplated for use as a transport protein, where small molecule therapeutics or imaging agents would be bound in the core and the DNA shell would serve as a cellular uptake signal.

Proteins of the present disclosure may be either naturally occurring or non-naturally occurring. Proteins optionally include a spacer as described herein.

Naturally Occurring Proteins

Naturally occurring proteins include without limitation biologically active proteins (including antibodies) that exist in nature or can be produced in a form that is found in nature by, for example, chemical synthesis or recombinant expression techniques. Naturally occurring proteins also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Structural proteins contemplated by the disclosure include without limitation actin, tubulin, collagen, elastin, myosin, kinesin and dynein.

Non-Naturally Occurring Proteins

Non-naturally occurring proteins contemplated by the present disclosure include but are not limited to synthetic proteins, as well as fragments, analogs and variants of naturally occurring or non-naturally occurring proteins as defined herein. Non-naturally occurring proteins also include proteins or protein substances that have D-amino acids, modified, derivatized, or non-naturally occurring amino acids in the D- or L-configuration and/or peptidomimetic units as part of their structure. The term "peptide" typically refers to short polypeptides/proteins.

Non-naturally occurring proteins are prepared, for example, using an automated protein synthesizer or, alternatively, using recombinant expression techniques using a modified polynucleotide which encodes the desired protein.

As used herein a "fragment" of a protein is meant to refer to any portion of a protein smaller than the full-length protein or protein expression product.

As used herein an "analog" refers to any of two or more proteins substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physico-chemical or functional relatedness of the amino acid that is being replaced and the amino acid replacing it.

As used herein a "variant" refers to a protein or analog thereof that is modified to comprise additional chemical moieties not normally a part of the molecule. Such moieties may modulate, for example and without limitation, the molecule's solubility, absorption, and/or biological half-life. Moieties capable of mediating such effects are disclosed in Remington's Pharmaceutical Sciences (1980). Procedures for coupling such moieties to a molecule are well known in the art. In various aspects, proteins are modified by glycosylation, pegylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

Proteins include antibodies along with fragments and derivatives thereof, including but not limited to Fab' fragments, F(ab)2 fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRAB s), bispecific antibodies and multispecific antibodies, and other antibody derivative or fragments known in the art.

Density

Depending on the degree of coverage of the protein and the amount of starting component, i.e., the polynucleotides, in the preparative mixture, the core-shell nanoparticles provided are contemplated to have varying densities. Thus, the protein is, in one aspect, completely covered with polynucleotides, or in an alternative aspects, significantly covered with polynucleotides, or sparsely covered with the polynucleotides. The density of coverage of the protein is, in one aspect, even over the entire surface, or in the alternative, the density is uneven over the surface.

In some aspects, the density of polynucleotides that make up the shell of the core-shell nanoparticle provides increased resistance to degradation. In one aspect, the uptake of core-shell nanoparticles by a cell is influenced by the density of polynucleotides associated with the nanoparticle. As described in PCT/US2008/65366, incorporated herein by reference in its entirety, a higher density of polynucleotides on the surface of a polynucleotide functionalized nanoparticle is associated with an increased uptake of nanoparticles by a cell. This aspect is likewise contemplated to be a property of core-shell nanoparticles, wherein a higher density of polynucleotides that comprise the shell of the core-shell nanoparticle is associated with an increased uptake of a core-shell nanoparticle by a cell.

Generally, a surface density of polynucleotides that is at least 2 $pmol/cm^2$ will be adequate to provide a stable core-shell nanoparticle. In some aspects, the surface density is at least 15 $pmol/cm^2$. Compositions and methods are also provided wherein the polynucleotide is present in a core-shell nanoparticle at a surface density of at least 2 $pmol/cm^2$, at least 3 $pmol/cm^2$, at least 4 $pmol/cm^2$, at least 5 $pmol/cm^2$, at least 6 $pmol/cm^2$, at least 7 $pmol/cm^2$, at least 8 $pmol/cm^2$, at least 9 $pmol/cm^2$, at least 10 $pmol/cm^2$, at least about 15 $pmol/cm^2$, at least about 20 $pmol/cm^2$, at least about 25 $pmol/cm^2$, at least about 30 $pmol/cm^2$, at least about 35 $pmol/cm^2$, at least about 40 $pmol/cm^2$, at least about 45 $pmol/cm^2$, at least about 50 $pmol/cm^2$, at least about 55 $pmol/cm^2$, at least about 60 $pmol/cm^2$, at least about 65 $pmol/cm^2$, at least about 70 $pmol/cm^2$, at least about 75 $pmol/cm^2$, at least about 80 $pmol/cm^2$, at least about 85 $pmol/cm^2$, at least about 90 $pmol/cm^2$, at least about 95 $pmol/cm^2$, at least about 100 $pmol/cm^2$, at least about 125 $pmol/cm^2$, at least about 150 $pmol/cm^2$, at least about 175 $pmol/cm^2$, at least about 200 $pmol/cm^2$, at least about 250 $pmol/cm^2$, at least about 300 $pmol/cm^2$, at least about 350 $pmol/cm^2$, at least about 400 $pmol/cm^2$, at least about 450 $pmol/cm^2$, at least about 500 $pmol/cm^2$, at least about 550 $pmol/cm^2$, at least about 600 $pmol/cm^2$, at least about 650 $pmol/cm^2$, at least about 700 $pmol/cm^2$, at least about 750 $pmol/cm^2$, at least about 800 $pmol/cm^2$, at least about 850 $pmol/cm^2$, at least about 900 $pmol/cm^2$, at least about 950 $pmol/cm^2$, at least about 1000 $pmol/cm^2$ or more.

Polynucleotides

The terms "polynucleotide" and "oligonucleotide" are used interchangeably herein. Polynucleotides, whether as part of the shell of the core-shell particle or as additional agents, are contemplated by the present disclosure to include DNA, RNA, modified forms and combinations thereof as defined herein. Accordingly, in some aspects, the core-shell nanoparticle comprises DNA. In some embodiments, the DNA is double stranded, and in further embodiments the DNA is single stranded. In further aspects, the core-shell nanoparticle comprises RNA, and in still further aspects the core-shell nanoparticle comprises double stranded RNA, and in a specific embodiment, the double stranded RNA agent is a small interfering RNA (siRNA). The term "RNA" includes duplexes of two separate strands, as well as single stranded structures. Single stranded RNA also includes RNA with secondary structure. In one aspect, RNA having a hairpin loop in contemplated.

The core-shell nanoparticle comprises, in various embodiments, a plurality of polynucleotides comprised of a sequence that is sufficiently complementary to a target sequence of a target polynucleotide such that hybridization of the polynucleotide that is part of the core-shell nanoparticle and the target polynucleotide takes place. The polynucleotide in various aspects is single stranded or double stranded, as long as the double stranded molecule also includes a single strand sequence that hybridizes to a single strand sequence of the target polynucleotide. In some aspects, hybridization of the polynucleotide that is part of the core-shell nanoparticle can form a triplex structure with a double-stranded target polynucleotide. In another aspect, a triplex structure can be formed by hybridization of a double-stranded polynucleotide that is part of a core-shell nanoparticle to a single-stranded target polynucleotide. Further description of triplex polynucleotide complexes is found in PCT/US2006/40124, which is incorporated herein by reference in its entirety.

In some aspects, polynucleotides contain a spacer as described herein.

A "polynucleotide" is understood in the art to comprise individually polymerized nucleotide subunits. The term "nucleotide" or its plural as used herein is interchangeable with modified forms as discussed herein and otherwise known in the art. In certain instances, the art uses the term "nucleobase" which embraces naturally-occurring nucleotide, and non-naturally-occurring nucleotides which include modified nucleotides. Thus, nucleotide or nucleobase means the naturally occurring nucleobases adenine (A), guanine (G), cytosine (C), thymine (T) and uracil (U). Non-naturally occurring nucleobases include, for example and without limitations, xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which are a category of non-naturally-occurring nucleotides that include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Modified nucleotides are described in EP 1 072 679 and WO 97/12896, the disclosures of which are incorporated herein by reference. Modified nucleotides include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

A polynucleotide of the disclosure, or a modified form thereof, is generally from about 5 nucleotides to about 100 nucleotides in length. In general, a longer polynucleotide will result in slower degradation of the core-shell nanoparticle. More specifically, core-shell nanoparticles comprise polynucleotides that are about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated. Specifically contemplated herein are polynucleotides having 15 to 100 nucleotides, or 15 to 60 nucleotides, or 18 to 30 nucleotides.

Polynucleotides, as defined herein, also includes aptamers. The production and use of aptamers is known to those of ordinary skill in the art. In general, aptamers are nucleic acid or peptide binding species capable of tightly binding to and discreetly distinguishing target ligands [Yan et al., RNA Biol. 6(3) 316-320 (2009), incorporated by reference herein in its entirety]. Aptamers, in some embodiments, may be obtained by a technique called the systematic evolution of ligands by exponential enrichment (SELEX) process [Tuerk et al., Science 249:505-10 (1990), U.S. Pat. Nos. 5,270,163, and 5,637,459, each of which is incorporated herein by reference in their entirety]. General discussions of nucleic acid aptamers are found in, for example and without limitation, Nucleic Acid and Peptide Aptamers: Methods and Protocols (Edited by Mayer, Humana Press, 2009) and Crawford et al., Briefings in Functional Genomics and Proteomics 2(1): 72-79 (2003). Additional discussion of aptamers, including but not limited to selection of RNA aptamers, selection of DNA aptamers, selection of aptamers capable of covalently linking to a target protein, use of modified aptamer libraries, and the use of aptamers as a diagnostic agent and a therapeutic agent is provided in Kopylov et al., Molecular Biology 34(6): 940-954 (2000) translated from Molekulyarnaya Biologiya, Vol. 34, No. 6, 2000, pp. 1097-1113, which is incorporated herein by reference in its entirety. In various aspects, an aptamer is between 10-100 nucleotides in length.

Spacers

In certain aspects, core-shell nanoparticles are contemplated which include those wherein a core-shell nanoparticle comprises a polynucleotide which further comprises a spacer.

"Spacer" as used herein means a moiety that serves to increase distance between the polynucleotide and the core to which the polynucleotide is attached. In some aspects of the disclosure wherein a core-shell nanoparticle is used for a biological activity, it is contemplated that the spacer does not directly participate in the activity of the polynucleotide to which it is attached. In alternative aspects, the spacer may be all or in part complementary to a target polynucleotide.

Spacers are additionally contemplated, in various aspects, as being located between individual polynucleotides in tandem, whether the polynucleotides have the same sequence or have different sequences. In one aspect, the spacer when present is an organic moiety. In another aspect, the spacer is a polymer, including but not limited to a water-soluble polymer, a nucleic acid, a protein, an oligosaccharide, a carbohydrate, a lipid, or combinations thereof.

The length of a spacer, in various embodiments, is at least about 5 nucleotides, at least about 10 nucleotides, 10-30 nucleotides, 10-40 nucleotides, 10-50 nucleotides, 10-60 nucleotides, or even greater than 60 nucleotides. The spacers should not have sequences complementary to each other or to that of the polynucleotides. In certain aspects, the bases of the polynucleotide spacer are all adenines, all thymines, all cytidines, all guanines, all uracils, or all some other modified base. In some embodiments, a spacer does not contain nucleotides, and in such embodiments the spacer length is equivalent to at least about 5 nucleotides, at least about 10 nucleotides, 10-30 nucleotides, 10-40 nucleotides, 10-50 nucleotides, 10-60 nucleotides, or even greater than 60 nucleotides.

Modified Polynucleotides

As discussed above, modified polynucleotides are contemplated for use in producing core-shell nanoparticles. In various aspects, a polynucleotide of the disclosure is completely modified or partially modified. Thus, in various aspects, one or more, or all, sugar and/or one or more or all internucleotide linkages of the nucleotide units in the polynucleotide are replaced with "non-naturally occurring" groups.

In one aspect, the disclosure contemplates use of a peptide nucleic acid (PNA). In PNA compounds, the sugar-backbone of a polynucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotide."

Modified polynucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In still other embodiments, polynucleotides are provided with phosphorothioate backbones and oligonucleosides with heteroatom backbones, and including $CH_2$—NH—O—$CH_2$—, $CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. See, for example, U.S. Pat. Nos. 5,034,506; 5,166,315; 5,185, 444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In various forms, the linkage between two successive monomers in the polynucleotide consists of 2 to 4, desirably 3, groups/atoms selected from —CH2—, —O—, —S—, —NRH—, >C=O, >C=NRH, >C=S, —Si(R")$_2$—, —SO—, —S(O)$_2$—, —P(O)$_2$—, —PO(BH$_3$)—, —P(O,S)—, —P(S)$_2$—, —PO(R")—, —PO(OCH$_3$)—, and PO(NHRH)—, where RH is selected from hydrogen and C1-4-alkyl, and R" is selected from C1-6-alkyl and phenyl. Illustrative examples of such linkages are —CH$_2$—CH$_2$—CH$_2$—, CH$_2$—CO—CH$_2$—, —CH$_2$—CHOH—CH$_2$—, —O—CH$_2$—O—, —O—CH$_2$—CH$_2$—, O—CH$_2$—CH= (including R$_5$ when used as a linkage to a succeeding monomer), —CH$_2$—CH$_2$—O—, —NRH—CH$_2$—CH$_2$—, —CH$_2$—CH$_2$—NRH—, —CH2—NRH—CH$_2$—, —O—CH$_2$—CH$_2$—NRH—, —NRH—CO—O—, —NRH—CO—NRH—, —NRH—CS—NRH—, —NRH—C(=NRH)—NRH—, —NRH—CO—CH$_2$—NRH—O—CO—O—, —O—CO—CH$_2$—O—, —O—CH$_2$—CO—O—, —CH$_2$—CO—NRH—, O—CO—NRH—, —NRH—CO—CH$_2$—, —O—CH$_2$—CO—NRH—, —O—CH$_2$—CH$_2$—NRH—, CH=N—O—, —CH$_2$—NRH—O—, —CH$_2$—O—N=(including R$_5$ when used as a linkage to a succeeding monomer), —CH$_2$—O—NRH—, —CO—NRH—CH$_2$—, —CH$_2$—NRH—O—, —CH$_2$—NRH—CO—, —O—NRH—CH$_2$—, —O—NRH, —O—CH$_2$—S—, —S—CH$_2$—O—, —CH$_2$—CH$_2$—S—, —O—CH$_2$—CH$_2$—S—, —S—CH$_2$—CH=(including R$_5$ when used as a linkage to a succeeding monomer), —S—CH$_2$—CH$_2$—, —S—CH$_2$—CH$_2$—O—, —S—CH$_2$—CH$_2$—S—, —CH$_2$—S—CH$_2$—, —CH$_2$—SO—CH$_2$—, —CH$_2$—SO$_2$—CH$_2$—, —O—SO—O—, —O—S(O)$_2$—O—, —O—S(O)$_2$—CH$_2$—, —O—S(O)$_2$—NRH—, —NRH—S(O)$_2$—CH$_2$—; —O—S(O)$_2$—CH$_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHRN)—O—, —O—P(O)$_2$—NRH H—, —NRH—P(O)$_2$—O—, —O—P(O,NRH)—O—, —CH$_2$—P(O)$_2$—O—, —O—P(O)$_2$—CH$_2$—, and —O—Si(R")$_2$—O—; among which —CH$_2$—CO—NRH—, —CH$_2$—NRH—O—, —S—CH$_2$—O—, —O—P(O)$_2$—O—O—P(—O,S)—O—, —O—P(S)$_2$—O—, —NRH P(O)$_2$—O—, —O—P(O,NRH)—O—, —O—PO(R")—O—, —O—PO(CH$_3$)—O—, and —O—PO(NHRN)—O—, where RH is selected form hydrogen and C$_{1-4}$-alkyl, and R" is selected from C$_{1-6}$-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Publication No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O—, S—, or N-alkyl; O—, S—, or N-alkenyl; O—, S—or N-alkynyl; or O-alkyl-O-alkyl, wherein the alkyl, alkenyl and alkynyl may be substituted or unsubstituted C1 to C10 alkyl or C2 to C10 alkenyl and alkynyl. Other embodiments include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH2)$_n$CH$_3$]$_2$, where n and m are from 1 to about 10. Other polynucleotides comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'—O—CH$_2$CH$_2$OCH$_3$, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$.

Still other modifications include 2'-methoxy (2'—O—CH$_3$), 2'-aminopropoxy (2'-OCH$_2$CH$_2$CH$_2$NH$_2$), 2'-allyl (2'—CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH$_2$—)n group bridging the 2' oxygen atom and the 4' carbon atom wherein n is 1 or 2. LNAs and preparation thereof are described in WO 98/39352 and WO 99/14226, the disclosures of which are incorporated herein by reference.

Polynucleotide Features

Each core-shell nanoparticle provided comprises a plurality of polynucleotides. As a result, each core-shell nanoparticle has the ability to bind to a plurality of target polynucleotides having a sufficiently complementary sequence. For example, if a specific polynucleotide is targeted, a single core-shell nanoparticle has the ability to bind to multiple copies of the same molecule. In one aspect, methods are provided wherein the core-shell nanoparticle comprises identical polynucleotides, i.e., each polynucleotide has the same length and the same sequence. In other aspects, the core-shell nanoparticle comprises two or more polynucleotides which are not identical, i.e., at least one of the polynucleotides of the core-shell nanoparticle differ from at least one other polynucleotide of the core-shell nanoparticle in that it has a different length and/or a different sequence. In aspects wherein a core-shell nanoparticle comprises different polynucleotides, these different polynucleotides bind to the same single target polynucleotide but at different locations, or bind to different target polynucleotides which encode different gene products. Accordingly, in various aspects, a single core-shell nanoparticle may be used in a method to inhibit expression of more than one gene product. Polynucleotides are thus used to target specific polynucleotides, whether at one or more specific regions in the target polynucleotide, or over the entire length of the target polynucleotide as the need may be to effect a desired level of inhibition of gene expression.

Accordingly, in one aspect, the polynucleotides are designed with knowledge of the target sequence. Alternatively, a polynucleotide in a core-shell nanoparticle need not hybridize to a target polynucleotide in order to achieve a desired effect as described herein. Regardless, methods of making polynucleotides of a predetermined sequence are well-known. See, for example, Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are contemplated for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Alternatively, polynucleotides are selected from a library. Preparation of libraries of this type is well known in the art. See, for example, Oligonucleotide libraries: United States Patent Application 20050214782, published Sep. 29, 2005.

Polynucleotides contemplated for production of a core-shell nanoparticle include, in various aspects, those which modulate expression of a gene product expressed from a target polynucleotide. Accordingly, antisense polynucleotides which hybridize to a target polynucleotide and inhibit translation, siRNA polynucleotides which hybridize to a target polynucleotide and initiate an RNAse activity (for example RNAse H), triple helix forming polynucleotides which hybridize to double-stranded polynucleotides and inhibit transcription, and ribozymes which hybridize to a target polynucleotide and inhibit translation, are contemplated.

In some aspects, a core-shell nanoparticle allows for efficient uptake of the core-shell nanoparticle. In various aspects, the polynucleotide comprises a nucleotide sequence that allows increased uptake efficiency of the core-shell nanoparticle. As used herein, "efficiency" refers to the number or rate of uptake of core-shell nanoparticles in/by a cell. Because the process of core-shell nanoparticles entering and exiting a cell is a dynamic one, efficiency can be increased by taking up more core-shell nanoparticles or by retaining those core-shell nanoparticles that enter the cell for a longer period of time. Similarly, efficiency can be decreased by taking up fewer core-shell nanoparticles or by retaining those core-shell nanoparticles that enter the cell for a shorter period of time.

Thus, the nucleotide sequence can be any nucleotide sequence that is desired may be selected for, in various aspects, increasing or decreasing cellular uptake of a core-shell nanoparticle or gene regulation. The nucleotide sequence, in some aspects, comprises a homopolymeric sequence which affects the efficiency with which the core-shell nanoparticle is taken up by a cell. Accordingly, the homopolymeric sequence increases or decreases the efficiency. It is also contemplated that, in various aspects, the nucleotide sequence is a combination of nucleobases, such that it is not strictly a homopolymeric sequence. For example and without limitation, in various aspects, the nucleotide sequence comprises alternating thymidine and uridine residues, two thymidines followed by two uridines or any combination that affects increased uptake is contemplated by the disclosure. In some aspects, the nucleotide sequence affecting uptake efficiency is included as a domain in a polynucleotide comprising additional sequence. This "domain" would serve to function as the feature affecting uptake efficiency, while the additional nucleotide sequence would serve to function, for example and without limitation, to regulate gene expression. In various aspects, the domain in the polynucleotide can be in either a proximal, distal, or center location relative to the core. It is also contemplated that a polynucleotide comprises more than one domain.

The homopolymeric sequence, in some embodiments, increases the efficiency of uptake of the core-shell nanoparticle by a cell. In some aspects, the homopolymeric sequence comprises a sequence of thymidine residues (polyT) or uridine residues (polyU). In further aspects, the polyT or polyU sequence comprises two thymidines or uridines. In various aspects, the polyT or polyU sequence comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 175, about 200, about 250, about 300, about 350, about 400, about 450, about 500 or more thymidine or uridine residues.

In some embodiments, it is contemplated that a core-shell nanoparticle comprising a polynucleotide that comprises a homopolymeric sequence is taken up by a cell with greater efficiency than a core-shell nanoparticle comprising the same polynucleotide but lacking the homopolymeric sequence. In various aspects, a core-shell nanoparticle comprising a polynucleotide that comprises a homopolymeric sequence is taken up by a cell about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, more efficiently than a core-shell nanoparticle comprising the same polynucleotide but lacking the homopolymeric sequence.

In other aspects, the domain is a phosphate polymer (C3 residue). In some aspects, the domain comprises a phosphate polymer (C3 residue) that is comprised of two phosphates. In various aspects, the C3 residue comprises 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, about 55, about 60, about 65, about 70, about 75, about 80, about 85, about 90, about 95, about 100, about 125, about 150, about 175, about 200, about 250, about 300, about 350, about 400, about 450, about 500 or more phosphates.

In some embodiments, it is contemplated that a core-shell nanoparticle comprising a polynucleotide which comprises a domain is taken up by a cell with lower efficiency than a core-shell nanoparticle comprising the same polynucleotide but lacking the domain. In various aspects, a core-shell nanoparticle comprising a polynucleotide which comprises a domain is taken up by a cell about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 100-fold or higher, less efficiently than a core-shell nanoparticle comprising the same polynucleotide but lacking the domain.

As used herein, a "conjugation site" is understood to mean a site on a polynucleotide to which a contrast agent is attached. In certain aspects, the disclosure also provides one or more polynucleotides that are part of the core-shell nanoparticle which do not comprise a conjugation site while one or more polynucleotides that are part of the same core-shell nanoparticle do comprise a conjugation site. Conjugation of a contrast agent to a core-shell nanoparticle through a conjugation site is generally described in PCT/US2010/44844, which is incorporated herein by reference in its entirety. The disclosure provides, in one aspect, a core-shell nanoparticle comprising a polynucleotide wherein the polynucleotide comprises one to about ten conjugation sites. In another aspect, the polynucleotide comprises five conjugation sites. In general, for a nucleotide, both its backbone (phosphate group) and nucleobase can be modified. Accordingly, the present disclosure contemplates that there are 2n conjugation sites, where n=length of the polynucleotide template. In some aspects, the plurality of polynucleotides of the core-shell nanoparticle comprises at least one polynucleotide to which contrast agents are associated through one or more conjugation sites, as well as at least one polynucleotide that has gene regulatory activity as described herein.

Polynucleotide Copies—Same/Different Sequences

Core-shell nanoparticles are provided which include those wherein a single sequence in a single polynucleotide or multiple copies of the single sequence in a single polynucleotide is part of a core-shell nanoparticle. Thus, in various aspects, a polynucleotide is contemplated with multiple copies of a single sequence in tandem, for example, two, three, four, five, six, seven eight, nine, ten or more tandem repeats.

Alternatively, the core-shell nanoparticle includes at least two polynucleotides having different sequences. As above, the different polynucleotide sequences are in various aspects arranged in tandem (i.e., on a single polynucleotide) and/or in multiple copies (i.e., on at least two polynucleotides). In methods wherein polynucleotides having different sequences are part of the core-shell nanoparticle, aspects of the disclosure include those wherein the different polynucleotide sequences hybridize to different regions on the same polynucleotide. Alternatively, the different polynucleotide sequences hybridize to different polynucleotides.

Additional Agents

The core-shell nanoparticles provided by the disclosure optionally include an additional agent. The additional agent is, in various embodiments, simply associated with one or more of the plurality of polynucleotides that make up the shell of the core-shell nanoparticle, and/or the additional agent is associated with the protein core of the core-shell nanoparticle. It is contemplated that this additional agent is in one aspect covalently associated with the one or more of the plurality of polynucleotides, or in the alternative, non-covalently associated with the one or more of the plurality of polynucleotides. However, it is understood that the disclosure provides core-shell nanoparticles wherein one or more additional agents are both covalently and non-covalently associated with one or more of the plurality of polynucleotides. It will also be understood that non-covalent associations include hybridization (i.e., between polynucleotides), protein binding (i.e., between proteins which can bind or between a protein and an aptamer) and/or hydrophobic interactions (i.e., between lipids and other agents that include a sufficiently hydrophobic domain).

Additional agents contemplated by the disclosure include without limitation a polynucleotide, a peptide, a detectable marker, a phospholipid, an oligosaccharide, a metal complex, a small molecule, a contrast agent, a protein (e.g., a therapeutic agent), an antibiotic, a targeting moiety, and a combination thereof. These additional agents are discussed herein.

Therapeutic Agents

"Therapeutic agent," "drug" or "active agent" as used herein means any compound useful for therapeutic or diagnostic purposes. The terms as used herein are understood to mean any compound that is administered to a patient for the treatment of a condition. To the extent any of the therapeutic agents contemplated below are proteins, those proteins are also contemplated for use as the "single protein" of a core-shell nanoparticle.

The present disclosure is applicable to any therapeutic agent for which delivery is desired. Non-limiting examples of such active agents as well as hydrophobic drugs are found in U.S. Pat. No. 7,611,728, which is incorporated by reference herein in its entirety. Additional therapeutic agents contemplated for use are found in PCT/US2010/55018, which is incorporated by reference herein in its entirety.

Core-shell nanoparticles and methods disclosed herein, in various embodiments, are provided wherein the core-shell nanoparticle comprises a multiplicity of therapeutic agents. In one aspect, compositions and methods are provided wherein the multiplicity of therapeutic agents are specifically attached to one core-shell nanoparticle via association with one or more polynucleotides in the shell. In another aspect, the multiplicity of therapeutic agents is specifically attached to more than one core-shell nanoparticle.

Therapeutic agents include but are not limited to hydrophilic and hydrophobic compounds.

Protein therapeutic agents include, without limitation peptides, enzymes, structural proteins, receptors and other cellular or circulating proteins as well as fragments and derivatives thereof, the aberrant expression of which gives rise to one or more disorders. Therapeutic agents also include, as one specific embodiment, chemotherapeutic agents. Therapeutic agents also include, in various embodiments, a radioactive material.

In various aspects, protein therapeutic agents include cytokines or hematopoietic factors including without limitation IL-1 alpha, IL-1 beta, IL-2, IL-3, IL-4, IL-5, IL-6, IL-11, colony stimulating factor-1 (CSF-1), M-CSF, SCF, GM-CSF, granulocyte colony stimulating factor (G-CSF), interferon-alpha (IFN-alpha), consensus interferon, IFN-beta, IFN-gamma, IL-7, IL-8, IL-9, IL-10, IL-12, IL-13, IL-14, IL-15, IL-16, IL-17, IL-18, erythropoietin (EPO), thrombopoietin (TPO), angiopoietins, for example Ang-1, Ang-2, Ang-4, Ang-Y, the human angiopoietin-like polypeptide, vascular endothelial growth factor (VEGF), angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neurotrophic factor, ciliary neutrophic factor receptor, cytokine-induced neutrophil chemotactic factor 1, cytokine-induced neutrophil, chemotactic factor 2α, cytokine-induced neutrophil chemotactic factor 2β, β endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor nerve growth factor receptor, neurotrophin-3, neurotrophin-4, placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor receptor, TNF, including TNF0, TNF1, TNF2, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof. Examples of biologic agents include, but are not limited to, immuno-modulating proteins such as cytokines, monoclonal antibodies against tumor antigens, tumor suppressor genes, and cancer vaccines. Examples of interleukins that may be used in conjunction with the compositions and methods of the present invention include, but are not limited to, interleukin 2 (IL-2), and interleukin 4 (IL-4), interleukin 12 (IL-12). Other immuno-modulating agents other than cytokines include, but are not limited to bacillus Calmette-Guerin, levamisole, and octreotide.

As described by the present disclosure, in some aspects therapeutic agents include small molecules. The term "small molecule," as used herein, refers to a chemical compound, for instance a peptidomic that may optionally be derivatized, or any other low molecular weight organic compound, either natural or synthetic. Such small molecules may be a therapeutically deliverable substance or may be further derivatized to facilitate delivery.

By "low molecular weight" is meant compounds having a molecular weight of less than 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900, about 1000 Daltons.

The term "drug-like molecule" is well known to those skilled in the art, and includes the meaning of a compound that has characteristics that make it suitable for use in medicine, for example and without limitation as the active agent in a medicament. Thus, for example and without limitation, a drug-like molecule is a molecule that is synthesized by the techniques of organic chemistry, or by techniques of molecular biology or biochemistry, and is in some aspects a small molecule as defined herein. A drug-like molecule, in various aspects, additionally exhibits features of selective interaction with a particular protein or proteins and is bioavailable and/or able to penetrate cellular membranes either alone or in combination with a composition or method of the present disclosure.

In various embodiments, therapeutic agents described in U.S. Pat. No. 7,667,004 (incorporated by reference herein in its entirety) are contemplated for use in the compositions and methods disclosed herein and include, but are not limited to, alkylating agents, antibiotic agents, antimetabolic agents, hormonal agents, plant-derived agents, and biologic agents.

Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (e.g., carboplastin, cisplatin and platinum (IV) (Pt (IV))).

Examples of antibiotic agents include, but are not limited to, anthracyclines (e.g. doxorubicin, daunorubicin, epirubicin, idarubicin and anthracenedione), mitomycin C, bleomycin, dactinomycin, plicamycin. Additional antibiotic agents are discussed in detail below.

Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, imatinib mesylate (or GLEEVE®), and gemcitabine.

Examples of hormonal agents include, but are not limited to, synthetic estrogens (e.g. diethylstilbestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone.

Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), camptothecin compounds (e.g., 20(S) camptothecin, topotecan, rubitecan, and irinotecan), taxanes (e.g., paclitaxel and docetaxel).

Chemotherapeutic agents contemplated for use include, without limitation, alkylating agents including: nitrogen mustards, such as mechlor-ethamine, cyclophosphamide, ifosfamide, melphalan and chlorambucil; nitrosoureas, such as carmustine (BCNU), lomustine (CCNU), and semustine (methyl-CCNU); ethylenimines/methylmelamine such as triethylenemelamine (TEM), triethylene, thiophosphoramide (thiotepa), hexamethylmelamine (HMM, altretamine); alkyl sulfonates such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycitidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as paclitaxel, vinca alkaloids including vinblastine (VLB), vincristine, and vinorelbine, taxotere, estramustine, and estramustine phosphate; epipodophyllotoxins such as etoposide and teniposide; antibiotics such as actinomycin D, daunomycin (rubidomycin), doxorubicin, mitoxantrone, idarubicin, bleomycins, plicamycin (mithramycin), mitomycinC, and actinomycin; enzymes such as L-asparaginase; biological response modifiers such as interferon-alpha, IL-2, G-CSF and GM-CSF; miscellaneous agents including platinum coordination complexes such as cisplatin, Pt(IV) and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; and non-steroidal antiandrogens such as flutamide.

Markers/Labels

A protein, polynucleotide, or additional agent as described herein, in various aspects, optionally comprises a detectable label. Accordingly, the disclosure provides compositions and methods wherein complex formation is detected by a detectable change. In one aspect, complex formation gives rise to a color change which is observed with the naked eye or spectroscopically.

Methods for visualizing the detectable change resulting from biomolecule complex formation also include any fluorescent detection method, including without limitation fluorescence microscopy, a microtiter plate reader or fluorescence-activated cell sorting (FACS).

It will be understood that a label contemplated by the disclosure includes any of the fluorophores described herein as well as other detectable labels known in the art. For example, labels also include, but are not limited to, redox active probes, chemiluminescent molecules, radioactive labels, dyes, fluorescent molecules, phosphorescent molecules, imaging and/or contrast agents as described below, quantum dots, as well as any marker which can be detected using spectroscopic means, i.e., those markers detectable using microscopy and cytometry. In aspects of the disclosure wherein a detectable label is to be detected, the disclosure provides that any luminescent, fluorescent, or phosphorescent molecule or particle can be efficiently quenched by noble metal surfaces. Accordingly, each type of molecule is contemplated for use in the compositions and methods disclosed.

Methods of labeling biomolecules with fluorescent molecules and measuring fluorescence are well known in the art.

Suitable fluorescent molecules are also well known in the art and include without limitation 1,8-ANS (1-Anilinonaphthalene-8-sulfonic acid), 1-Anilinonaphthalene-8-sulfonic acid (1,8-ANS), 5-(and −6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO—PRO-1-DNA, BO—PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PicoGreen dsDNA quantitation reagent, PO—PRO-1, PO—PRO-1-DNA, PO—PRO-3, PO—PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodamine Green pH 7.0, Rhodol Green antibody conjugate pH 8.0, Sapphire, SBFI-Na+, Sodium Green Na+, Sulforhodamine 101, EtOH, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO—PRO-1-DNA, YO—PRO-3-DNA, YOYO-1-DNA, and YOYO-3-DNA.

It is also contemplated by the disclosure that, in some aspects, fluorescent proteins are used. Any detectable protein known in the art is useful in the methods of the disclosure, and in some aspects is a fluorescent protein including without limitation EGFP, ECFP, and EYFP.

Contrast Agents

Disclosed herein are, in various aspects, methods and materials comprising a core-shell nanoparticle, wherein a polynucleotide is conjugated to a contrast agent through a conjugation site. In further aspects, a contrast agent is conjugated to a protein or additional agent as described herein. As used herein, a "contrast agent" is a compound or other substance introduced into a cell in order to create a difference in the apparent density of various organs and tissues, making it easier to see the delineate adjacent body tissues and organs.

In some embodiments, the contrast agent is selected from the group consisting of gadolinium, xenon, iron oxide, a manganese chelate (Mn-DPDP) and copper. Thus, in some embodiments the contrast agent is a paramagnetic compound, and in some aspects, the paramagnetic compound is gadolinium.

In certain embodiments the contrast agent comprises a positron emission tomography (PET) contrast agent comprising a label selected from the group consisting of $^{11}$C, $^{13}$N, $^{18}$F, $^{64}$Cu, $^{68}$Ge, $^{99m}$Tc and $^{82}$Ru. In particular embodiments the contrast agent is a PET contrast agent selected from the group consisting of [$^{11}$C]choline, [$^{18}$F]fluorodeoxyglucose(FDG), [$^{11}$C]methionine, [$^{11}$C]choline, [$^{11}$C]acetate, [$^{18}$F]fluorocholine, $^{64}$Cu chelates, $^{99m}$Tc chelates, and [$^{18}$F]polyethyleneglycol stilbenes.

The disclosure also provides methods wherein a PET contrast agent is introduced into a polynucleotide during the polynucleotide synthesis process or is conjugated to a nucleotide following polynucleotide synthesis. For example and without limitation, nucleotides can be synthesized in which one of the phosphorus atoms is replaced with $^{32}$P or $^{33}$P one of the oxygen atoms in the phosphate group is replaced with $^{35}$S, or one or more of the hydrogen atoms is replaced with $^{3}$H. A functional group containing a radionuclide can also be conjugated to a nucleotide through conjugation sites.

MRI contrast agents can include, but are not limited to positive contrast agents and/or negative contrast agents. Positive contrast agents cause a reduction in the $T_1$ relaxation time (increased signal intensity on $T_1$ weighted images). They (appearing bright on MRI) are typically small molecular weight compounds containing as their active element Gadolinium, Manganese, or Iron. A special group of negative contrast agents (appearing dark on MRI) include perfluorocarbons (perfluorochemicals), because their presence excludes the hydrogen atoms responsible for the signal in MR imaging.

The composition of the disclosure, in various aspects, is contemplated to comprise a core-shell nanoparticle that comprises about 50 to about $2.5 \times 10^6$ contrast agents. In some embodiments, the core-shell nanoparticle comprises about 500 to about $1 \times 10^6$ contrast agents.

Targeting Moiety

The term "targeting moiety" as used herein refers to any molecular structure which assists a compound or other molecule in binding or otherwise localizing to a particular target, a target area, entering target cell(s), or binding to a target receptor. For example and without limitation, targeting moieties may include proteins, including antibodies and protein fragments capable of binding to a desired target site in vivo or in vitro, peptides, small molecules, anticancer agents, polynucleotide-binding agents, carbohydrates, ligands for cell surface receptors, aptamers, lipids (including cationic, neutral, and steroidal lipids, virosomes, and liposomes), antibodies, lectins, ligands, sugars, steroids, hormones, and nutrients, may serve as targeting moieties. Targeting moieties are useful for delivery of the core-shell nanoparticle to specific cell types and/or organs, as well as sub-cellular locations.

In some embodiments, the targeting moiety is a protein. The protein portion of the composition of the present disclosure is, in some aspects, a protein capable of targeting the core-shell nanoparticle to a target cell. The targeting protein of the present disclosure may bind to a receptor, substrate, antigenic determinant, or other binding site on a target cell or other target site.

Antibodies useful as targeting proteins may be polyclonal or monoclonal. A number of monoclonal antibodies (MAbs) that bind to a specific type of cell have been developed. Antibodies derived through genetic engineering or protein engineering may be used as well.

The antibody employed as a targeting agent in the present disclosure may be an intact molecule, a fragment thereof, or a functional equivalent thereof. Examples of antibody fragments useful in the compositions of the present disclosure are F(ab')$_2$, Fab' Fab and Fv fragments, which may be produced by conventional methods or by genetic or protein engineering.

In some embodiments, the polynucleotide portion of the core-shell nanoparticle may serve as an additional or auxiliary targeting moiety. The polynucleotide portion may be selected or designed to assist in extracellular targeting, or to act as an intracellular targeting moiety. That is, the polynucleotide portion may act as a DNA probe seeking out target cells. In some embodiments, this additional targeting capability will serve to improve specificity in delivery of the composition to target cells. The polynucleotide may additionally or alternatively be selected or designed to target the composition within target cells, while the targeting protein targets the conjugate extracellularly.

It is contemplated that the targeting moiety can, in various embodiments, be associated with a core-shell nanoparticle. In some aspects, it is therefore contemplated that the targeting moiety is attached to either the protein of the core-shell particle, the polynucleotide of the core-shell nanoparticle, or both.

Phospholipids

Also contemplated by the disclosure are core-shell nanoparticles comprising phospholipids. A phospholipid biomolecule includes, in certain aspects, an optional spacer component.

Lipid and phospholipid-derived hormones are contemplated by the disclosure, and these compounds derive from lipids such as linoleic acid and arachidonic acid and phospholipids. The main classes are the steroid hormones that derive from cholesterol and the eicosanoids.

Metal Complexes

A "metal complex" as used herein refers to a metal and includes without limitation a platinum compound as described herein, germanium(IV), titanium(IV), tin(IV), ruthenium(III), gold(III), and copper(II). A metal complex optionally includes a spacer as described herein.

Oligosaccharides

Oligosaccharides include any carbohydrates comprising between about two to about ten monosaccharides or more connected by either an alpha- or beta-glycosidic link. Oligosaccharides are found throughout nature in both the free and bound form. Oligosaccharides optionally include a spacer as described herein above.

Inorganic Nanoparticles

The disclosure contemplates compositions that comprise a metallic nanoparticle. Thus, nanoparticles are contemplated which comprise a variety of inorganic materials including, but not limited to, metals, semi-conductor materials or ceramics as described in US patent application No 20030147966. For example, metal-based nanoparticles include those described herein. Ceramic nanoparticle materials include, but are not limited to, brushite, tricalcium phosphate, alumina, silica, and zirconia. Organic materials from which nanoparticles are produced include carbon. Nanoparticle polymers include polystyrene, silicone rubber, polycarbonate, polyurethanes, polypropylenes, polymethylmethacrylate, polyvinyl chloride, polyesters, polyethers, and polyethylene. Biodegradable, biopolymer (e.g. polypeptides such as BSA, polysaccharides, etc.), other biological materials (e.g. carbohydrates), and/or polymeric compounds are also contemplated for use in producing nanoparticles.

In some embodiments, the nanoparticle is metallic, and in various aspects, the nanoparticle is a colloidal metal. Thus, in various embodiments, nanoparticles useful in the practice of the methods include metal (including for example and without limitation, gold, silver, platinum, aluminum, palladium, copper, cobalt, iron, indium, nickel, or any other metal amenable to nanoparticle formation), semiconductor (including for example and without limitation, CdSe, CdS, and CdS or CdSe coated with ZnS) and magnetic (for example, ferromagnetite) colloidal materials. Other nanoparticles useful in the practice of the invention include, also without limitation, ZnS, ZnO, Ti, TiO2, Sn, SnO2, Si, SiO2, Fe, Fe+4, Fe3O4, Fe2O3, Ag, Cu, Ni, Al, steel, cobalt-chrome alloys, Cd, titanium alloys, AgI, AgBr, HgI2, PbS, PbSe, ZnTe, CdTe, In2S3, In2Se3, Cd3P2, Cd3As2, InAs, and GaAs. Methods of making ZnS, ZnO, TiO2, AgI, AgBr, HgI2, PbS, PbSe, ZnTe, CdTe, In2S3, In2Se3, Cd3P2, Cd3As2, InAs, and GaAs nanoparticles are also known in the art. See, e.g., Weller, Angew. Chem. Int. Ed. Engl., 32, 41 (1993); Henglein, Top. Curr. Chem., 143, 113 (1988); Henglein, Chem. Rev., 89, 1861 (1989); Brus, Appl. Phys. A., 53, 465 (1991); Bahncmann, in Photochemical Conversion and Storage of Solar Energy (eds. Pelizetti and Schiavello 1991), page 251; Wang and Herron, J. Phys. Chem., 95, 525 (1991); Olshaysky, et al., J. Am. Chem. Soc., 112, 9438 (1990); Ushida et al., J. Phys. Chem., 95, 5382 (1992).

Methods of making metal, semiconductor and magnetic nanoparticles are well-known in the art. See, for example, Schmid, G. (ed.) Clusters and Colloids (VCH, Weinheim, 1994); Hayat, M. A. (ed.) Colloidal Gold: Principles, Methods, and Applications (Academic Press, San Diego, 1991); Massart, R., IEEE Transactions On Magnetics, 17, 1247 (1981); Ahmadi, T. S. et al., Science, 272, 1924 (1996); Henglein, A. et al., J. Phys. Chem., 99, 14129 (1995); Curtis, A. C., et al., Angew. Chem. Int. Ed. Engl., 27, 1530 (1988). Preparation of polyalkylcyanoacrylate nanoparticles prepared is described in Fattal, et al., J. Controlled Release (1998) 53: 137-143 and U.S. Pat. No. 4,489,055. Methods for making nanoparticles comprising poly(D-glucaramidoamine)s are described in Liu, et al., J. Am. Chem. Soc. (2004) 126:7422-7423. Preparation of nanoparticles comprising polymerized methylmethacrylate (MMA) is described in Tondelli, et al., Nucl. Acids Res. (1998) 26:5425-5431, and preparation of dendrimer nanoparticles is described in, for example Kukowska-Latallo, et al., Proc. Natl. Acad. Sci. USA (1996) 93:4897-4902 (Starburst polyamidoamine dendrimers)

Also as described in US patent application No 20030147966, nanoparticles comprising materials described herein are available commercially from, for example, Ted Pella, Inc. (gold), Amersham Corporation (gold) and Nanoprobes, Inc. (gold), or they can be produced from progressive nucleation in solution (e.g., by colloid reaction), or by various physical and chemical vapor deposition processes, such as sputter deposition. See, e.g., HaVashi, (1987) Vac. Sci. Technol. July/August 1987, A5(4):1375-84; Hayashi, (1987) Physics Today, December 1987, pp. 44-60; MRS Bulletin, January 1990, pgs. 16-47.

As further described in US patent application No 20030147966, nanoparticles contemplated are produced using HAuCl4 and a citrate-reducing agent, using methods known in the art. See, e.g., Marinakos et al., (1999) Adv. Mater. 11: 34-37; Marinakos et al., (1998) Chem. Mater. 10: 1214-19; Enustun & Turkevich, (1963) J. Am. Chem. Soc. 85: 3317. Tin oxide nanoparticles having a dispersed aggregate particle size of about 140 nm are available commercially from Vacuum Metallurgical Co., Ltd. of Chiba, Japan. Other commercially available nanoparticles of various compositions and size ranges are available, for example, from Vector Laboratories, Inc. of Burlingame, Calif.

In various aspects, compositions and methods provided include those utilizing nanoparticles which range in size from about 1 nm to about 250 nm in mean diameter, about 1 nm to about 240 nm in mean diameter, about 1 nm to about 230 nm in mean diameter, about 1 nm to about 220 nm in mean diameter, about 1 nm to about 210 nm in mean diameter, about 1 nm to about 200 nm in mean diameter, about 1 nm to about 190 nm in mean diameter, about 1 nm to about 180 nm in mean diameter, about 1 nm to about 170 nm in mean diameter, about 1 nm to about 160 nm in mean diameter, about 1 nm to about 150 nm in mean diameter, about 1 nm to about 140 nm in mean diameter, about 1 nm to about 130 nm in mean diameter, about 1 nm to about 120 nm in mean diameter, about 1 nm to about 110 nm in mean diameter, about 1 nm to about 100 nm in mean diameter, about 1 nm to about 90 nm in mean diameter, about 1 nm to about 80 nm in mean diameter, about 1 nm to about 70 nm in mean diameter, about 1 nm to about 60 nm in mean diameter, about 1 nm to about 50 nm in mean diameter, about 1 nm to about 40 nm in mean diameter, about 1 nm to about 30 nm in mean diameter, or about 1 nm to about 20 nm in mean diameter, about 1 nm to about 10 nm in mean diameter. In other aspects, the size of the nanoparticles is from about 5 nm to about 150 nm (mean diameter), from about 5 to about 50 nm, from about 10 to about 30 nm. The size of the nanoparticles is from about 5 nm to about 150 nm (mean diameter), from about 30 to about 100 nm, from about 40 to about 80 nm. The size of the nanoparticles used in a method varies as required by their particular use or application. The variation of size is advantageously used to optimize certain physical characteristics of the nanoparticles, for example, optical properties or amount of surface area that can be derivatized as described herein.

Core-Shell Nanoparticle Synthesis

The polynucleotide can be modified at a terminus with an alkyne moiety, e.g., a DBCO-type moiety for reaction with the azide of the protein surface:

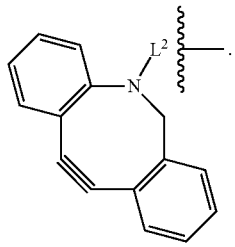

where L is a linker to a terminus of the polynucleotide. $L^2$ can be $C_{1-10}$ alkylene, —C(O)—$C_{1-10}$ alkylene-Y—, and —C(O)—$C_{1-10}$ alkylene-Y—$C_{1-10}$ alkylene-(OCH$_2$CH$_2$)$_m$—Y—; wherein each Y is independently selected from the group consisting of a bond, C(O), O, NH, C(O)NH, and NHC(O); and m is 0, 1, 2, 3, 4, or 5. For example, the DBCO functional group can be attached via a linker having a structure of

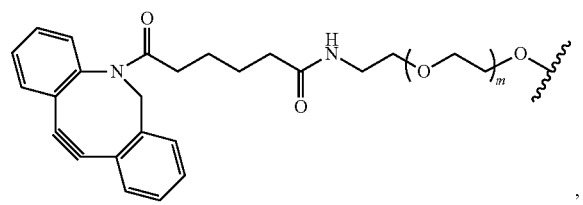

where the terminal "O" is from a terminal nucleotide on the polynucleotide. Use of this DBCO-type moiety results in a structure between the polynucleotide and the protein, in cases where a surface amine is modified, of:

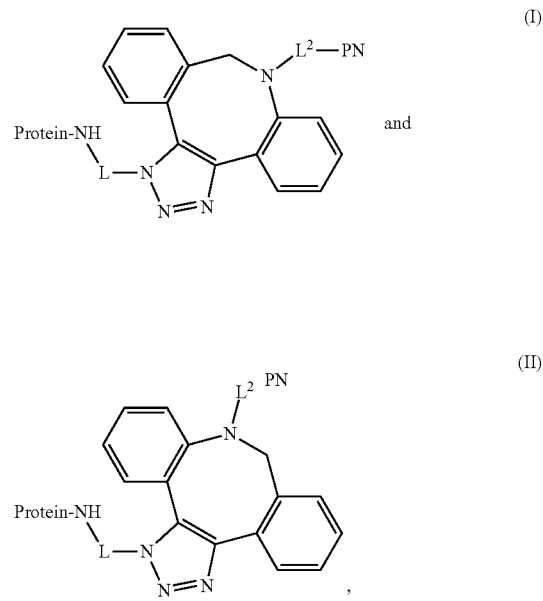

where L and $L^2$ are each independently selected from $C_{1-10}$ alkylene, —C(O)—$C_{1-10}$ alkylene-Y—, and —C(O)—$C_{1-10}$ alkylene-Y—$C_{1-10}$ alkylene-(OCH$_2$CH$_2$)$_m$—Y—; each Y is independently selected from the group consisting of a bond, C(O), O, NH, C(O)NH, and NHC(O); m is 0, 1, 2, 3, 4, or 5; and PN is the polynucleotide. Similar structures where a surface thiol or surface carboxylate of the protein are modified can be made in a similar fashion to result in comparable linkage structures.

The protein can be modified at a surface functional group (e.g., a surface amine, a surface carboxylate, a surface thiol) with a linker that terminates with an azide functional group: Protein-X-L-N$_3$, X is from a surface amino group (e.g., —NH—), carboxylic group (e.g., —C(O)— or —C(O)O—), or thiol group (e.g., —S—) on the protein; L is selected from $C_{1-10}$ alkylene, —Y—C(O)—$C_{1-10}$ alkylene-Y—, and —Y—C(O)—$C_{1-10}$ alkylene-Y—$C_{1-10}$ alkylene-(OCH$_2$CH$_2$)$_m$—Y—; each Y is independently selected from the group consisting of a bond, C(O), O, NH, C(O)NH, and NHC(O); and m is 0, 1, 2, 3, 4, or 5. Introduction of the "L-N$_3$" functional group to the surface moiety of the protein can be accomplished using well-known techniques. For example, a surface amine of the protein can be reacted with an activated ester of a linker having a terminal N$_3$ to form an amide bond between the amine of the protein and the carboxylate of the activated ester of the linker reagent.

The polynucleotide can be modified to include an alkyne functional group at a terminus of the polynucleotide: Polynucleotide-L$_2$-X—≡—R; $L^2$ is selected from $C_{1-10}$ alkylene, —C(O)—$C_{1-10}$ alkylene-Y—, and —C(O)—$C_{1-10}$ alkylene-Y—$C_{1-10}$ alkylene-(OCH$_2$CH$_2$)$_m$—Y—; each Y is independently selected from the group consisting of a bond, C(O), O, NH, C(O)NH, and NHC(O); m is 0, 1, 2, 3, 4, or 5; and X is a bond and R is H or $C_{1-10}$alkyl; or X and R together with the carbons to which they are attached form a 8-10 membered carbocyclic or 8-10 membered heterocyclic group. In some cases, the polynucleotide has a structure

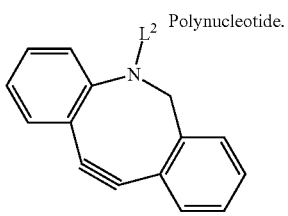

The protein, with the surface modified azide, and the polynucleotide, with a terminus modified to include an alkyne, can be reacted together to form a triazole ring in the presence of a copper (II) salt and a reducing agent to generate a copper (I) salt in situ. In some cases, a copper (I) salt is directly added. Contemplated reducing agents include ascorbic acid, an ascorbate salt, sodium borohydride, 2-mercaptoethanol, dithiothreitol (DTT), hydrazine, lithium aluminum hydride, diisobutylaluminum hydride, oxalic acid, Lindlar catalyst, a sulfite compound, a stannous compound, a ferrous compound, sodium amalgam, tris(2-carboxyethyl) phosphine, hydroquinone, and mixtures thereof.

The surface functional group of the protein can be attached to the polynucleotide using other attachment chemistries. For example, a surface amine can be directed conjugated to a carboxylate or activated ester at a terminus of the polynucleotide, to form an amide bond. A surface carboxylate can be conjugated to an amine on a terminus of the polynucleotide to form an amide bond. Alternatively, the surface carboxylate can be reacted with a diamine to form an amide bond at the surface carboxylate and an amine at the other terminus. This terminal amine can then be modified in a manner similar to that for a surface amine of the protein. A surface thiol can be conjugated with a thiol moiety on the polynucleotide to form a disulfide bond. Alternatively, the thiol can be conjugated with an activated ester on a terminus of a polynucleotide to form a thiocarboxylate.

Pharmaceutical Compositions

It will be appreciated that any of the compositions described herein may be administered to a mammal in a therapeutically effective amount to achieve a desired therapeutic effect.

The term "therapeutically effective amount", as used herein, refers to an amount of a composition sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by an assay described herein. The precise effective amount for a subject will depend upon the subject's body weight, size, and health; the nature and extent of the condition; and the composition or combination of compositions selected for administration. Therapeutically effective amounts for a given situation can be determined by routine experimentation that is within the skill and judgment of the clinician. The compositions described herein may be formulated in pharmaceutical compositions with a pharmaceutically acceptable excipient, carrier, or diluent. The compound or composition can be administered by any route that permits treatment of a disease, disorder or infection. A preferred route of administration is oral administration.

Compositions of Multiple Core-Shell Particles

Further disclosed herein are compositions comprising a plurality of core-shell particles. In some cases, at least one polynucleotide of one core-shell particle and at least one polynucleotide of a second core-shell particle are sufficiently complementary to hybridize to form a superlattice structure. In various cases, the protein of the core of one core-shell particle is different from the protein of the core of a second core-shell particle. In other cases, the protein of the core of all the core-shell particles of the plurality are the same.

In various cases, the core-shell particles of the composition can non-covalently interact (e.g., via hybridization of complementary polynucleotides of the shells) or covalently interact (e.g., via direct bond formation between compatible reactive functional moieties of the polynucleotides) to form a superlattice structure. In other cases, the plurality of core-shell nanoparticles do not covalently or non-covalently interact but are merely within the same composition.

In various cases, one core-shell particle can comprise an enzyme for a chemical reaction, and a second core-shell particle can comprise a second enzyme for a second chemical reaction. In further cases, one or more additional core-shell particles comprise additional enzyme(s), which are either the same or different than the enzymes present in the first and/or second core-shell particles.

Methods of Use

Methods of Detecting a Target Polynucleotide

The disclosure provides methods of detecting a target molecule (e.g., a target polynucleotide) comprising contacting the target molecule with a core-shell nanoparticle as described herein. The contacting results, in various aspects, in regulation of gene expression as provided by the disclosure. In another aspect, the contacting results in a detectable change, wherein the detectable change indicates the detection of the target molecule. Detection of the detectable label is performed by any of the methods described herein, and the detectable label can be on a molecule that is part of a core-shell nanoparticle, or can be on the target molecule.

In various aspects, the methods include use of a polynucleotide which is 100% complementary to a target polynucleotide, i.e., a perfect match, while in other aspects, the polynucleotide is at least (meaning greater than or equal to) about 95% complementary to the polynucleotide over the length of the polynucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the polynucleotide to the extent that the polynucleotide is able to achieve the desired inhibition of a target gene product.

In some embodiments, the core-shell nanoparticles of the disclosure are useful in nano-flare technology. The nano-flare has been previously described in the context of polynucleotide-functionalized nanoparticles for fluorescent detection of target molecule levels inside a living cell [described in WO 2008/098248, incorporated by reference herein in its entirety]. In this system the "flare" is detectably labeled and displaced or released from the core-shell nanoparticle by an incoming target polynucleotide. It is thus contemplated that the nano-flare technology is useful in the context of the core-shell nanoparticles described herein.

Target Molecules

It is contemplated by the disclosure that any of the compositions described herein can be used to detect a target molecule. In various aspects, the target molecule is a polynucleotide, and the polynucleotide is either eukaryotic, prokaryotic, or viral. The target molecule may be in cells, tissue samples, or biological fluids, as also known in the art.

If a polynucleotide is present in small amounts, it may be amplified by methods known in the art. See, e.g., Sambrook et al., Molecular Cloning: A Laboratory Manual (2nd ed. 1989) and B. D. Hames and S. J. Higgins, Eds., Gene Probes 1 (IRL Press, New York, 1995). Generally, but without limitation, polymerase chain reaction (PCR) amplification can be performed to increase the concentration of a target nucleic acid to a degree that it can be more easily detected.

In various embodiments, methods provided include those wherein the target polynucleotide is a mRNA encoding a gene product and translation of the gene product is inhibited, or the target polynucleotide is DNA in a gene encoding a gene product and transcription of the gene product is inhibited. In methods wherein the target polynucleotide is DNA, the polynucleotide is in certain aspects DNA which encodes the gene product being inhibited. In other methods, the DNA is complementary to a coding region for the gene product. In still other aspects, the DNA encodes a regulatory element necessary for expression of the gene product. "Regulatory elements" include, but are not limited to enhancers, promoters, silencers, polyadenylation signals, regulatory protein binding elements, regulatory introns, and/or ribosome entry sites. In still another aspect, the target polynucleotide is a sequence which is required for endogenous replication. In further embodiments, the target molecule is a microRNA (miRNA).

Methods of Inhibiting Gene Expression

Additional methods provided by the disclosure include methods of inhibiting expression of a gene product expressed from a target polynucleotide comprising contacting the target polynucleotide with a core-shell nanoparticle or composition as described herein, wherein the contacting is sufficient to inhibit expression of the gene product. Inhibition of the gene product results from the hybridization of a target polynucleotide with a core-shell nanoparticle or composition of the disclosure.

It is understood in the art that the sequence of a polynucleotide that is part of a core-shell nanoparticle need not be 100% complementary to that of its target polynucleotide in order to specifically hybridize to the target polynucleotide. Moreover, a polynucleotide that is part of a core-shell nanoparticle may hybridize to a target polynucleotide over one or more segments such that intervening or adjacent segments are not involved in the hybridization event (for example and without limitation, a loop structure or hairpin structure). The percent complementarity is determined over the length of the polynucleotide that is part of the core-shell nanoparticle. For example, given a core-shell nanoparticle comprising a polynucleotide in which 18 of 20 nucleotides of the polynucleotide are complementary to a 20 nucleotide region in a target polynucleotide of 100 nucleotides total length, the polynucleotide that is part of the core-shell nanoparticle would be 90 percent complementary. In this example, the remaining noncomplementary nucleotides may be clustered or interspersed with complementary nucleotides and need not be contiguous to each other or to complementary nucleotides. Percent complementarity of a polynucleotide that is part of a core-shell nanoparticle with a region of a target polynucleotide can be determined routinely using BLAST programs (basic local alignment search tools) and PowerBLAST programs known in the art (Altschul et al., J. Mol. Biol., 1990, 215, 403-410; Zhang and Madden, Genome Res., 1997, 7, 649-656).

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a core-shell nanoparticle. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in vitro in a cell culture assay, generally as a predictable measure of a degree of inhibition that can be expected in vivo resulting from use of a composition as described herein. It is contemplated by the disclosure that the inhibition of a target polynucleotide is used to assess the effects of the inhibition on a given cell. By way of non-limiting examples, one can study the effect of the inhibition of a gene product wherein the gene product is part of a signal transduction pathway. Alternatively, one can study the inhibition of a gene product wherein the gene product is hypothesized to be involved in an apoptotic pathway.

It will be understood that any of the methods described herein can be used in combination to achieve a desired result. For example and without limitation, methods described herein can be combined to allow one to both detect a target polynucleotide as well as regulate its expression. In some embodiments, this combination can be used to quantitate the inhibition of target polynucleotide expression over time either in vitro or in vivo. The quantitation over time is achieved, in one aspect, by removing cells from a culture at specified time points and assessing the relative level of expression of a target polynucleotide at each time point. A decrease in the amount of target polynucleotide as assessed, in one aspect, through visualization of a detectable label, over time indicates the rate of inhibition of the target polynucleotide.

Thus, determining the effectiveness of a given polynucleotide to hybridize to and inhibit the expression of a target polynucleotide, as well as determining the effect of inhibition of a given polynucleotide on a cell, are aspects that are contemplated.

Methods of Catalyzing a Reaction

Provided herein are methods of using the disclosed core-shell particles or complexes of the same as catalysts for a chemical reaction to transform one or more reagents to a product. The methods can comprise contacting the one or more reagents of the reaction with a composition of a plurality of core-shell particles as disclosed herein such that contact of the reagent or reagents with the composition results in the reaction being catalyzed to form a product of the reaction, wherein the protein of the core-shell particle is an enzyme for the chemical reaction.

EXAMPLES

Example 1

Synthesizing Protein/Oligonucleotide Core-Shell Nanoparticles

Materials and instrumentation: Bovine catalase was purchased from Sigma and used as provided. NHS-PEG$_4$-azide was purchased from Thermo Scientific and modified phosphoramidites from Glen Research. C8S astrocytes were obtained from ATCC. Oligonucleotides were synthesized on a MerMade 48 (MM48) automated oligonucleotide synthesizer (BioAutomation). The oligonucleotides were deprotected by incubation in aqueous NaOH (DBCO-containing oligonucleotides) or 0.05 M potassium carbonate in methanol (Cy5-containing oligonucleotides) for 12 h at room temperature. Deprotected oligonucleotides were purified by reverse-phase HPLC on a Varian Prostar chromatography station, after which their sequences were verified by matrix assisted time of flight mass spectrometry (MALDI-TOF-MS) and their concentrations determined by UV spectroscopy. Circular dichroism (CD) spectra were measured on a Jasco J-18 spectrophotometer. Cell uptake of Cy5-labeled oligonucleotides was monitored by fluorescence confocal microscopy on a Zeiss LSM 510 inverted laser scanning confocal microscope.

Figure 1B:
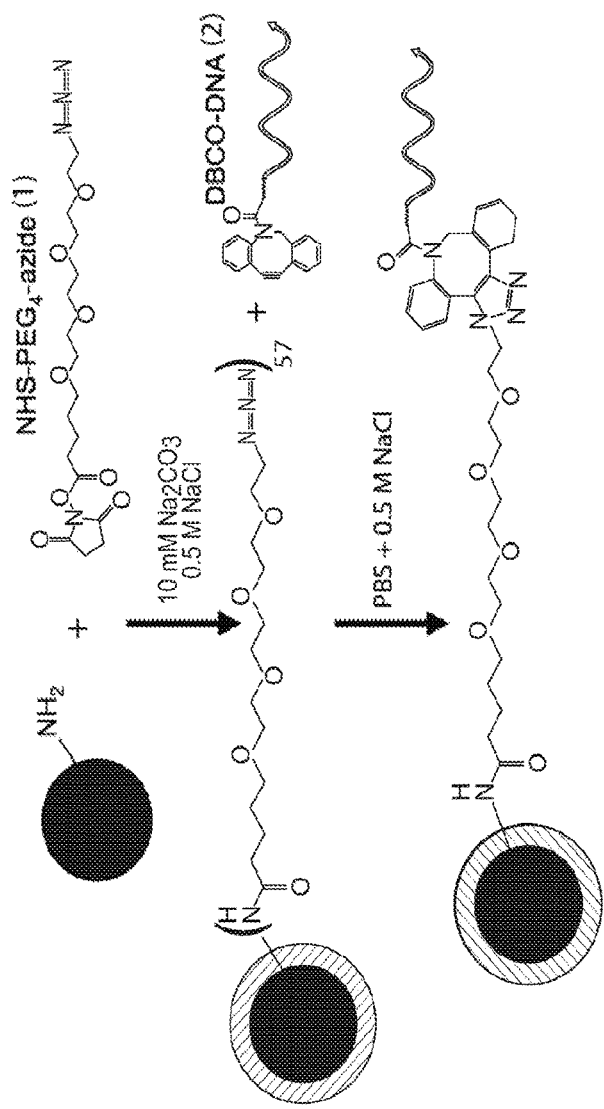
FIGS. 1a-b depicts a strategy for covalent attachment of oligonucleotides to the surface of a protein. (1a) Cartoon representation of bovine catalase. Lysine amino acids, which contain a primary amine, are highlighted as blue sticks. (1b) Reaction scheme for modification of a protein surface with a dense shell of oligonucleotides. Only one surface amine is shown for clarity. Outer circles represent a shell of conjugated azides (middle structure) or DNA (bottom structure).
Figure 1A:
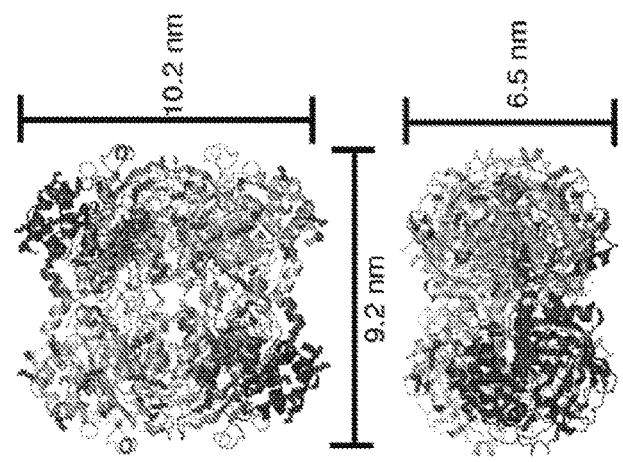
Figure 2:
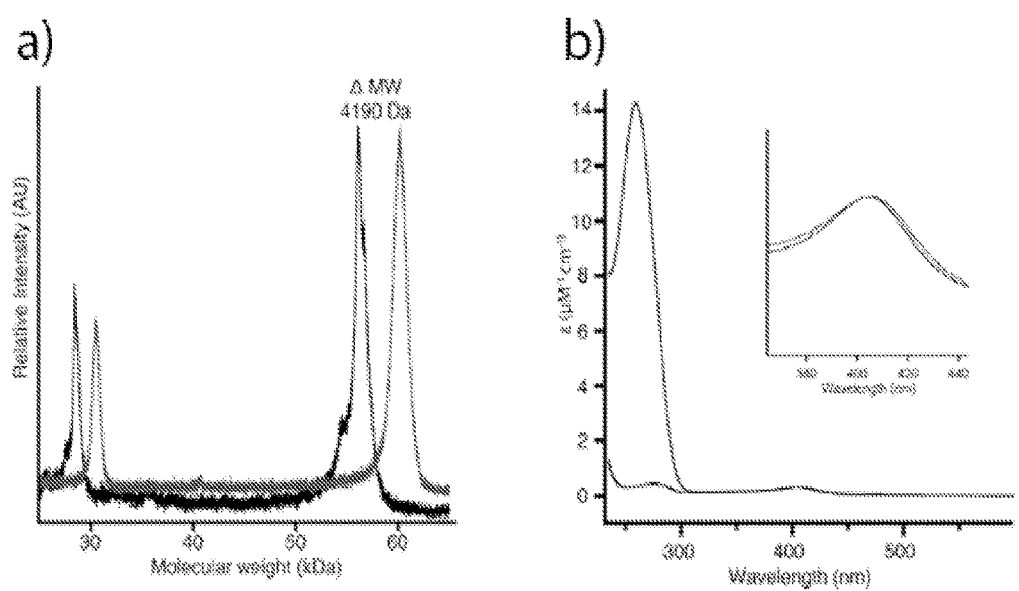
FIGS. 2a-b shows the determination of the extent of surface modification of catalase with (1) (panel a) and (2) (panel b). (2a) MALDI-TOF-MS spectra of native (left spectrum) and azide-labeled (right spectrum) catalase. The difference in molecular weight of 4190 Da corresponds to labeling with approximately 60 eq. of (1). (2b) UV-Vis spectra of native black and DNA-labeled (spectrum showing a peak up to 300 nm) catalase. The difference in absorbance at 260 nm corresponds to covalent attachment of approximately 64 oligonucleotides. The absorbance at 405 nm (inset) was used to determine protein concentration and confirm retention of the protein structure surrounding the active site.

Synthesis of protein/oligonucleotide core-shell nanoparticles: Bovine catalase (FIG. 1a) was modified with a dense shell of oligonucleotides as shown in FIG. 1b. Surface-exposed amines were converted to azides by reaction of 50 µM catalase with 50 mM (1) (FIG. 1) for 2 hours at room temperature. Typical reactions resulted in the conversion of 60+/−1 amines to azides, as determined by MALDI mass spectrometry (FIG. 2a). Azide-modified proteins were covalently modified with the following DNA sequences:

```
                                        (SEQ ID NO: 1)
1)    5' DBCO Sp18₂ AAG AAT TTA TAA GCA GAA
      (260 nm = 199,900 M-1 cm-1)

(SEQ ID NO: 2)
2)    5' DBCO Sp18₂ AAC AAT TAT ACT CAG CAA
      (260 nm = 187,700 M-1 cm-1)
```

Solutions containing 1 µM azide-labeled catalase and 1 mM 5'-DBCO-modified DNA were incubated for three days at room temperature. Excess DNA was then removed from the solution using Amicon Ultra Centrifugal Filter Units (Millipore), after which the extent of labeling with DNA was determined as follows. First, the enzyme concentration was determined according to Beer's law and a molar absorptivity of 324,000 M$^{-1}$ cm$^{-1}$ at 405 nm. The extent of labeling with DNA was then determined by measuring the change in absorbance at 260 nm (FIG. 2b). Typical reactions yielded approximately 60-70 oligonucleotides/protein. The slight excess of oligonucleotides compared to the number of azides is likely due to retention of a small number of noncovalently bound oligonucleotides or slight errors in the estimation of the molar absorptivities calculated for the oligonucleotide sequences employed.

Figure 3A:
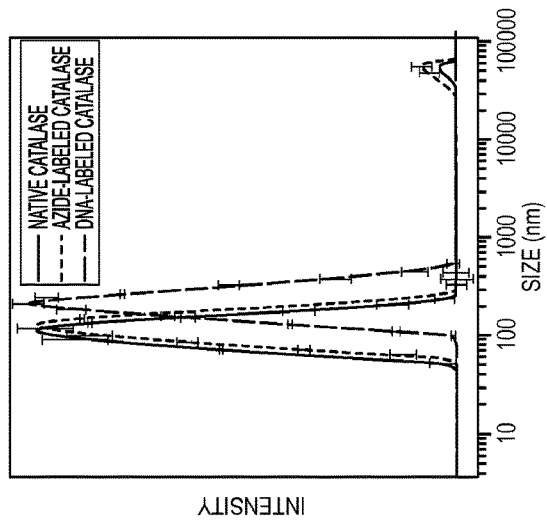
FIGS. 3a-c shows the characterization of protein/DNA core-shell nanoparticles. (3a) Circular dichroism spectra of native, azide- and DNA-labeled catalase. The minima at 208 nm and 222 nm correspond to the helical structure of the protein. Minor differences in the spectrum after covalent attachment of DNA are due to the characteristic CD signature of the appended DNA strands. (3b) Enzyme assay of catalase measuring the decomposition of $H_2O_2$ to $H_2O$ and $O_2$. (3c) Dynamic light scattering spectra of native, azide- and DNA-labeled catalase.
Figure 3B:
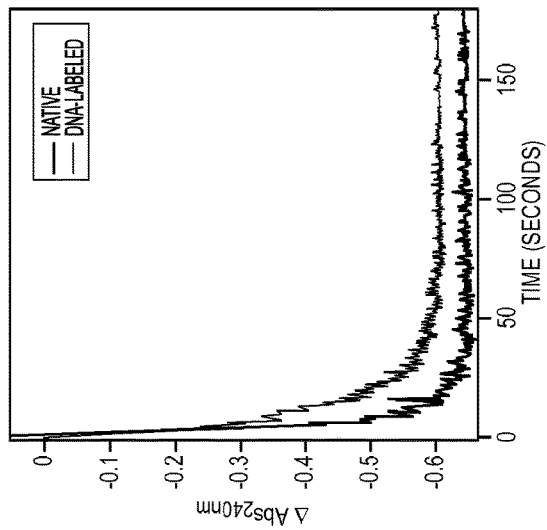
Figure 3C:
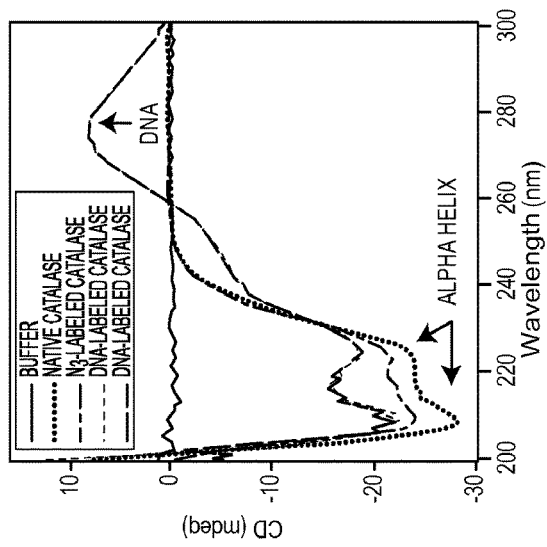

Characterization of protein/oligonucleotide core-shell nanoparticles. The retention of the secondary structure of bovine catalase upon covalent attachment of N3-PEG-azide and DNA was monitored by CD spectroscopy. All spectra were measured using solutions containing 1 µM catalase (FIG. 3a). The enzymatic activity of native and DNA-labeled catalase was monitored by following the decomposition of H$_2$O$_2$ (FIG. 3b). Confirmation of covalent attachment of oligonucleotides to the surface of catalase was followed by measuring changes in the size of the enzyme by DLS (FIG. 3c). A shift from approximately 11 nm to approximately 25 nm is consistent with covalent attachment of a single layer of oligonucleotides to the surface of the enzyme.

Figure 4:
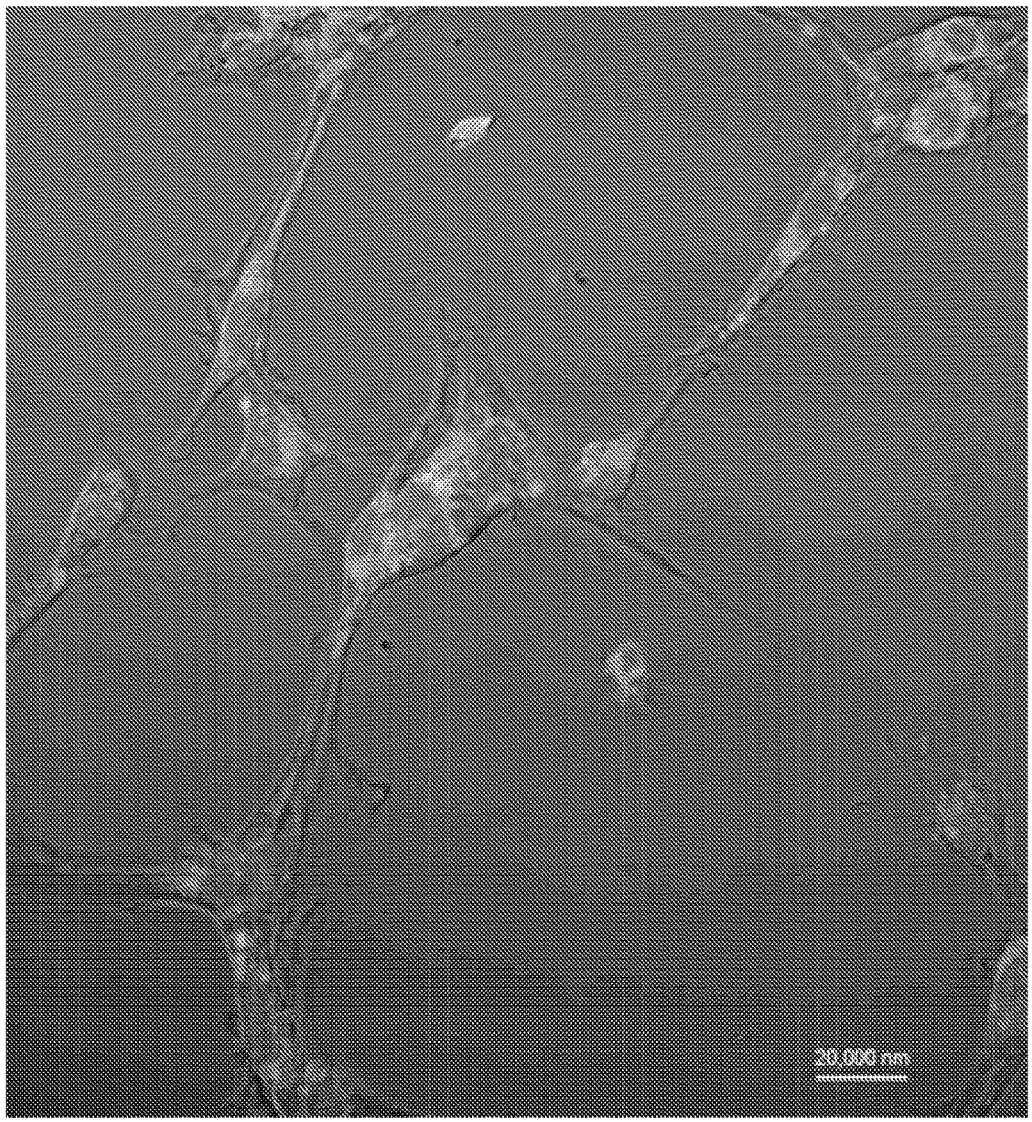
FIG. 4 depicts a fluorescence micrograph of C8S cells showing uptake of catalase labeled with approximately 1.5 FITC molecules and approximately 50 Cy5-containing oligonucleotides.

Cell uptake of protein/DNA core-shell nanoparticles. Prior to modification with DNA, catalase was labeled with approximately 1.5 FITC molecules. This conjugate was then labeled with a T20 oligonucleotide containing 5' DBCO and internal Cy5 phosphoramidites, as described above (SEQ ID NO: 3). The dual labeling strategy allowed for the tracking of the cellular fate of both the protein core and oligonucleotide shell upon cellular uptake. Protein transfection experiments were performed using C8S cells (ATCC, VA, USA) cultured according to the ATCC cell culture guidelines with 10% heat inactivated fetal bovine serum and maintained at 37° C. in 5% CO$_2$. Prior to addition of catalase, cells were transferred to serum free media and incubated with 1 nM protein/DNA core-shell nanoparticles for 4 hours, after which uptake of core-shell nanoparticles was measured by fluorescence confocal microscopy (FIG. 4).

Example 2

Synthesizing Additional Protein/Oligonucleotide Core-Shell Nanoparticles

Materials and instrumentation. All enzymes were purchased from Sigma and used as provided. NHS-PEG4-azide was purchased from Thermo Scientific and modified phosphoramidites from Glen Research. Oligonucleotides were synthesized on a MerMade 48 (MM48) automated oligonucleotide synthesizer (BioAutomation). The oligonucleotides were deprotected by incubation in aqueous NaOH. Deprotected oligonucleotides were then purified by reverse-phase HPLC on a Varian Prostar chromatography station, after which their sequences were verified by matrix assisted time of flight mass spectrometry (MALDI-TOF-MS) and their concentrations determined by UV spectroscopy. Circular dichroism (CD) spectra were measured on a Jasco J-18 spectrophotometer. Small angle X-ray scattering experiments were performed at Argonne National Labs using the DuPont—Northwestern Down Collaborative Access Team beamline. Scanning electron microscopy (SEM) was performed on a Hitachi S4800-II cFEG SEM and scanning transmission electron microscopy (STEM) micrographs were collected using a Hitachi HD-2300 STEM.

Figure 5:
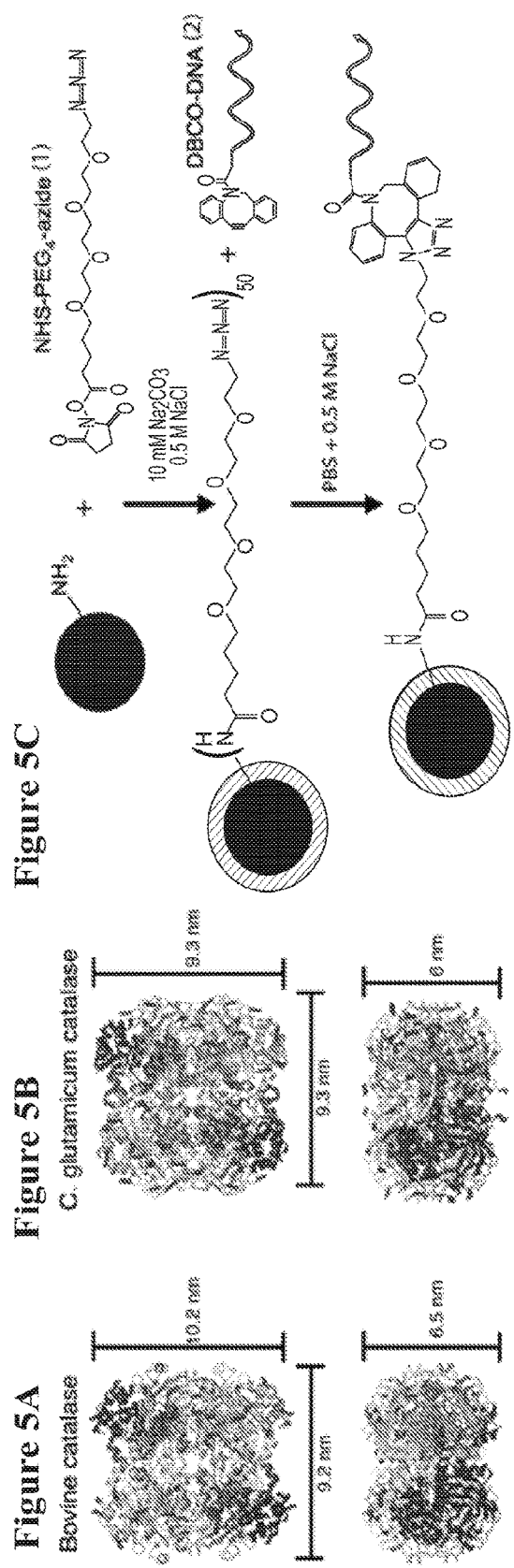
FIGS. 5a-c depicts the strategy for covalent attachment of oligonucleotides to the surface of a protein. (5a) Cartoon representation of bovine catalase. Lysine amino acids, which contain a primary amine, are highlighted. (5b) Cartoon representation of *Corynebacterium glutamicum* ("Cg") catalase. (5c) Reaction scheme for modification of a protein surface with a dense shell of oligonucleotides. Only one surface amine is shown for clarity. Outer circles represent a shell of conjugated azides (middle structure) or DNA (bottom structure).

Synthesis of protein/oligonucleotide core-shell nanoparticles: Bovine catalase and Cg catalase (FIGS. 5a and 5b) were modified with a dense shell of oligonucleotides as shown in FIG. 5c. Surface-exposed amines were converted to azides by reaction of 50 µM catalase with 50 mM (1) for 2 hours at room temperature. Typical reactions resulted in the conversion of 60 or 48 amines to azides for bovine and Cg catalase, respectively, as determined by MALDI mass spectrometry (FIG. 2a). Azide-modified proteins were covalently modified with the following DNA sequences:

```
                                        (SEQ ID NO: 1)
1)    5' DBCO Sp18₂ AAG AAT TTA TAA GCA GAA
      (ε₂₆₀ ₙₘ = 199,900 M⁻¹ cm⁻¹)

(SEQ ID NO: 2)
```

```
2)  5' DBCO Sp18₂ AAC AAT TAT ACT CAG CAA
    (ε₂₆₀ ₙₘ = 187,700 M⁻¹ cm⁻¹)
                                        (SEQ ID NO: 3)
3)  5' DBCO T₁₀-Cy5-T10
    (ε₂₆₀ ₙₘ = 172,600 M⁻¹ cm⁻¹)
```

DNA labeling reactions containing 1 µM azide-labeled catalase and 1 mM 5'-DBCO-modified DNA were incubated for 3 days at room temperature. Excess DNA was then removed from the solution using Amicon Ultra Centrifugal Filter Units (Millipore), after which the extent of labeling with DNA was determined as follows. First, the enzyme concentration was determined according to Beer's law and a molar absorptivity of 324,000 M−1 cm−1 at 405 nm. The number of DNA molecules per protein was then determined by measuring the change in absorbance at 260 nm (FIG. 2b). Typical reactions yielded approximately 60-70 and 40-50 DNA strands bovine or Cg catalase, respectively. The slight excess of DNA strands compared to the number of azides is likely due to retention of a small number of noncovalently bound DNA strands or slight errors in the molar absorptivities calculated for DNA strands.

Figure 6:
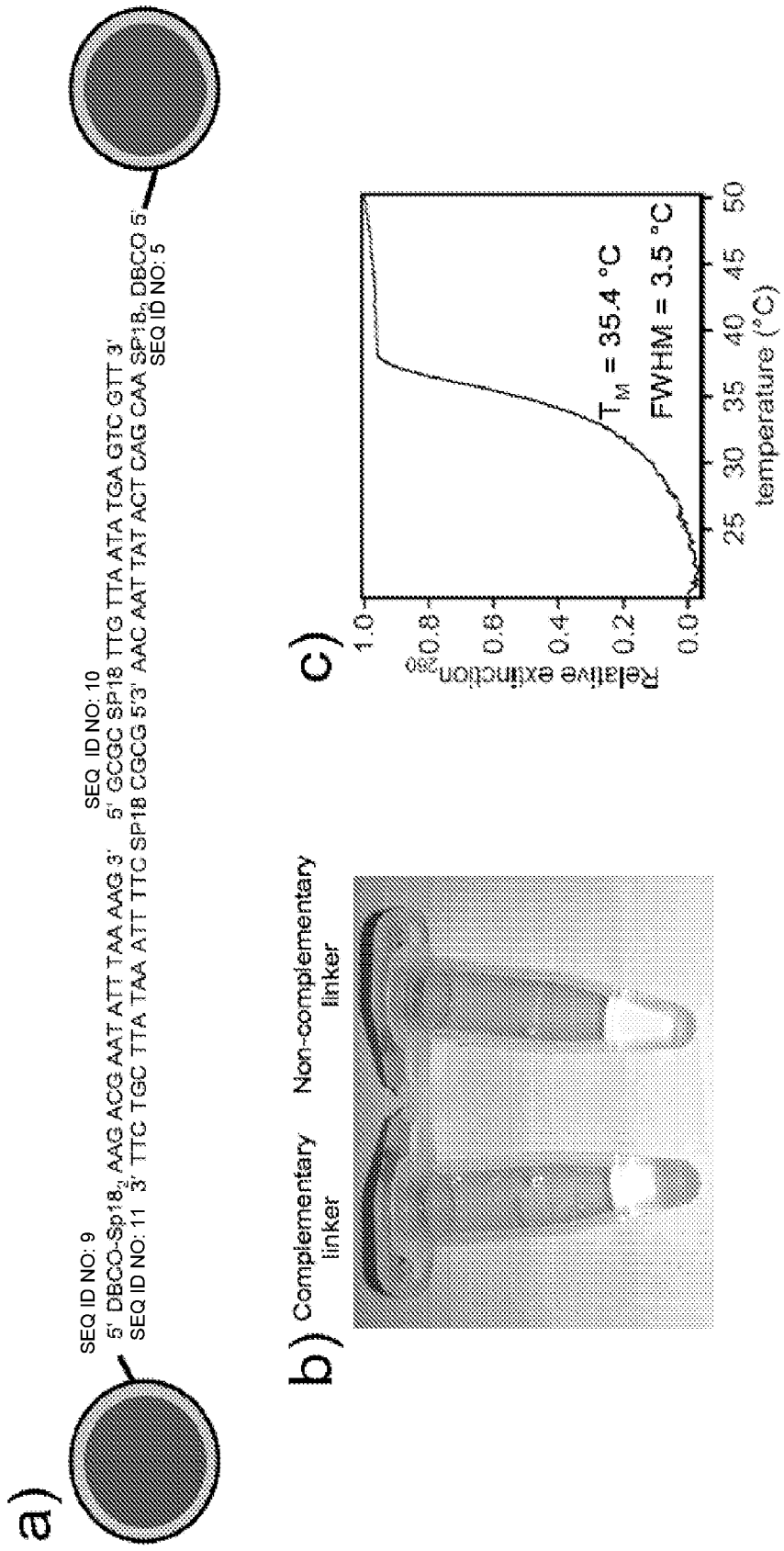
FIGS. 6a-c depicts the assembly of single component protein superlattices. (6a) Scheme for assembly of proteins using self-complementary linkers.

Assembly of DNA-conjugated proteins. Two different types of DNA strands were used for assembly of proteins into higher order structures. First, using self-complementary linkers, a single protein was assembled as shown in FIG. 6. The disassembly of DNA-mediated aggregates was followed by measuring absorbance increases at 260 nm that occur due to the hyperchromatic nature of single stranded DNA relative to DNA duplexes. Sharp melting transitions are characteristic of the multivalent interactions achieved between nanoparticles densely modified with DNA.

Figure 7:
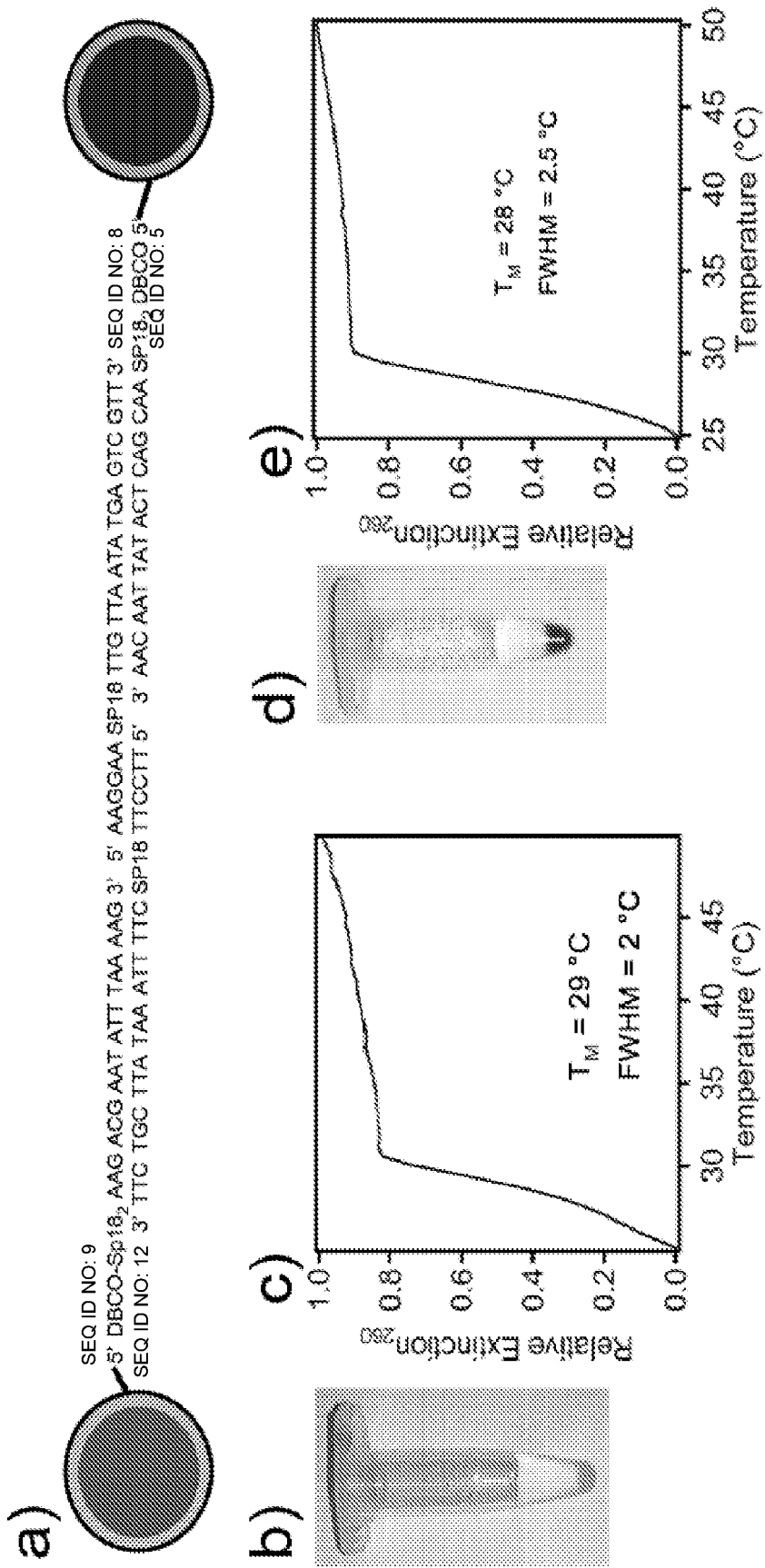
FIGS. 7a-e shows the assembly of binary protein superlattices. (7a) Scheme for assembly of proteins using non-self-complementary linkers.

Using linkers that are complementary to each other, but not themselves, allows the assembly of binary lattices containing either two different enzymes or an enzyme and an AuNP (FIG. 7).

Figure 8:
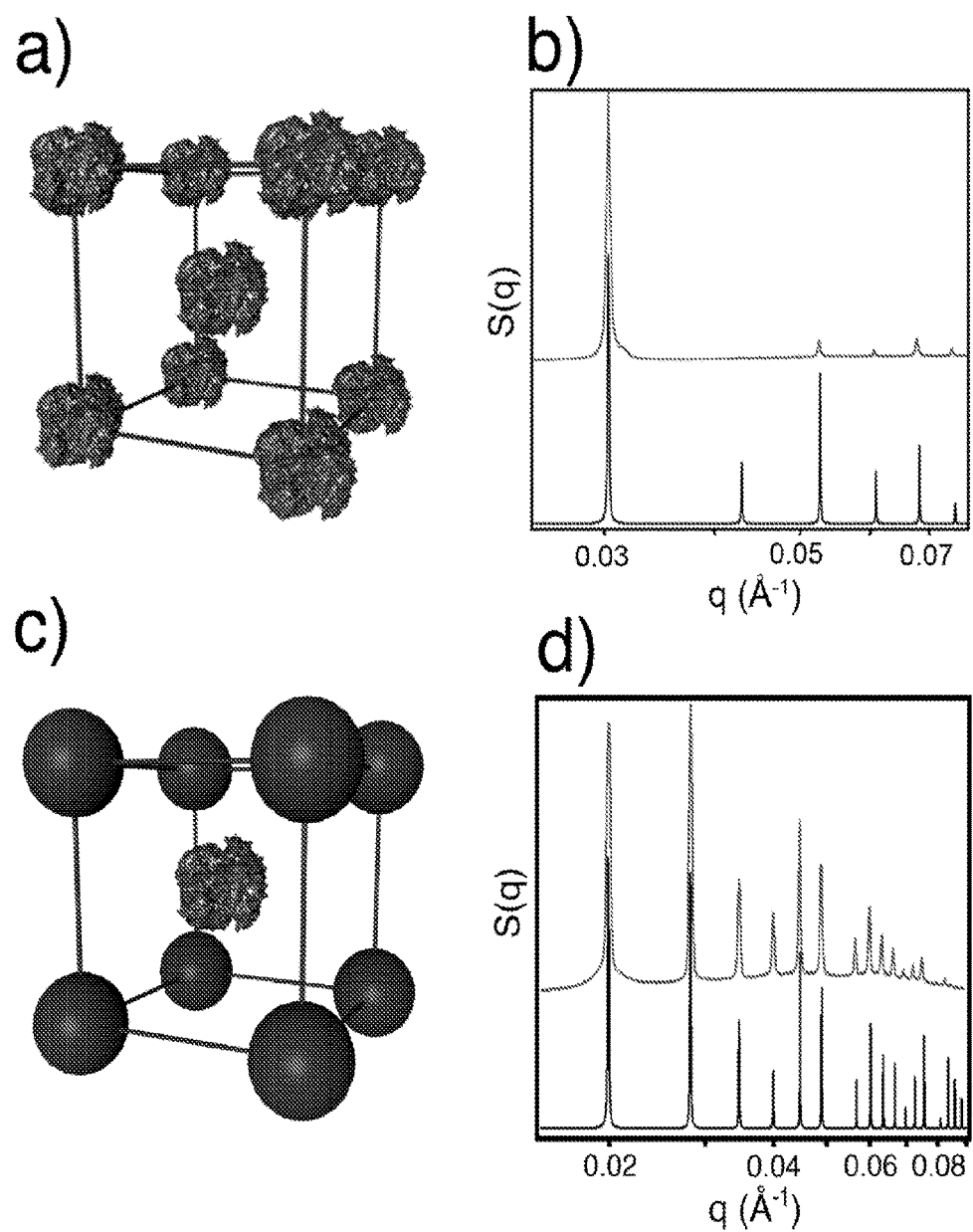
FIGS. 8a-d show the characterization of protein lattices by SAXS.

Formation of protein crystals and characterization of protein superlattices by small angle X-ray scattering (SAXS). Protein crystals were assembled by addition of 100 eq. of linker DNA per protein DNA-conjugate or AuNP. After addition of linker DNA, crystals were formed by heating aggregates above their melting temperature and cooling the sample at a rate of 1° C./10 minutes in a thermal cycler (FIG. 8).

Figure 9:
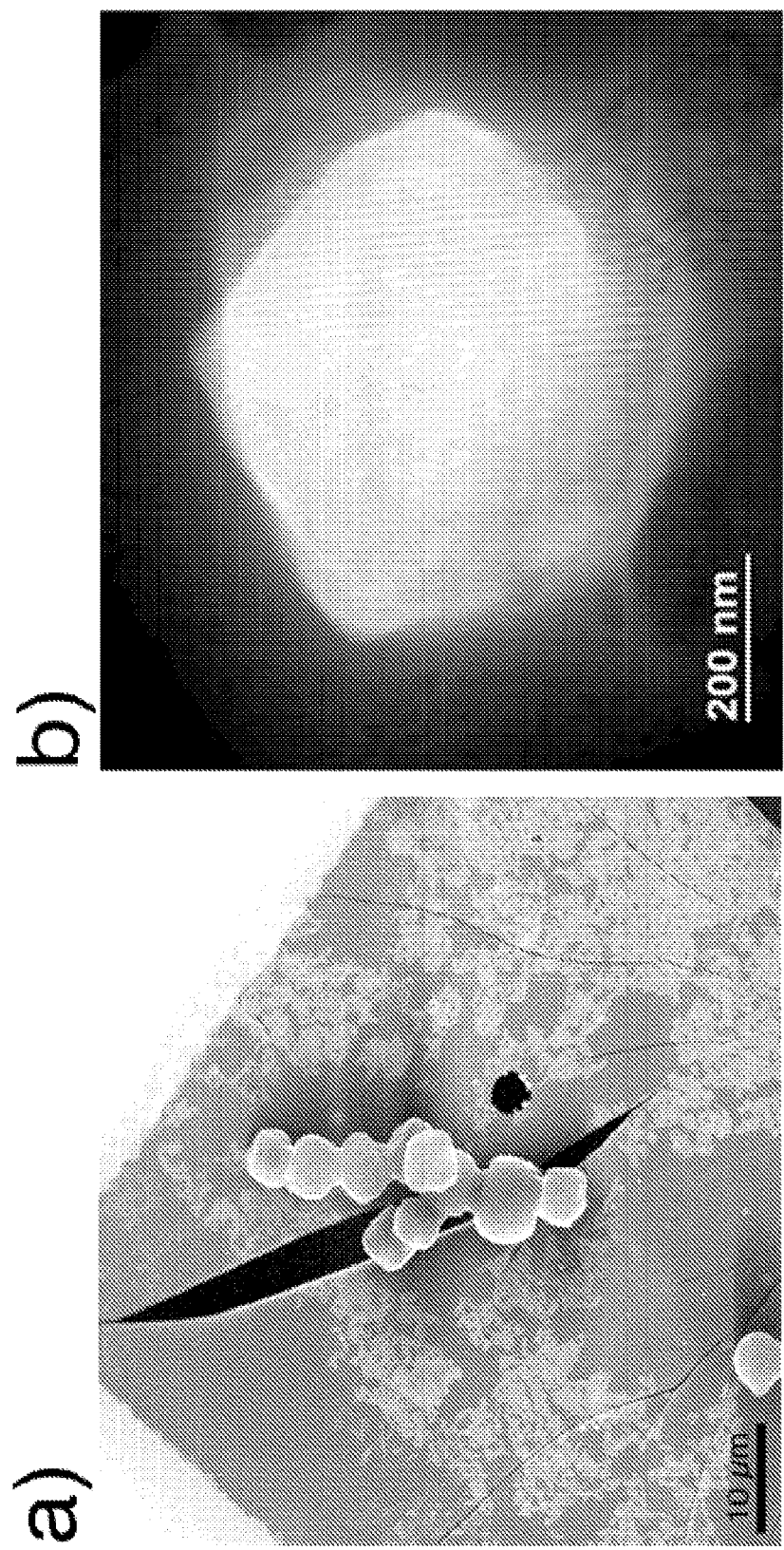
FIG. 9a-b show STEM micrographs of crystals composed of Cg catalase. Low magnification images (9a) were collected in SE mode and higher magnification images (9b) in Z contrast mode.
Figure 10:
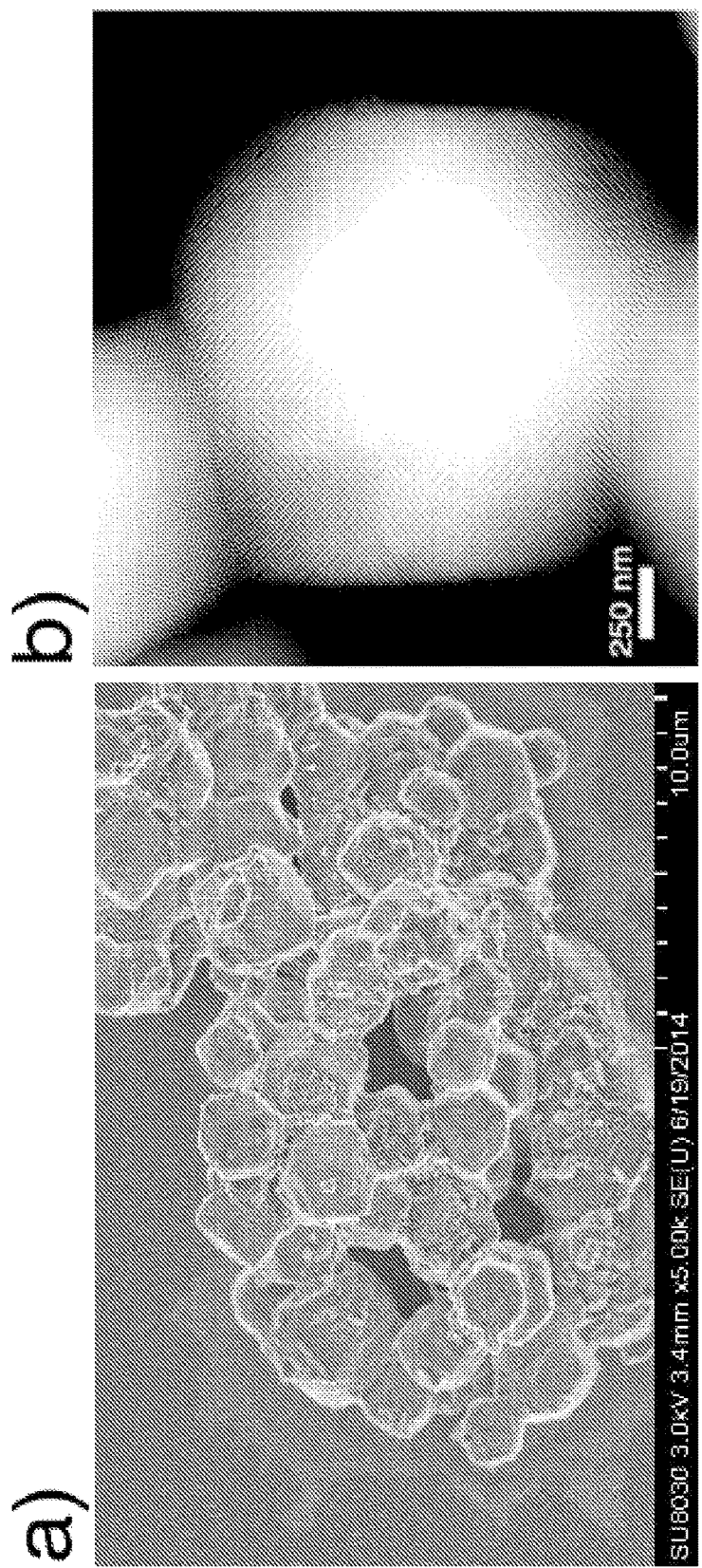
FIGS. 10a-b show STEM micrographs of crystals composed of binary protein-AuNP crystals. Low magnification images (10a) were collected in SE mode and higher magnification images (10b) in Z contrast mode.

Characterization of protein lattices by SEM and STEM. Crystals containing only proteins were prepared for imaging by drop casting a 5 µL aliquot of a crystal-containing solution on a carbon-coated grid and staining with a 2% solution of uranyl acetate (FIG. 9a-b). Binary protein-AuNP crystals were embedded in silica, after which a 5 µL aliquot of the crystal-containing solution was drop cast onto a carbon-coated grid. Images are shown in FIGS. 10a-b.

Example 3

Figure 11:
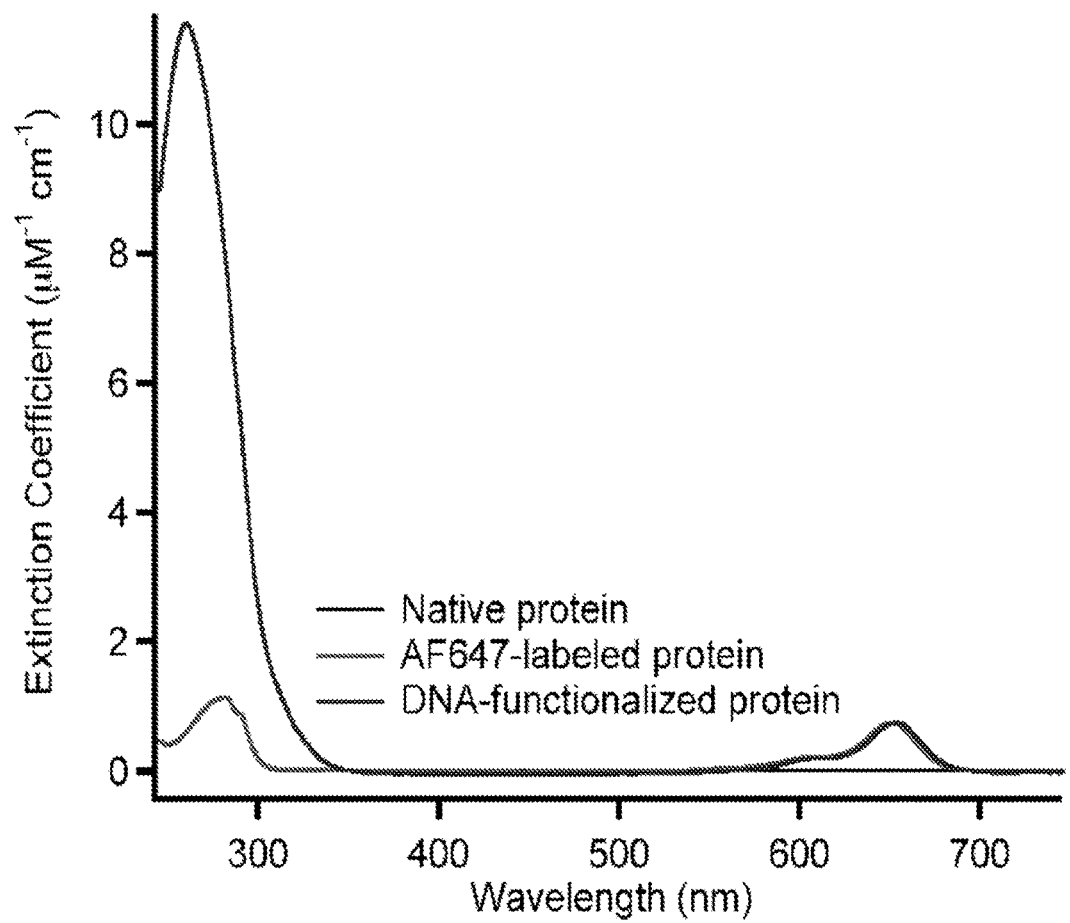
FIG. 11 depicts UV-visible spectroscopy of native, AF647- and DNA-functionalized β-gal. The absorbance peak at approximately 650 nm is from the covalently attached AlexaFluor dyes and was used to measure the concentration of protein after labeling the protein with DNA (top line). The concentration of DNA was determine based on the absorbance at 260 nm.

Synthesizing Beta-Galactosidase Protein/Oligonucleotide Core-Shell Nanoparticles Beta galactosidase (β-gal) was purchased from Sigma and purified by size exclusion chromatography prior to use. The surface of beta galactosidase was modified with polynucleotides essentially as previously described (FIG. 1b) with the following modifications. Prior to modification with azides, β-gal was functionalized with the chromophore, AlexaFluor 647 (Life Technologies) to image cellular trafficking and to provide a handle for determining protein concentration. Reactions containing 9.75 µM protein and 28 µM fluorophore yielded conjugates with approximately 2.6 fluorophores per protein (FIG. 11). β-gal was then modified with azides and subsequently reacted with the polynucleotides, yielding conjugates with approximately 38 DNA strands per protein (FIG. 11).

Functionalization of the surface of β-galactosidase with DNA, as determined by UV-visible absorbance spectroscopy. β-galactosidase was first conjugated to the chromophore, AlexaFluor 647, followed by functionalization with two different DNA sequences. The functionalization yield was determined based on the ratio of absorbance at 647 nm (from the conjugated fluorophore) and 260 nm (from the DNA). Both DNA strands were conjugated to the surface of the enzyme at a ratio of approximately 35:1.

Figure 12:
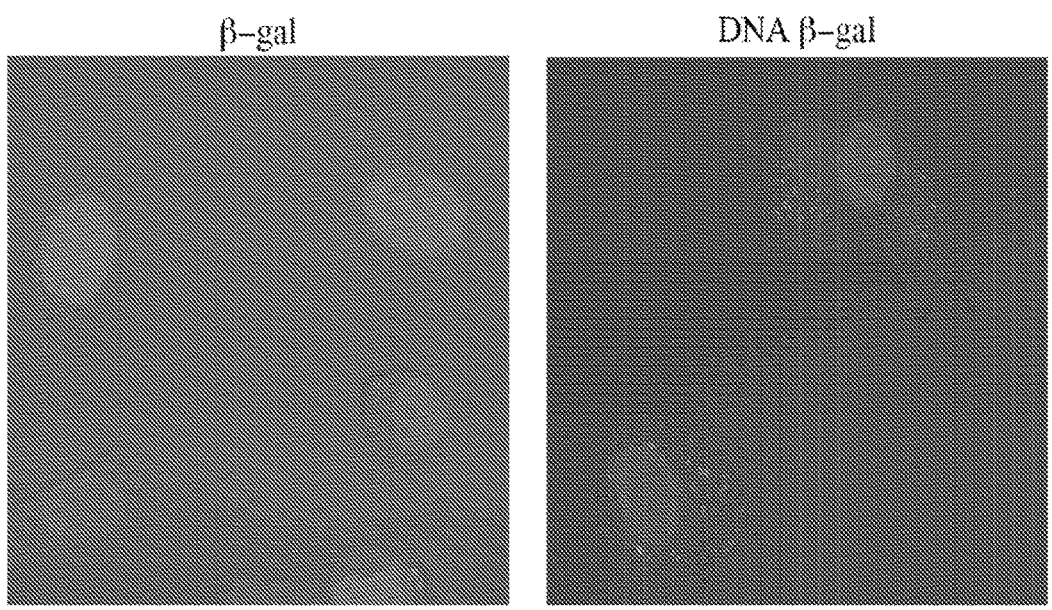
FIG. 12 depicts the cellular uptake of native (left) and DNA-functionalized (right) β-gal determined by confocal fluorescence microscopy. Cellular nuclei were stained with DAPI and are colored blue. The fluorescence signal from the AlexaFluor dyes covalently attached to the surface of the protein is colored red.

Cellular uptake of DNA-modified β-gal was measured by confocal fluorescence microscopy. C8S cells were incubated with 100 nM native- or DNA-modified β-gal for 12 hours, washed with 1×PBS, and imaged by confocal microscopy (FIG. 12). The fluorescent signal originates from the AlexaFluor dyes covalently attached to the surface of the protein, and confirms cellular uptake of DNA-modified β-gal.

Cellular uptake of native and DNA-functionalized β-galactosidase was also determined by flow cytometry in C166, HaCat, and SKOV3 cells. These data demonstrated that the uptake of DNA-functionalized enzymes is enhanced relative to native proteins and that uptake persists across multiple cell lines.

Verification that beta-galactosidase remains folded after functionalization with DNA by circular dichroism spectroscopy. The spectrum of native β-galactosidase and the DNA-functionalized β-galactosidase conjugates were determined. All spectra were corrected for concentration. The decrease in signal at 220 nm was due to contributions from the DNA, and not due to unfolding of the protein. Enzymatic hydrolysis of the fluorogenic beta-galactosidase substrate, Carboxyumbelliferyl β-D-galactopyranoside by native β-galactosidase and the DNA-functionalized β-galactosidase conjugates was also shown.

The catalytic activity of transfected β-gal was determined using a β-gal staining kit (Life Technologies), which measures hydrolysis of the model substrate 5-bromo-4-chloro-3-indolyl-β-D-galactopyranoside (X-gal). Upon hydrolysis, this compound forms a blue precipitate that can be visualized by light microscopy. For these experiments, cells were incubated with 100 nM native- or DNA-modified β-gal for 12 hours, washed with 1×PBS and fixed, after which the assay was performed according to the manufacturer's recommendations. After incubating with X-gal, cells were washed and imaged on a light microscope (FIG. 13), demonstrating the enhanced activity of DNA-functionalized β-gal relative to native β-gal.

Example 4

DNA-Mediated Assembly of Proteins

Materials and methods. All oligonucleotides were synthesized on solid supports on a Mermade 48 (MM48) oligonucleotide synthesizer using reagents obtained from Glen Research and purified by reverse-phase high-performance liquid chromatography (RP-HPLC). Citrate-capped gold nanoparticles (AuNPs) with 10-nm nominal diameters were obtained from Ted Pella and functionalized with DNA as previously described [Park et al., Nature 451(7178): 553-556 (2008); Macfarlane et al., Science 334(6053): 204-208

(2011)]. Briefly, approximately 5 nmol of the appropriate 5'-thiolated oligonucleotide were added per mL of AuNPs, after which sodium dodecyl sulfate (SDS) was added to a final concentration of 0.01% and the resulting solution was incubated for 4 h at room temperature. Aliquots of 5 M NaCl were added to the solution in 0.1 M steps over the course of 3 hours to reach a final concentration of 0.5 M NaCl. This solution was then allowed to incubate overnight at room temperature to maximize DNA loading on the surface of the AuNPs. The DNA-functionalized particles were purified by three rounds of centrifugation at 16000 rpm, followed by resuspension of the resulting pellet in 1 mL of phosphate buffered saline (PBS). Particle concentrations were determined based on UV-visible absorbance spectra (Varian Cary 5000) using a molar extinction coefficient ($\varepsilon_{520}$) of $9.55 \times 10^7$ $M^{-1}$ $cm^{-1}$ (provided by Ted Pella).

Bovine and *Corynebacterium glutamicum* ("Cg") catalases (Sigma) were exchanged into PBS by ultrafiltration (Amicon Ultra, 100 kDa) and their purity confirmed by sodium dodecyl sulfate polyacrylamide gel electrophoresis (SDS-PAGE). Both proteins ran as a single molecular species with the expected molecular weights (approximately 60 kDa/monomer) and were therefore used as received. Prior to chemical functionalization, each protein was concentrated and exchanged into a buffer containing 100 mM sodium bicarbonate (pH 9, 0.5 M NaCl) by ultrafiltration. Protein concentrations were determined by UV-visible absorbance spectroscopy using a molar extinction coefficient ($\varepsilon_{405}$) of 324,000 $M^{-1}$ $cm^{-1}$ [Samejima et al., J Biol Chem 238(10): 3256-61 (1963)].

Figure 15:
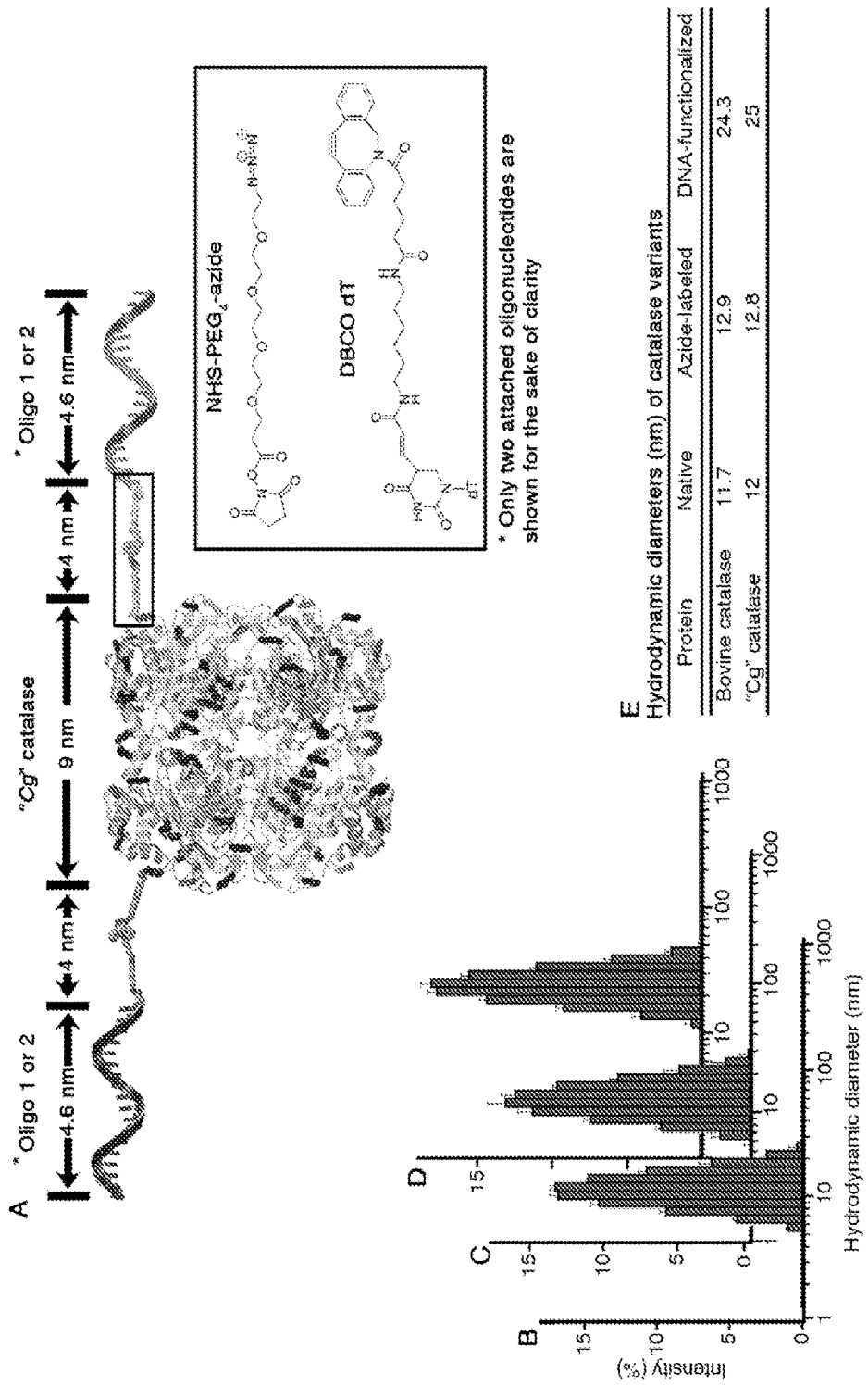
FIGS. 15a-e show the effect of surface modification on the diameter of catalases.

To a 100-µL solution containing 50 µM protein in 100 mM sodium bicarbonate buffer (pH 9, 0.5 M NaCl) was added approximately 6 mg of the linker NHS-PEG4-N3 (Thermo Scientific, FIG. 15, inset). The reaction between surface amines and NHS-PEG4-N3 was allowed to proceed at 25° C. for 2 hours while shaking at 1000 rpm. The azide-functionalized proteins were purified by size exclusion chromatography using NAP10 columns (GE Healthcare) equilibrated with PBS (pH 7.4). The number of attached linkers was determined by matrix assisted laser desorption-ionization mass spectrometry (MALDI-MS) on a Bruker Autoflex III mass spectrometer (FIG. 16) based on an added mass of 274 Da/linker.

Figure 16:
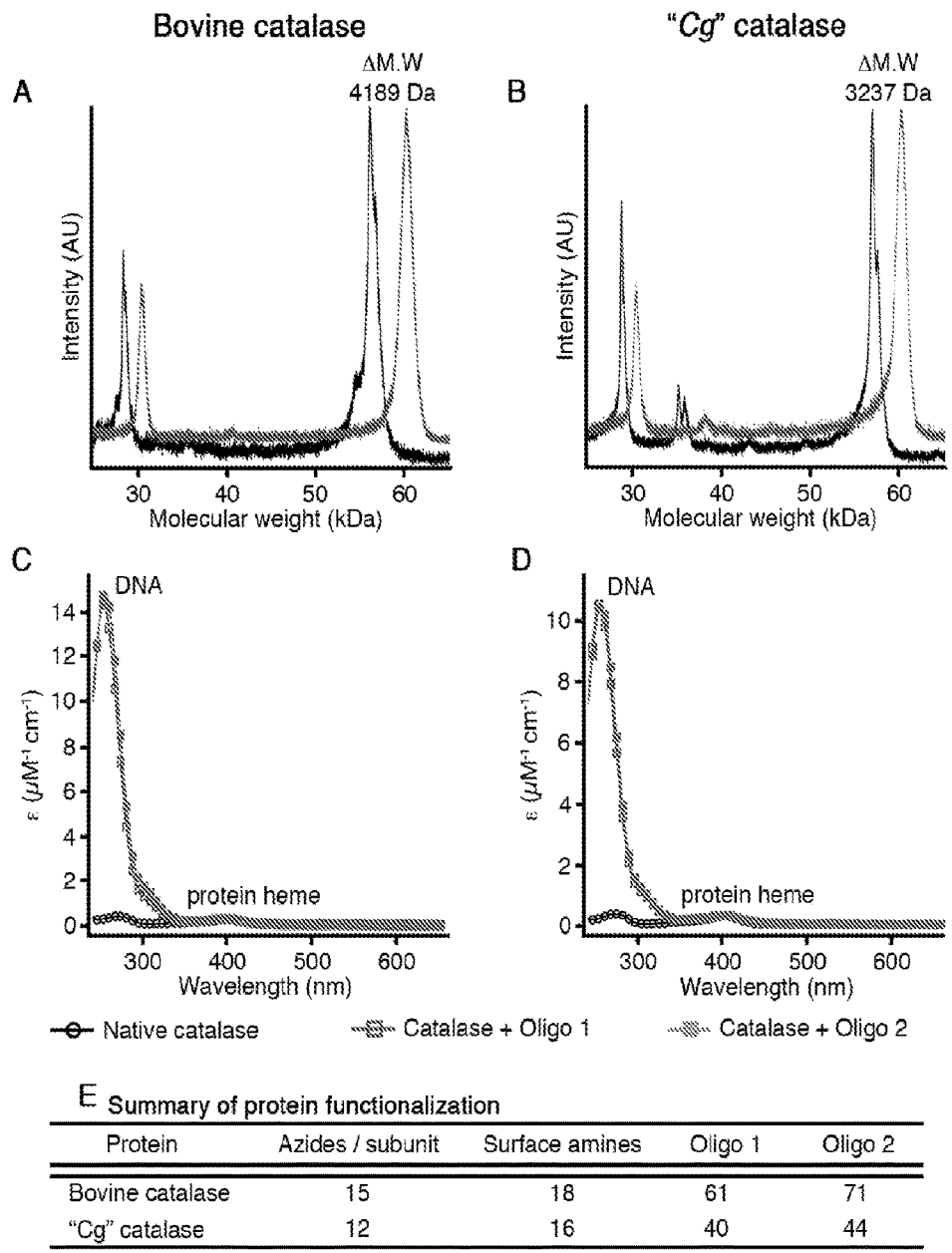
FIGS. 16a-e shows a determination of the extent of labeling of proteins with azides by MALDI-MS. The extent of functionalization of native (left line) and N3-labeled (right line) bovine (FIG. 16a) and Cg (FIG. 16b) catalase with azides was determined by MALDI-MS. Each azide linker that reacts with the protein adds 274 Da to its molecular weight. Because the tetrameric enzymes dissociate into monomers during sample preparation and analysis, the values observed here are for a single subunit. The DNA:protein ratio of bovine (FIG. 16c) and Cg (FIG. 16d) catalases with DNA was determined by UV-visible spectroscopy after functionalization with oligonucleotides 1 (open squares) and 2 (closed squares) and extensive washing to remove unreacted DNA. The differential absorbance at 260 nm is due to modification of the proteins with DNA.

Each azide-modified protein was separately functionalized with two distinct oligonucleotides containing a 5'-terminal dibenzocyclooctyne (DBCO) moiety. Typical reactions contained 3 nmol of protein and 1 µmol of the indicated oligonucleotide in PBS (0.5 M NaCl). The reactions were incubated for 3 days at 25° C. while shaking at 1000 rpm, after which unreacted DNA was removed from the reaction solutions by 10 rounds of ultrafiltration (Millipore Amicon Ultra-15 Centrifugal Filter Units). The oligonucleotide:protein ratio of each DNA-functionalized protein was determined by UV-visible absorbance spectroscopy (FIG. 16).

Dynamic light scattering (DLS) experiments were performed on a Malvern Zetasizer Nano. Each sample contained 1 µM of the native, azide-functionalized or DNA-functionalized catalase. The reported spectra and hydrodynamic diameters (FIGS. 1c-e and 15) are based on intensity distributions and are the average of three measurements.

Figure 17:
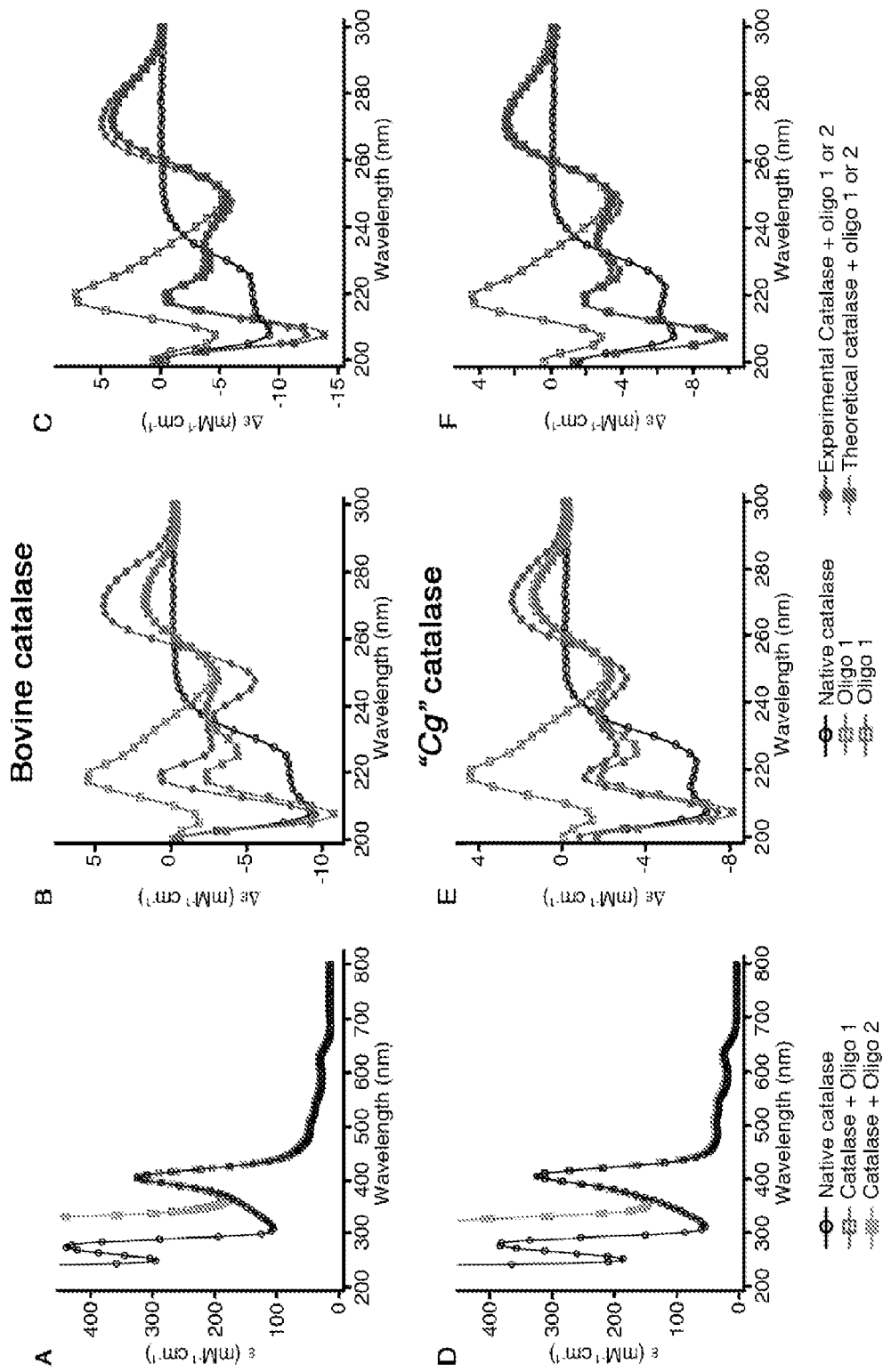
FIGS. 17a-f Structural characterization of native and DNA-functionalized bovine (FIGS. 17a-c) and Cg (FIGS. 17d-f) catalases. UV-visible absorbance spectra of bovine (FIG. 17a) and Cg (FIG. 17d) catalases before (open circles) and after (squares) functionalization with oligonucleotides 1 and 2. Essentially no changes in the visible absorbance spectra of the DNA-functionalized proteins were observed, indicating that the protein environment surrounding the active site is intact after functionalization of either protein with each DNA strand. Circular dichroism spectra of bovine (FIGS. 17b-c) and Cg (FIGS. 17e-f) catalases before (open circles) and after (closed circles) functionalization with oligonucleotide 1 (FIGS. 17b and e) or oligonucleotide 2 (FIGS. 17c and f). The spectra of free oligonucleotides 1 and 2 are represented as open squares and are the product of the $\Delta\varepsilon$ of a single DNA molecule multiplied by the expected DNA:protein ratio. Closed squares represent the sum of the CD spectrum of native catalase and each free oligonucleotide. The agreement between the calculated and observed spectra suggests that the DNA:protein ratios calculated from absorbance spectra are reasonable estimates of the actual degree of functionalization.

UV-visible absorbance and CD spectroscopies were employed to probe the structure of the native, N3- and DNA-functionalized catalase variants (FIGS. 17 and 18). UV-visible absorbance spectra were recorded in a 1-cm-pathlength cuvette containing a solution of approximately 1 µM protein in PBS (0.5 M NaCl). CD spectra were recorded on a Jasco J-818 spectrophotometer in a 1 mm pathlength cuvette. All protein-containing samples were prepared at a concentration of 300 nM in PBS (0.5 M NaCl). The raw ellipticity values (mdeg) were converted to $\Delta\varepsilon$ ($mM^{-1}$ $cm^{-1}$) and the resulting spectra smoothed using a Savitzky-Golay algorithm in Igor Pro (Wavemetrics). Spectra of the azide-functionalized proteins were compared directly to their native counterparts (FIG. 18). The differences in the circular dichroism signal from FIG. 3a and FIG. 18b are due to the spectrum of the azide-labeled protein being relatively unstable. For FIG. 18b, the spectra were collected within a day of completing the labeling experiment, with the modified proteins being stored at 4° C. For FIG. 3a, the azide conjugated protein sat at room temperature for an extended period of time after completion of the conjugation reaction and was partially unfolded.

CD spectra of the unconjugated 5' DBCO-containing oligonucleotides were collected from samples prepared at a concentration of approximately 15 µM. The $\Delta\varepsilon$ value of each DNA strand was then multiplied by the DNA:protein ratio calculated for each protein variant (Table 1). The theoretical spectrum of each DNA-functionalized protein was calculated by summation of the spectrum of the native protein and the spectrum of DNA multiplied by the expected DNA:protein ratio (FIG. 17).

The disproportionation of $H_2O_2$ to $H_2O$ and $O_2$ was followed spectrophotometrically, essentially as previously described [Beers et al., J Biol Chem 195(1): 133-140 (1952)]. Briefly, a 10-µL aliquot of native or DNA-functionalized catalase was added from a stock solution (100 nM) to a stirred cuvette containing the indicated concentration of $H_2O_2$ in 1000 µL of PBS (0.5 M NaCl). After the addition of catalase, the absorbance at 240 nm was monitored continuously for 1 minute. Reaction rates were then calculated from the slopes of the initial linear portions of these traces, using a $H_2O_2$ $\varepsilon_{240}$ value of 43 $M^{-1}$ $cm^{-1}$. Each data point represents the average of three trials (FIG. 19). Standard velocity constants ($k_{app}$) were calculated for each $H_2O_2$ concentration and the average is reported in FIG. 19h. To test whether the observed catalytic activity was due to the presence of intact folded catalase, and not free porphyrin or porphyrin embedded in a matrix of unfolded protein and DNA, enzyme assays were also performed using DNA-functionalized protein that were unfolded by incubation at 60° C. for 10 minutes (FIG. 19).

Protein crystals (assembled as described below) were isolated by four rounds of centrifugation at 5,000 rpm. The total concentration of protein contained in the purified crystals was determined by recording their UV-visible absorbance spectrum at 40° C. The crystals were then diluted to a final protein concentration of 100 nM and their catalytic activity was tested (FIGS. 14f and 19). To test the recyclability of the enzyme crystals, they were incubated with 15 mM $H_2O_2$ for 10 minutes and centrifuged to collect the remaining insoluble material. After this treatment, both the supernatant and insoluble materials were tested for catalytic activity (FIG. 19j). This process was repeated 5 times, after which a SAXS spectrum was collected to ensure that the crystal lattice remained intact (FIG. 19k).

Figure 20:
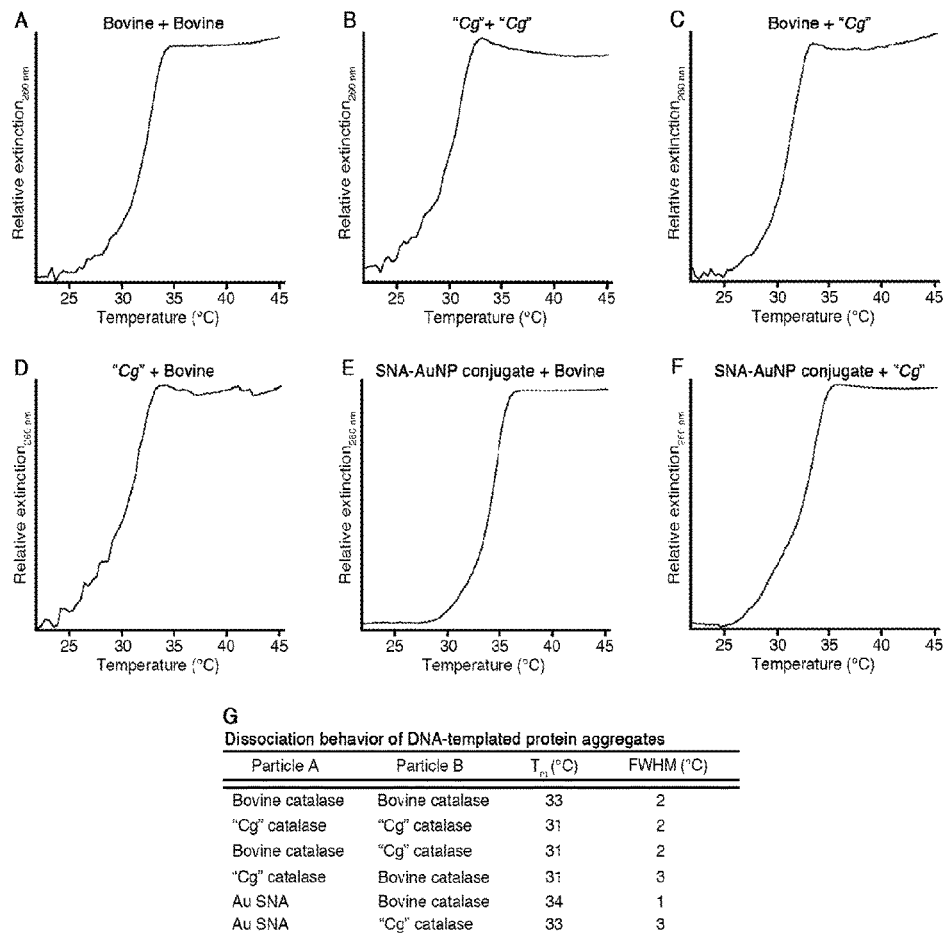
FIGS. 20a-g shows an analysis of the thermal melting transitions of DNA-templated protein aggregates. Aggregates were assembled from each possible combination of two proteins (FIGS. 20a-d) hybridized to linkers bearing complementary sticky ends or a protein and a 10 nm-core SNA-AuNP conjugate (FIGS. 20e-f). Melting curves were obtained by following changes in the extinction at 260 nm of an aggregate-containing solution as the temperature was slowly increased (0.1° C./min) from room temperature to 45° C. All particle combinations yielded aggregates that showed a sharp melting transition that is consistent with dense coverage of the surface of the component nanoparticles with oligonucleotides.

DNA-functionalized proteins and AuNP-SNA conjugates were hybridized to complementary linker strands by adding 100 eq. of the appropriate linker to a solution containing 300 nM of the indicated protein in PBS (0.5 M NaCl). Protein-containing aggregates were assembled by mixing a single DNA-functionalized protein separately hybridized to two different linkers, two different DNA-functionalized proteins, each of which was hybridized with a linker complementary to the other, or a DNA-functionalized protein and a SNA-AuNP conjugate separately hybridized to complementary linkers. The resulting aggregates were added to 1000 μL of PBS (0.5 M NaCl) to a final particle concentration of 15 nM and their melting temperatures determined by UV-visible absorbance spectroscopy (FIGS. 14g and 20). The first derivative of each melting curve was calculated to determine the $T_m$ and full width at half maximum (FWHM) of each sample.

Crystals were assembled by heating DNA-templated aggregates composed of either linker hybridized DNA-functionalized proteins or a linker hybridized protein and a SNA-AuNP conjugate above their melting temperatures (43° C.) and slowly cooling them to room temperature at a rate of 0.01° C./min. This procedure was recently shown to favor the formation of single crystalline over polycrystalline superlattices [Auyeung et al., Nature 505(7481): 73-77 (2014)].

Figure 21:
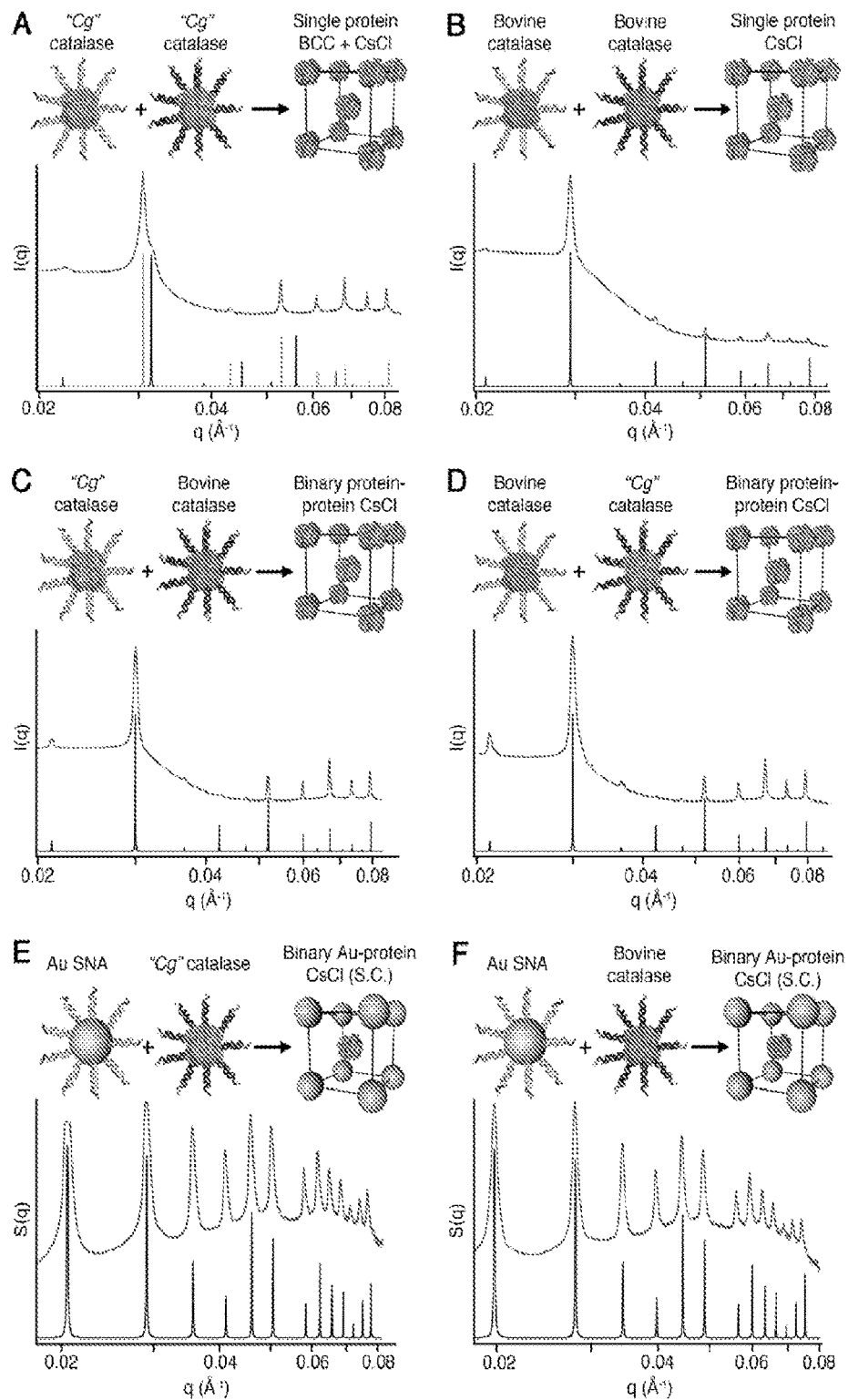
FIGS. 21a-f shows SAXS data for protein-protein (FIGS. 21a-d) and protein-AuNP (FIGS. 21e-f) superlattices. Each panel shows a comparison between the experimentally-observed one-dimensional SAXS patterns (upper traces) and theoretical predictions (lower traces) for protein-containing superlattices. A schematic representation of the components and unit cell of each superlattice type is shown at the top of each panel, where Cg catalase, bovine catalase and AuNPs are depicted as a red cartoon, cyan cartoon, or gold sphere, respectively. The superlattices are isostructural with FIG. 21a) a mixture of BCC (blue theoretical trace) and CsCl (black theoretical trace), (FIGS. 21b-d) CsCl, and (FIGS. 21e-f) simple cubic.

SAXS experiments were carried out at the DuPont-Northwestern-Dow Collaborative Access Team (DND-CAT) beamline of Argonne National Laboratory's Advanced Photon Source (APS). Experiments were performed with 10 keV (wavelength 1.24 Å) collimated X-rays calibrated against a silver behenate standard. Samples were transferred to 1.5 mm quartz capillaries (Charles Supper) and their 2D scattering patterns recorded in situ on a CCD area detector. Exposure times used were 0.5 seconds and 5 seconds for Au-protein hybrid and protein-only lattices, respectively. The one-dimensional scattering data presented in FIG. 21 were obtained by radial averaging of the 2-dimensional data to obtain plots of scattering intensity as a function of the scattering vector q:

$q = 4\pi \sin \theta / \lambda$ where θ is one-half of the scattering angle and λ is the wavelength of the X-rays used.

All theoretical X-ray diffraction patterns were calculated using the PowderCell software package available free of charge on the internet from the Federal Institute for Materials Research and Testing. Although this software was initially developed for calculating structure factors for lattices based on atomic constituents, it has also been shown to generate theoretical scattering patterns for nanoparticle superlattices that match well with experimental data. For binary superlattices assembled from proteins and AuNPs, where the resulting scattering pattern is dominated by the AuNPs and is characteristic of a simple cubic lattice, the atom choice is arbitrary. The same is true for BCC-type lattices composed of a single protein. To generate simulated diffraction patterns for CsCl-type lattices composed of a single protein or two proteins, atoms with similar electron densities were chosen. The positions of the diffraction peaks in the simulated scattering patterns matched well with those experimentally observed.

The nearest neighbor distance d for each lattice type was calculated based on the position of the first scattering peak $q_0$ using the following equation:

$$d = \left(\frac{1}{10}\right)\left(\frac{C}{q_0}\right)$$

where d is the distance in nm between two particles, $q_0$ is the position of the initial scattering peak in 1/Å, and C is a constant that correlates the distance between two nanoparticle nearest neighbors and the distance between the [hkl] planes associated with the first scattering peak. Values of C, $q_0$, d, and lattice parameters are summarized in Table 2.

TEM imaging was performed on a Hitachi HD2300 scanning transmission electron microscope operated at 200 keV in SE or Z-contrast mode. Binary superlattices composed of SNA-AuNP conjugates and DNA-functionalized proteins were embedded in amorphous silica as previously described [Auyeung et al., Nature 505(7481): 73-77 (2014); Auyeung et al., Adv Mater 24(38): 5181-5186 (2012)]. This procedure is necessary to prevent the DNA-mediated lattices from collapsing during sample preparation and imaging under vacuum. A 5-μL aliquot of these silica-embedded superlattices was drop-cast onto a carbon-coated copper mesh grid and excess liquid was removed by blotting with Whatman filter paper. Superlattices composed solely of DNA-functionalized proteins were stained with a 2% solution of uranyl acetate to obtain sufficient contrast for imaging.

Figure 14:
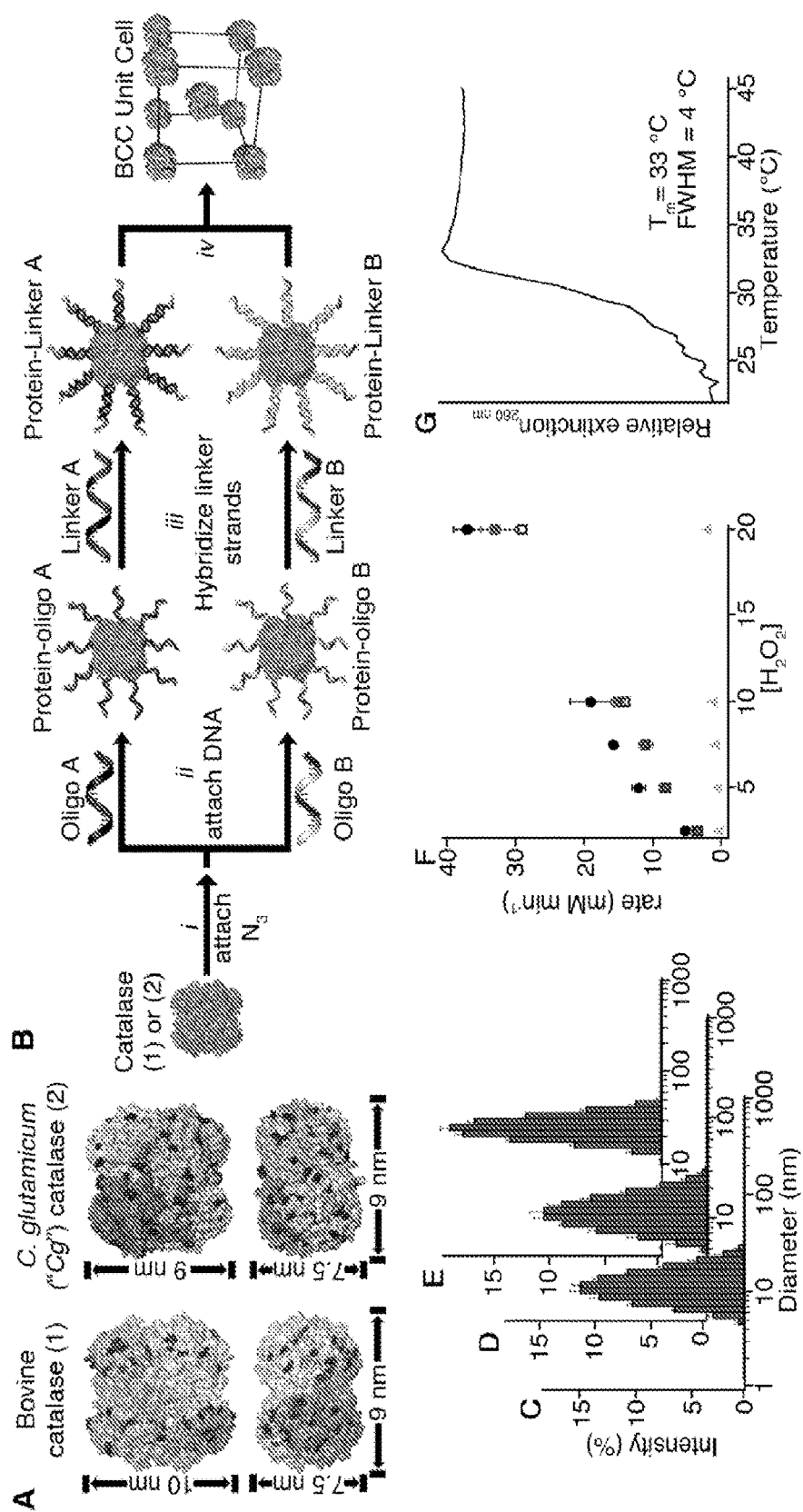
FIGS. 14a-g depict additional synthesis and characterization of protein-DNA conjugates.

Results. Two variants of the tetrameric heme-containing enzyme, catalase (bovine catalase and Cg catalase), were employed as a model system for studying the DNA-mediated assembly of proteins (FIG. 14). Each catalase variant shares a similar molecular topology, but features a distinct pattern of chemically reactive surface-accessible amine functional groups. By adding a large excess (approximately 3000-fold relative to the protein concentration) of tetraethylene glycol linkers containing an N-hydroxysuccinimide (NHS) ester and an azide moiety at opposing termini (FIGS. 14b, i and 15, inset), these surface-accessible amines were converted to azides in high yields (75% and 83% of all solvent-accessible primary amines per tetrameric protein complex for Cg and bovine catalases, respectively), as determined by mass spectrometry (FIG. 16). The functionalization of the proteins with azides was highly reproducible (15.3±0.3 and 12.2±0.6 labels for bovine and Cg catalases, respectively) over five independent reactions using three different batches of protein. The azide-modified proteins were then separately functionalized with two different oligonucleotides (Table 1, below) via a strain-promoted cycloaddition reaction (Cu-free "click chemistry") between the surface-bound azides and dibenzocyclooctyne (DBCO) moieties at the 5' termini of synthetic oligonucleotides (FIG. 14b, ii). This strategy yielded DNA functionalization densities of 30-50 pmol/cm$^2$, as determined by changes in the UV absorbance spectrum of each protein-DNA conjugate (FIG. 16). These values are comparable to those achieved with similarly sized inorganic nanomaterials previously employed in DNA-mediated crystallization schemes [Zhang et al., Nat Mater 12(8): 741-746 (2013); Hurst et al., Anal Chem 78(24): 8313-8318 (2006)]. Further characterization of each protein conjugate by dynamic light scattering (DLS) revealed increases in their hydrodynamic diameters after DNA functionalization from 11.7 or 12 nm to 24.3 and 25 nm for bovine and Cg catalases, respectively, which is consistent with the formation of a shell of oligonucleotides oriented radially from the protein cores (FIGS. 14c-e and 15). Without wishing to be bound by theory, it is likely that the linker interacts with the protein to some extent, which explains why the hydrodynamic diameter does not increase as much as expected. Similarly, the DNA is likely not conformationally identical to DNA in superlattices and adopts additional secondary structure with the surrounding strands, as evidenced by CD spectroscopy (FIG. 17).

TABLE 1

Sequences of oligonucleotides used in the disclosure.

| Description | Sequence (5'-3') | $\varepsilon_{260}$ (M$^{-1}$ cm$^{-1}$) |
|---|---|---|
| DBCO-modified 1 | DBCO dT-Sp$_2$-AAG ACG AAT ATT TAA GAA (SEQ ID NO: 4) | 200,500 |
| DBCO-modified 2 | DBCO DT-Sp$_2$-AAC GAC TCA TAT TAA CAA (SEQ ID NO: 5) | 188,300 |
| Thiol-modified 1 | C6 SS-SP$_2$-AAG ACG AAT ATT TAA GAA (SEQ ID NO: 6) | 200,500 |
| Linker 1 | TTCCTT-Sp-TTC TTA AAT ATT CGT CTT (SEQ ID NO: 7) | 213,3000 |
| Linker 2 | AAGGAA-Sp-TTG TTA ATA TGA GTC GTT (SEQ ID NO: 8) | 248,200 |

1. DBCO dT refers to the dibenzocyclooctyne modified phosphoramidite manufactured by Glen Research
2. Sp refers to the hexaethyleneglycol-modified phosphoramidite, Spacer 18, manufactured by Glen Research.

The azide- and DNA-modified proteins were extensively characterized to ensure that they remained folded and functional. The structure of each protein was probed by UV-visible and circular dichroism (CD) spectroscopies, which provide structural information pertaining to the environment surrounding the heme active site and the global secondary structure of the protein, respectively (FIGS. 17 and 18). Both techniques suggest that the native protein structure remains largely intact upon functionalization with azides or DNA. Retention of the catalytic functionality of the DNA-functionalized proteins was determined spectrophotometrically by monitoring decreases in the UV absorbance (at 240 nm) of hydrogen peroxide ($H_2O_2$, $\varepsilon_{240}$=43 M$^{-1}$ cm$^{-1}$) upon its catalase-catalyzed disproportionation into $H_2O$ and $O_2$ (FIGS. 14f and 19) [Beers et al., J Biol Chem 195(1): 133-140 (1952)]. The initial rate of this reaction is first order with respect to the $H_2O_2$ concentration when mM concentrations of substrate and relatively low (nM) concentrations of enzyme are employed. The standard velocity constants were similar for DNA-functionalized enzymes and their native counterparts, and agreed well with previously published reports [Beers et al., J Biol Chem 195(1): 133-140 (1952)], indicating that the dense shell of DNA appended to the surface of each catalase variant does not significantly affect substrate access to the active site or cause detrimental changes in its structure. In contrast, when the DNA-functionalized proteins were heated above their unfolding temperatures prior to the assay, no $H_2O_2$ decomposition was observed (FIG. 19). This finding demonstrates that the rate enhancements observed in the presence of the DNA-functionalized proteins originate from intact active sites, rather than from peroxidase activity resulting from free heme or heme embedded in a matrix of unfolded proteins and DNA.

Example 5

It was next determined whether the protein-DNA conjugates adopted the DNA-dependent properties characteristic of SNA-inorganic NP conjugates. These conjugates form multivalent interactions with particles bearing complementary oligonucleotides, and these interactions are characterized by a highly cooperative transition between the assembled and disassembled states upon gradual increases in temperature. Each protein-DNA conjugate was independently hybridized to a complementary oligonucleotide bearing a single-stranded sticky end sequence (5'-AAGGAA-3' or 5'-TTCCTT-3', FIG. 14b, iii and Table 1). When proteins bearing linkers with complementary sticky ends were combined, or when either protein was combined with a SNA-gold nanoparticle (AuNP) (10 nm diameter) conjugate with complementary sticky ends, a rapid increase in the turbidity of the solution and a gradual accumulation of aggregates were observed. Significantly, this aggregation event did not occur when particles with non-complementary sticky ends were combined, ruling out the possibility of non-specific interactions between proteins, proteins and the AuNP surface, or proteins and DNA. Solutions containing these DNA-templated aggregates were slowly heated, resulting in a sharp increase in their extinction at 260 nm (FIGS. 14g and 20). For aggregates containing only DNA-functionalized proteins, this transition results from dehybridization of double stranded DNA into hyperchromatic single-stranded DNA upon dissociation of the aggregates, whereas for aggregates containing a mixture of DNA-functionalized proteins and SNA-AuNP conjugates, the increase in the extinction is largely due to changes in the optical properties of the AuNPs. The melting temperatures and full width at half maximum values for these transitions were similar to those observed for SNA-NP conjugates with inorganic cores [Zhang et al., Nat Mater 12(8): 741-746 (2013); Hurst et al., Anal Chem 78(24): 8313-8318 (2006)].

It was next determined whether the design rules developed for SNA-inorganic NP conjugates [Macfarlane et al., Science 334(6053): 204-208 (2011); Macfarlane et al., Angew Chem Int Ed 52(22): 5688-5698 (2013)] also apply to the assembly of DNA-functionalized proteins. It has previously been shown that when spherical SNA-AuNP conjugates with identical sizes are separately functionalized with linkers bearing non-self-complementary sticky ends, the thermodynamically favorable lattice is body-centered cubic. These lattices are defined as BCC-type rather than CsCl because the core nanoparticles are identical, despite the fact that they are functionalized with distinct DNA sequences. To test whether DNA-functionalized proteins form similar lattices, aggregates containing an equimolar ratio of two proteins, or a binary system consisting of a protein and a SNA-AuNP conjugate, were heated to a temperature above their melting point, but below the temperature at which protein unfolding begins, and slowly cooled to 20° C. at a rate of 0.01° C./min to promote the formation of the thermodynamically stable product. It has been shown that compared to an alternative procedure where aggregates are annealed at a temperature slightly below their melting temperature, slowly cooling nanoparticle-containing solutions from a dissociated state favors the formation of single crystals over polycrystalline aggregates [Auyeung et al., Nature 505(7481): 73-77 (2014)]. The rate of 0.01° C./min was determined empirically, after observing that faster cooling rates yielded ill-defined single crystals or polycrystalline aggregates. Using this procedure, Cg catalase assembled into superlattices with body centered cubic (BCC) symmetries and an interparticle spacing of 25.6 nm, as determined from the radially averaged 1D small angle X-ray scattering (SAXS) pattern (FIG. 21a). This interparticle spacing is consistent with the measured hydrodynamic diameter of DNA-modified Cg catalase (FIGS. 14e and 15). An additional diffraction peak at 0.022 Å-1 and a shoulder at 0.03 Å-1 were also observed, suggesting the presence of a separate lattice isostructural with cesium chloride (CsCl). Crystals formed from the three additional protein-protein combinations also produced scattering patterns characteristic of CsCl-type lattices, although the presence of a BCC lattice with similar interparticle spacings cannot be ruled out (FIG. 21b-d; Table 2). The formation of lattices with CsCl-type symmetries, rather than BCC symmetry, from nearly identical protein variants suggests that although the proteins located at each unique lattice position are forming connections with eight nearest neighbors, as expected, they are also adopting distinct orientations. This observation indicates that the unique shape anisotropy and non-uniform surface chemistry of the protein building blocks affects DNA-mediated superlattice assembly in a manner that has not been observed using traditional SNA-NP conjugates and will be leveraged in design efforts to form lattices with novel symmetries.

building block, highlights the broad generalizability of DNA-mediated assembly and is useful in assembling multifunctional materials.

Figure 22:
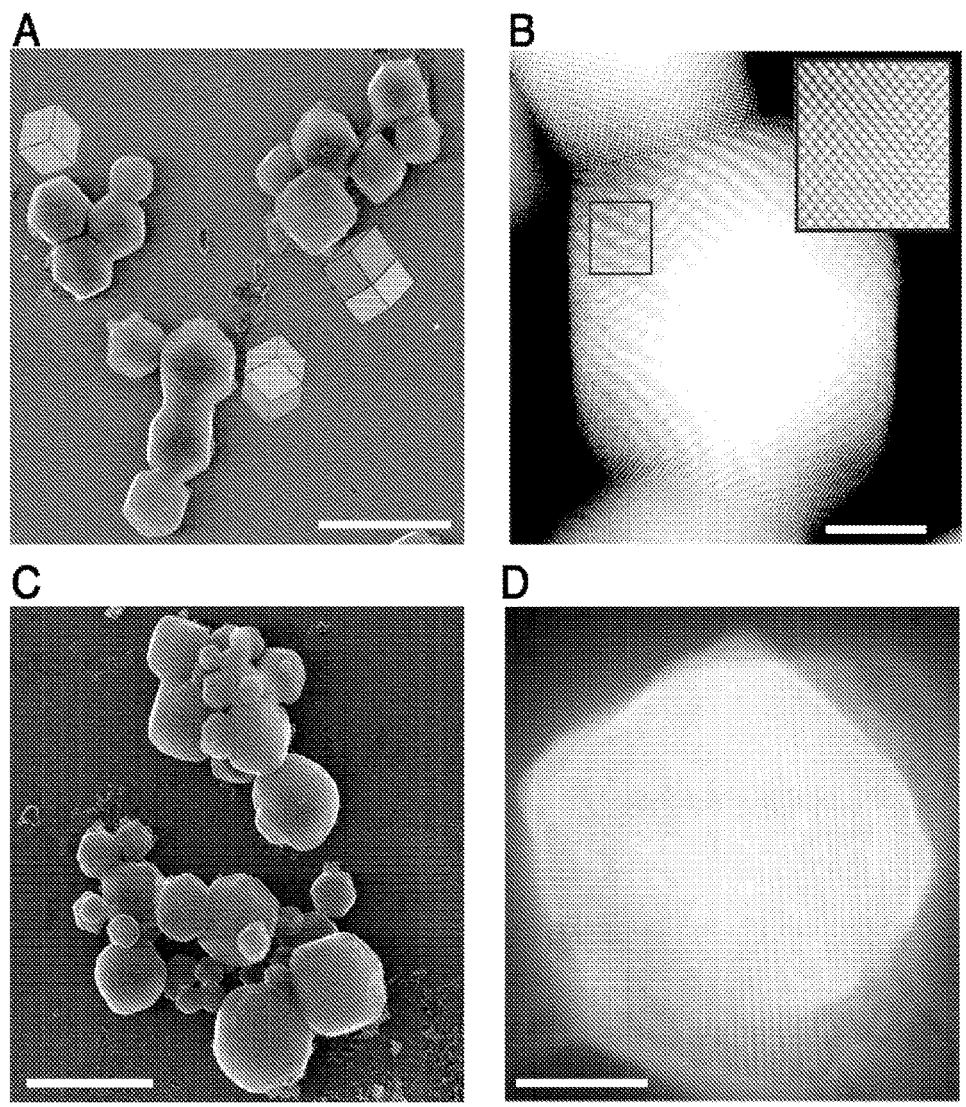
FIGS. 22a-d shows a characterization of single crystalline superlattices by TEM. Low (FIG. 22a) and high (FIG. 22b), magnification TEM micrographs of Cg catalase-AuNP hybrid superlattices showing the uniform formation of the expected rhombic dodecahron crystal habit. Cartoon depictions of the various orientations of a rhombic dodecahedron are shown side-by-side with experimentally observed superlattices with matching orientations. The inset in (FIG. 22b) depicts the high degree of short-range order between AuNPs within a single crystal. Figures c-d) Low and high magnification TEM images of superlattices composed of Cg catalase.
Figure 23:
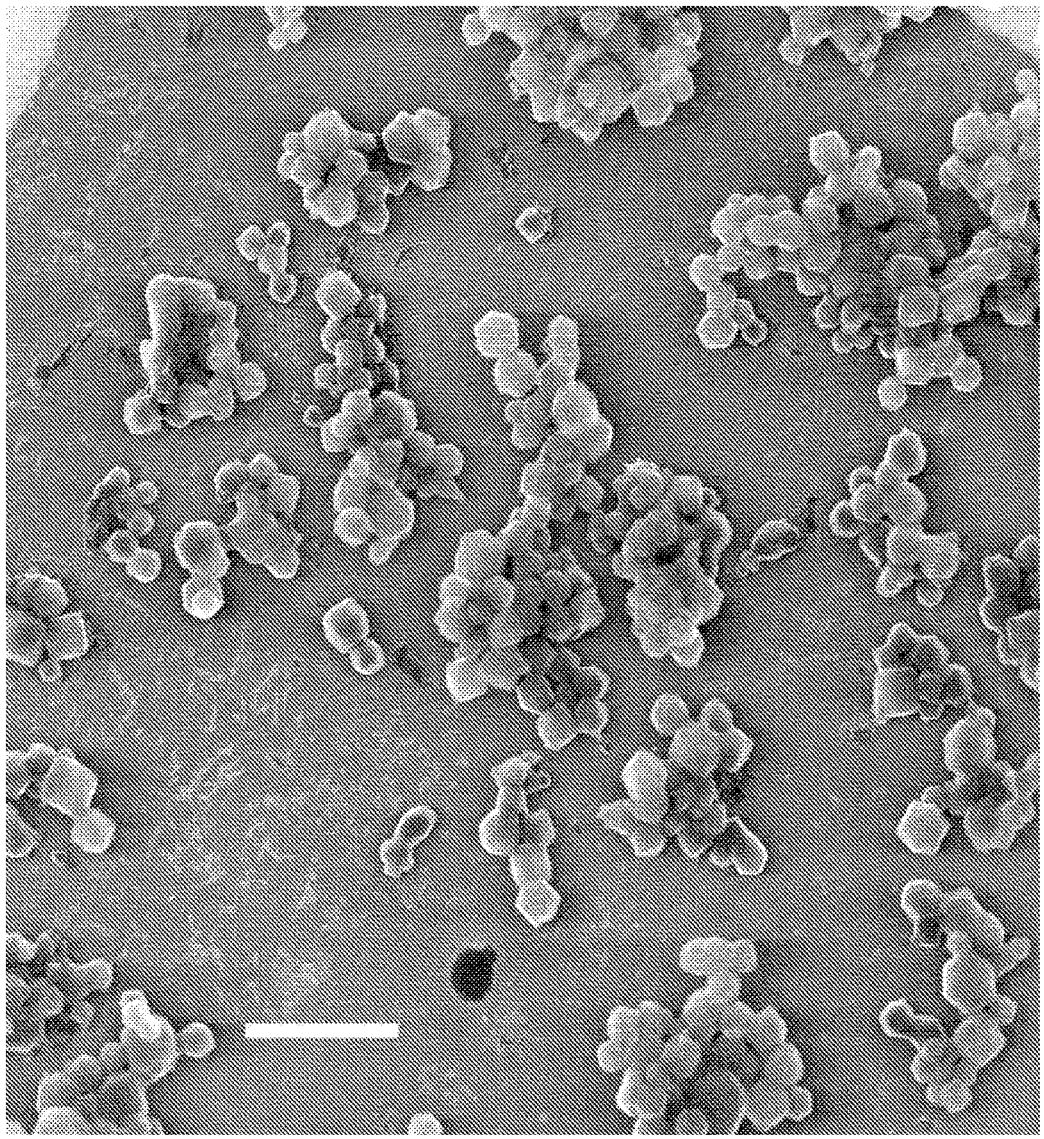
FIG. 23 shows a representative low magnification micrograph of single-crystalline superlattices assembled from DNA-functionalized Cg catalase and SNA-AuNP conjugates. Scale bar=10 μm.

The microscale morphologies of the protein crystals were investigated by scanning transmission electron microscopy (STEM) of silica embedded (for binary protein-Au systems) or negatively stained (for lattices composed only of DNA-functionalized proteins) specimens (FIGS. 22 and 23). Micrographs of both samples demonstrate the uniform formation of single crystals 1-7 μm in each dimension. Binary protein-AuNP crystals displayed clear facets and hexagonal and square domains, similar to those previously observed for SNA-AuNP conjugates that assemble into rhombic dodecahedra [Auyeung et al., Nature 505(7481): 73-77 (2014)]. This occurs despite the fact that for Au-protein binary crystals, the inclusion of a protein spacer results in a simple cubic arrangement of AuNPs. High magnification images of a single crystal with a binary protein-AuNP composition (FIG. 22b) revealed a remarkable degree of order, with stacks of individual nanoparticles clearly discernible (FIG. 22b, inset). Similarly, lattice planes could be visualized in negatively stained specimens prepared from Cg catalase crystals (FIG. 22d).

The crystals composed of Cg catalase were employed in $H_2O_2$ decomposition assays, as described above, to determine if the enzymes remained active after the crystallization process. As with native or DNA-functionalized enzymes free in solution, the rate of $H_2O_2$ decomposition by the crystals showed a linear dependence on the substrate concentration (FIG. 19i), although the apparent rate constants were reduced by a factor of approximately 20. Similar decreases in catalytic efficiency have previously been observed in studies of crystalline enzyme preparations, especially for highly efficient enzymes where diffusion into the crystal is a limiting factor [Mozzarelli et al., Annu Rev

TABLE 2

Calculation and Summary of Lattice Parameters.

| Particle A | Particle B | Lattice Symmetry | [hkl] planes | $q_0$ (1/Å) | $d_{NP}$ (nm) | Lattice parameter (nm) | C |
|---|---|---|---|---|---|---|---|
| Cg catalase | Cg catalase | BCC | [110] | 0.0303 | 25.3 | 29.2 | $\sqrt{6}\pi$ |
| Cg catalase | Cg catalase | CsCl | [100] | 0.0222 | 24.5 | 28.3 | $\sqrt{3}\pi$ |
| Bovine catalase | Bovine catalase | BCC | [110] | 0.0294 | 26.2 | 30.2 | $\sqrt{6}\pi$ |
| Bovine catalase | Bovine catalase | CsCl | [100] | 0.0208 | 26.1 | 30.1 | $\sqrt{3}\pi$ |
| Cg catalase | Bovine catalase | BCC | [110] | 0.0299 | 25.6 | 29.6 | $\sqrt{6}\pi$ |
| Cg catalase | Bovine catalase | CsCl | [100] | 0.0212 | 25.2 | 29.1 | $\sqrt{3}\pi$ |
| Bovine catalase | Cg catalase | BCC | [110] | 0.0299 | 25.6 | 29.6 | $\sqrt{6}\pi$ |
| Bovine catalase | Cg catalase | CsCl | [100] | 0.0212 | 25.2 | 29.1 | $\sqrt{3}\pi$ |
| Cg catalase | AuNP | SC | [100] | 0.0205 | 26.4 | 30.6 | $2\pi$ |
| Bovine catalase | AuNP | SC | [100] | 0.0198 | 27.4 | 31.7 | $2\pi$ |

Because the scattering cross-sections of proteins relative to AuNPs are negligible, protein-AuNP binary lattices are expected to produce scattering patterns that are dependent solely on the arrangement of AuNPs within the lattice. Indeed, when DNA-functionalized proteins were combined in a 1:1 ratio with SNA-AuNP conjugates bearing linkers with complementary sticky ends, the resulting CsCl-type lattices produced simple cubic scattering patterns (FIG. 21e-f). In these lattices, the protein acts as a three-dimensional spacer that effectively deletes lattice positions that would otherwise be occupied by AuNPs. The ability to combine two types of nanomaterials with such disparate physical and chemical properties, without significantly altering the compact 3D structure of the soft protein-based Bioph Biom 25: 343-365 (1996)]. Significantly, the enzymes could be easily recycled after catalysis by centrifugation and retained full catalytic activity throughout at least 5 rounds of catalysis (FIG. 19j). Analysis of the insoluble material by SAXS after the final round of catalysis confirmed that the crystal lattice remained intact (FIG. 19k).

Conclusions. Despite recent achievements [King et al., Science 336(6085): 1171-1174 (2012); King et al., Nature 510(7503): 103-108 (2014)], the de novo design of protein-protein interactions, especially to form supramolecular structures beyond dimeric complexes, remains difficult due to a lack of universal interaction motifs [Stranges et al., Protein Sci 22(1): 74-82 (2013)]. In contrast, oligonucleotide base pairing interactions are well understood, form with high fidelity, and have been widely employed as a means for assembling diverse supramolecular shapes that can act as scaffolds for organizing the assembly of external molecules, including proteins or protein-based virus capsids [Wilner et al., Nat Nanotechnol 4(4): 249-254 (2009); Zhang et al., Angew Chem Int Ed 51(14): 3382-3385 (2012); Rusling et al., Angew Chem Int Ed 53(15): 3979-3982 (2014); Yan et al., Science 301(5641): 1882-1884 (2003); Wang et al., ACS Nano 8(8): 7896-7904 (2014); Coyle et al., J Am Chem Soc 135(13): 5012-5016 (2013)]. By replacing the formation of inter-protein interactions with oligonucleotide hybridization, the present disclosure has shown that crystalline superlattices can be assembled from a single protein, multiple proteins, or a combination of proteins and AuNPs. This strategy provides, inter alia, a means for programming the assembly of complex biomaterials (e.g., enzyme cascades or hybrid inorganic-organic lattices) from functional proteins regardless of their amino acid compositions or molecular topologies.

What is claimed is:

1. A method of inhibiting expression of a gene product encoded by a target polynucleotide comprising:
contacting a target polynucleotide with a nanoparticle comprising a core, a plurality of polynucleotides comprising a shell, and a linker,
wherein the linker connects the core to at least one polynucleotide of the plurality of polynucleotides comprising the shell and comprises:
Formula (I), (II), or both:

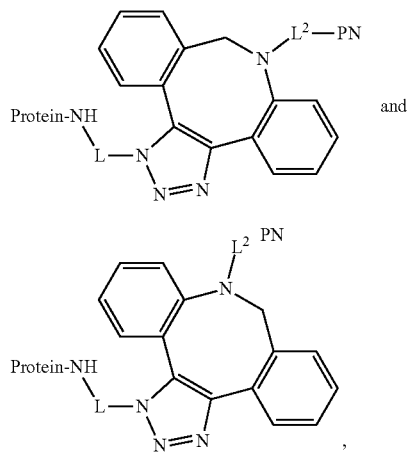

L and $L_2$ are each independently selected from C1-10 alkylene, —C(O)—C1-10 alkylene-Y— and —C(O)—C1-10 alkylene-Y—C1-10 alkylene-(OCH$_2$CH$_2$)m-Y—;
each Y is independently selected from the group consisting of a bond, C(O), O, NH, C(O)NH, and NHC(O);
m is 0, 1, 2, 3, 4, or 5; and
PN is the at least one polynucleotide of the plurality of polynucleotides comprising the shell,
wherein the core is a single protein,
wherein the single protein exhibits catalytic activity, the single protein does not exhibit transport activity and the single protein is not albumin,
wherein the plurality of polynucleotides comprising the shell are attached to the surface of the single protein via covalent bonds at a surface density of at least 10 pmol/cm$^2$,
wherein at least one polynucleotide of the plurality of polynucleotides comprising the shell is attached to the single protein surface via a surface amino group from a lysine residue of the single protein,
wherein at least one polynucleotide of the plurality of polynucleotides is sufficiently complementary to the target polynucleotide to hybridize under conditions sufficient to inhibit expression of the gene product by at least 10%, and
wherein at least one polynucleotide of the plurality of polynucleotides is 5 to 40 nucleotides in length.

2. The method of claim 1, wherein the single protein is not a fragment.

3. The method of claim 1, wherein at least one polynucleotide of the plurality of polynucleotides is 5 to 30 nucleotides in length.

4. The method of claim 1, wherein the single protein is beta galactosidase or catalase.

5. The method of claim 1, wherein the shell attached to the surface of the single protein via covalent bonds are at a surface density of at least 15 pmol/cm$^2$.

6. The method of claim 1, wherein the shell attached to the surface of the single protein via covalent bonds are at a surface density of at least 20 pmol/cm$^2$.

7. The method of claim 1, wherein the shell attached to the surface of the single protein via covalent bonds are at a surface density of at least 25 pmol/cm$^2$.

8. The method of claim 1, wherein the shell attached to the surface of the single protein via covalent bonds are at a surface density of at least 30 pmol/cm$^2$.

9. The method of claim 1, wherein the shell attached to the surface of the single protein via covalent bonds are at a surface density of at least 35 pmol/cm$^2$.

10. The method of claim 1, wherein the shell attached to the surface of the single protein via covalent bonds are at a surface density of at least 40 pmol/cm$^2$.

11. The method of claim 1, wherein expression of the gene product is inhibited by at least 10% compared to gene product expression in the absence of the nanoparticle.

12. A method of inhibiting expression of a gene product encoded by a target polynucleotide comprising:
contacting a target polynucleotide with a nanoparticle comprising a core a plurality of polynucleotides comprising a shell, and a linker,
wherein the linker connects the core to at least one polynucleotide of the plurality of polynucleotides comprising the shell and comprises:
Formula (I), (II), or both:

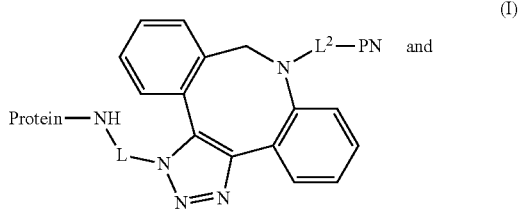

-continued

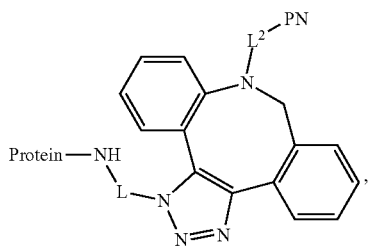
(II)

L and L₂ are each independently selected from C1-10 alkylene, —C(O)—C1-10 alkylene-Y—, and —C(O)—C1-10 alkylene-Y—C1-10 alkylene-(OCH₂CH₂)m-Y—;
each Y is independently selected from the group consisting of a bond, C(O), O, NH, C(O)NH, and NHC(O);
m is 0, 1, 2, 3, 4, or 5; and
PN is the at least one polynucleotide of the plurality of polynucleotides comprising the shell,
wherein the core is a single protein,
wherein the single protein:
(a) exhibits catalytic activity and exhibits therapeutic activity, but the single protein is not albumin, or
(b) exhibits catalytic activity and exhibits therapeutic activity, but the single protein is not a fragment,
wherein the plurality of polynucleotides comprising the shell are attached to the surface of the single protein via covalent bonds at a surface density of at least 10 pmol/cm²,
wherein at least one polynucleotide of the plurality of polynucleotides comprising the shell is attached to the single protein surface via a surface amino group from a lysine residue of the single protein,
wherein at least one polynucleotide of the plurality of polynucleotides is sufficiently complementary to the target polynucleotide to hybridize under conditions sufficient to inhibit expression of the gene product by at least 10%, and
wherein at least one polynucleotide of the plurality of polynucleotides is 5 to 40 nucleotides in length.

13. The method of claim 12, wherein at least one polynucleotide of the plurality of polynucleotides is 5 to 30 nucleotides in length.

14. The method of claim 12, wherein each polynucleotide of the plurality of polynucleotides is 5 to 30 nucleotides in length.

15. The method of claim 12, wherein the shell attached to the surface of the single protein via covalent bonds are at a surface density of at least 15 pmol/cm².

16. The method of claim 12, wherein the shell attached to the surface of the single protein via covalent bonds are at a surface density of at least 20 pmol/cm².

17. The method of claim 12, wherein the shell attached to the surface of the single protein via covalent bonds are at a surface density of at least 25 pmol/cm².

18. The method of claim 12, wherein the shell attached to the surface of the single protein via covalent bonds are at a surface density of at least 30 pmol/cm².

19. The method of claim 12, wherein the shell attached to the surface of the single protein via covalent bonds are at a surface density of at least 35 pmol/cm².

20. The method of claim 12, wherein the shell attached to the surface of the single protein via covalent bonds are at a surface density of at least 40 pmol/cm².

21. The method of claim 12, wherein expression of the gene product is inhibited by at least 10% compared to gene product expression in the absence of the nanoparticle.

* * * * *

SEQUENCE LISTING

```
<160> NUMBER OF SEQ ID NOS: 12

<210> SEQ ID NO 1
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: DBCO (dibenzocyclooctyne modified
      phosphoramidite)
<220> FEATURE:
<221> NAME/KEY: misc_feature
<222> LOCATION: (1)..(1)
<223> OTHER INFORMATION: SP(hexaethyleneglycol-modified phosphoramidite)

<400> SEQUENCE: 1
aagaatttat aagcagaa                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: DBCO (dibenzocyclooctyne modified
      phosphoramidite)
<220> FEATURE:
<221> NAME/KEY: misc_feature
<222> LOCATION: (1)..(1)
<223> OTHER INFORMATION: SP(hexaethyleneglycol-modified phosphoramidite)

<400> SEQUENCE: 2
aacaattata ctcagcaa                                                 18

<210> SEQ ID NO 3
<211> LENGTH: 20
<212> TYPE: DNA
<213> ORGANISM: Artificial Sequence
<220> FEATURE:
<223> OTHER INFORMATION: Artificial Sequence
<220> FEATURE:
<221> NAME/KEY: misc_feature
<222> LOCATION: (1)..(1)
<223> OTHER INFORMATION: DBCO (dibenzocyclooctyne modified
      phosphoramidite)
<220> FEATURE:
<221> NAME/KEY: misc_feature
<222> LOCATION: (11)..(12)
<223> OTHER INFORMATION: linked via a  Cy5 phosphoramidite

<400> SEQUENCE: 3
tttttttttt tttttttttt                                               20
```

```
<210> SEQ ID NO 4
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: DBCO (dibenzocyclooctyne modified
      phosphoramidite)
<220> FEATURE:
<221> NAME/KEY: misc_feature
<222> LOCATION: (1)..(1)
<223> OTHER INFORMATION: SP(hexaethyleneglycol-modified phosphoramidite)

<400> SEQUENCE: 4
aagacgaata tttaagaa                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: DBCO (dibenzocyclooctyne modified
      phosphoramidite)
<220> FEATURE:
<221> NAME/KEY: misc_feature
<222> LOCATION: (1)..(1)
<223> OTHER INFORMATION: SP(hexaethyleneglycol-modified phosphoramidite)

<400> SEQUENCE: 5
aacgactcat attaacaa                                                 18

<210> SEQ ID NO 6
<211> LENGTH: 26
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(9)
<223> OTHER INFORMATION: linked via SP(hexaethyleneglycol-modified
      phosphoramidite)

<400> SEQUENCE: 6 cccccssaa gacgaatatt taagaa                                         26

<210> SEQ ID NO 7
<211> LENGTH: 24
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: linked via SP(hexaethyleneglycol-modified
      phosphoramidite)

<400> SEQUENCE: 7
ttccttttct taaatattcg tctt                                          24

<210> SEQ ID NO 8
<211> LENGTH: 24
<212> TYPE: DNA
```

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: linked via SP(hexaethyleneglycol-modified
      phosphoramidite)

<400> SEQUENCE: 8
aaggaattgt taatatgagt cgtt                                            24

<210> SEQ ID NO 9
<211> LENGTH: 18
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(1)
<223> OTHER INFORMATION: DBCO (dibenzocyclooctyne modified
      phosphoramidite)
<220> FEATURE:
<221> NAME/KEY: misc_feature
<222> LOCATION: (1)..(1)
<223> OTHER INFORMATION: SP(hexaethyleneglycol-modified phosphoramidite)

<400> SEQUENCE: 9
aagacgaata tttaaaag                                                   18

<210> SEQ ID NO 10
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)..(5)
<223> OTHER INFORMATION: linked via SP(hexaethyleneglycol-modified
      phosphoramidite)

<400> SEQUENCE: 10
gcgcttgtta atatgagtcg tt                                              22

<210> SEQ ID NO 11
<211> LENGTH: 22
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (4)..(5)
<223> OTHER INFORMATION: linked via SP(hexaethyleneglycol-modified
      phosphoramidite)

<400> SEQUENCE: 11 gcgccttttaaatattcgtc tt                                               22

<210> SEQ ID NO 12
<211> LENGTH: 24
<212> TYPE: DNA
<213> ORGANISM: Artificial Sequence
```

```
<220> FEATURE:
<223> OTHER INFORMATION: Synthetic polynucleotide
<220> FEATURE:
<221> NAME/KEY: misc_feature
<222> LOCATION: (6)..(7)
<223> OTHER INFORMATION: linked via SP(hexaethyleneglycol-modified
      phosphoramidite)

<400> SEQUENCE: 12
ttccttcttt taaatattcg tctt                                              24
```